United States Patent [19]

Goodman et al.

[11] Patent Number: 4,849,411
[45] Date of Patent: * Jul. 18, 1989

[54] MODULATION OF ANIMAL CELLULAR RESPONSES WITH COMPOSITIONS CONTAINING 8-SUBSTITUTED GUANINE DERIVATIVES

[75] Inventors: Michael G. Goodman, Carlsbad; William O. Weigle, Del Mar, both of Calif.

[73] Assignee: Scripps Clinic and Research Foundation, La Jolla, Calif.

[ * ] Notice: The portion of the term of this patent subsequent to Sep. 3, 2002 has been disclaimed.

[21] Appl. No.: 14,618

[22] Filed: Feb. 13, 1987

Related U.S. Application Data

[63] Continuation of Ser. No. 546,679, Nov. 1, 1983, Pat. No. 4,643,992, which is a continuation-in-part of Ser. No. 439,846, Nov. 9, 1982, Pat. No. 4,539,205.

[51] Int. Cl.$^4$ .......................... A61K 31/70; C12N 5/00
[52] U.S. Cl. ................................... 514/45; 435/240.2; 424/85.8
[58] Field of Search ................... 424/85, 85.8; 514/45; 435/240.1–240.2

[56] References Cited

U.S. PATENT DOCUMENTS 3,498,970  3/1970  Yamoda et al. ...................... 536/24

OTHER PUBLICATIONS

Goodman et al., Proc. Natl. Acad. Sci., vol. 78, pp. 7604–7608, 1981.
Chemical Abstracts, vol. 71, No. 25, Abstract No. 119619g, 1969.
Chemical Abstracts, vol. 98, No. 3, Abstract No. 15346g, 1983.
Chemical Abstracts, vol. 99, No. 5, Abstract No. 3654g, 1983 Goodman et al., J. Immunology, pp. 2399–2404, 1982.

*Primary Examiner*—Blondel Hazel
*Attorney, Agent, or Firm*—Dressler, Goldsmith, Shore, Sutker & Milnamow, Ltd.

[57] ABSTRACT

Compositions and methods for their use in modulating animal cellular responses are disclosed. The compositions include as an active agent an effective amount of an 8-substituted guanine derivative bonded 9-1' to an aldose having 5 or 6 carbon atoms in the aldose chain. The composition includes a diluent amount of a physiologically tolerable carrier. The guanine derivative is free of electrically charged functionality, while the 8-substituent has an electron withdrawing inductive effect greater than that of hydrogen and contains fewer than about 15 atoms. Animal cellular responses are modulated by contacting the cells with a composition of this invention.

17 Claims, 31 Drawing Sheets

MODULATION OF ANIMAL CELLULAR RESPONSES WITH COMPOSITIONS CONTAINING 8-SUBSTITUTED GUANINE DERIVATIVES

The U.S. Government has rights in this invention pursuant to Grants AI 15284 and AI 07007 awarded by the United States Public Health Service, Biomedical Research Support Grant RRO-5514, and U.S. Public Health Service Research Career Development Award AI 00374.

CROSS REFERENCE TO RELATED APPLICATION

This is a continuation of application Ser. No. 546,679, filed Nov. 1, 1983, now U.S. Pat. No. 4,643,992, which is a continuation-in-part application of co-pending application, Ser. No. 439,846, filed Nov. 9, 1982, now U.S. Pat. No. 4,539,205.

TECHNICAL FIELD

The present invention relates to modulation of animal cellular responses, and more particularly to modulation of immune and other responses by compositions containing a low molecular weight derivative of guanine.

BACKGROUND ART

An animal's immune system is comprised of numerous elements that act separately and/or in concert to counteract, to eliminate, or to neutralize substances that are recognized by that system as foreign to the animal host. Generally, but not necessarily, the substance recognized as foreign by the immune system has its origin exogenous to the host. Exemplary of such exogenous substances are infectious bacteria and the by-products of their cellular activity, virus particles and their proteins, proteins injected by insect stings, and the like. In autoimmune diseases, such as rheumatoid arthritis, the host's immune system recognizes host-made proteins or self-made proteins as foreign.

The principal effectors of the immune system are the leukocytes, which include lymphocytes of thymic origin (T cells), lymphocytes produced in bone marrow (B cells), neutrophils which, inter alia, produce enzymes that make oxidizing agents such as hydrogen peroxide that have cytotoxic effects upon bacteria, and macrophages which present the foreign substance or antigen to the T cells, as well as produce a protein designated interleukin-1 that assists T cell transformation into T helper cells. Complement which is a complex mixture of proteins that acts in an ordered, cascading manner upon the foreign substance also plays a major role in immune responses.

B cells can be distinguished from T cells, inter alia, by the presence of immunoglobulins on their membrane surfaces. The immunoglobulins function as antibodies.

There are five known classes of immunoglobulins, identified as IgA, IgD, IgE, IgG, and IgM on the basis of five antigenically different heavy protein chains which in part make up the immunoglobulin molecule. B cells also bear non-immunoglobulin cell markers, including a complement receptor (CR), a receptor for the Fc portion of immunoglobulin (FCR), I-region associated antigens (Ia), and a set of differentiation antigens (Lyb 1-7) which are identified by all antisera and are correlated with various aspects of B cell maturation and activation. These markers are useful in phenotypically identifying B cells.

While the B cell immunoglobulins act upon the foreign substance, or antigen, the T cells, and particularly helper T cells, are believed necessary to stimulate B cells to divide and to differentiate into antibody secreting cells for humoral immunity. Supressor T cells contribute to the regulation of humoral immunity, while cytotoxic T cells and T cell mediators of delayed-type hypersensitivity are the principal effectors of cell-mediated immunity.

T cells include antigens designated Lyt 1, 2, and 3 that are related to T cell functions. Helper T cell precursors are of the Lyt $1^+$, $2^-$, $3^-$ phenotype. It is these cells which normally participate in the activation and regulation of B cells.

Helper T cells are known to assist in activation and differentiation of immunoglobulin-secreting B cells after a first message is received by the B cells from the activating antigenic agent. However, the mode by which the T cells provide the second message of activation and differentiation to the B cells is a matter of controversy.

Guanosine-3', 5'-cyclic monophosphate (cGMP) has been implicated as a naturally occurring agent for providing the required second message. 8-Bromoguanosine-3', 5'-cyclic monophosphate (8-BrcGMP) has been found to be a weak synthetic intracellular lymphocyte mitogen.

The immune response can be modified by artificial supression (immunosuppression) or enhancement (immunopotentiation). Immunosuppression, i.e., artifically induced decreased responsiveness, can be achieved by six general methods: (1) administration of antigen, (2) administration of specific antisera or antibody, (3) use of other biologic reagents such as antilymphocyte antisera, (4) use of drugs or hormones, (5) radiation, and (6) surgical removal of lymphoid tissue. Immunopotentiation can include the administration of an agent effecting an increase in the rate at which the immune response develops, an increase in the intensity or level of the response, a prolongation of the response, or the development of a response to an otherwise non-immunogenic substance.

The agents which are known to enhance immune responses are generally termed adjuvants and can be placed into two general categories: (1) those providing general potentiation, i.e., substances which enhance both cellular and humoral immune responses for a wide variety of antigens, and (2) those providing specific potentiation, i.e., substances which enhance specific responses to certain antigens only.

Substances that can act as adjuvants can be grouped into the following categories: (1) water and oil emulsions, e.g., Freund's adjuvant, (2) synthetic polynucleotides, (3) hormones, drugs and cyclic nucleotides, (4) endotoxins, (5) lymphokines and monokines such as the interleukins.

A substance capable of specifically potentiating the immune response is transfer factor, a dialyzable leukocyte extract (DLE) obtained from human peripheral leukocytes. It has been reported that the transfer factor exhibits some effectiveness in patients with immunodeficiencies and possible effectiveness in cancer patients and in patients with limited immunodeficiencies. However, much remains to be learned about this particular substance.

In some diseases and physiological conditions such as X-linked agammaglobulinemias, senescence and drug-induced-immunosuppression, B cell activation and differentiation is lacking and/or exists only at a reduced level, thereby lessening the immune response of the host. These diseases and conditions are representative of immunosuppressed states. Here, enhanced activation and differentiation, if it can be effected, tends to beneficially lessen the disease manifestation and/or improve the patient's condition.

An immunopotentiated state can be illustrated by the bodily condition after vaccination. Here, the immune response is already enhanced due to an antigenic response, but could be beneficially enhanced still further to provide an improved degree and/or duration of immunity.

Neoplastic cell proliferation, including primary tumors and metastatic disease, typically can be explained as a manifestation of a cellular message that causes the cells to replicate without the normal regulatory restraints and/or at a much higher rate than is normal for the unaffected cells. One usual chemotherapeutic treatment for neoplastic diseases is to contact the neoplastic cells with low levels of materials that are generally cytotoxic in the hope that the general cytotoxicity will affect the rapidly replicating neoplastic cells to a greater extent than the normal cells and thereby selectively kill the rapidly replicating neoplastic cells. The drawbacks of such treatments include a general depression of many bodily functions, including loss of weight and hair, stomach and bowel disorders, and the like.

Interferons are a class of soluble, small proteins that inhibit virus multiplication. These proteins are produced by cells infected with substantially any animal virus particles or other viral agents, as well as by agents such as bacterial products and monoclonal antibodies. Interferons are cell-specific but not virus-specific. It would be beneficial in promoting an animal's general resistance to viral infection if the level of interferons present in the animal could be increased in the absence of naturally occurring (pathogenic) microbiological interferon-inducing agents.

In autoimmune diseases, the host recognizes its own proteins as antigens and, in essence, attacks itself through the production of antibodies to its own tissues. Since animals normally produce some antibodies to themselves (anti-self antibodies) whose effects are suppressed or tolerated, it is thought that autoimmune diseases may be a result of an overly active production of anti-self antibodies to which the usual suppression and/or tolerance-providing bodily mechanisms do not adequately respond. Such an over production of anti-self antibodies can be taken as analogous on the antibody level to the excess cellular proliferation exhibited by neoplastic cells.

Salicylates, such as acetyl salicylate (aspirin), are major chemotherapeutic agents for combatting autoimmune diseases such as rheumatoid arthritis. It is believed that the salicylates act to relieve the symptoms of rheumatoid arthritis by suppression of prostaglandin production and therefore their effect on the afflicted tissue. Chemotherapeutic agents such as gold, mercaptopurine and D-penicillamine have been utilized to treat rheumatoid arthritis, but some such drugs have toxic or teratogenic side effects, and their use has been associated with incidence of lymphoma and infection. It would therefore be advantageous to provide a chemotherapeutic agent that could be used to successfully treat autoimmune diseases without the above-noted side effects.

Lymphokines and monokines are immunopotentiating proteins produced by lymphocytes and cells of the monocyte-macrophage lineage respectively. One monokine, interleukin-1, is produced by macrophages when they are stimulated by a mitogen or antigen. Interleukin-1 is usually required for producing a primary antigenic response.

Interleukin-1 assists in the production of interleukin-2 in T cells. Interleukin-2 is a growth factor for T cells and assists in the transformation of T helper cells. Thus, induction of interleukin-1 production or of a protein-responsive activity on T cells similar to that produced by interleukin-1 would be beneficial in enhancing immune responses, particularly where macrophages are absent or where their interleukin-1 production is deficient.

BRIEF SUMMARY OF THE INVENTION

It has been found that animal cellular responses can be modulated by the administration of a composition that includes as an active ingredient an effective amount of an 8-substituted guanine derivative bonded 9-1' to an aldose having 5 or 6 carbon atoms in the aldose chain. Enhancement of antigen-specific humoral immune responses resulting in potent adjuvanticity, T cell-replacing factor-like (TRF-like) activity and immunoreconstituting activity are particular examples of the animal cellular responses that can be modulated in accordance with the present invention. The guanine derivative is free of electrically charged functionality, while the 8-substituent has an electron withdrawing inductive effect greater than that of hydrogen and contains fewer than about 15 atoms. Particularly preferred 8-substituted guanine derivatives as active agents of animal cellular response-modulating compositions are 8-oxoguanosine, 8-oxo-7-methylguanosine, 8-methoxyguanosine, 8-mercaptoguanosine (8-MGuo), 8-mercapto-7-methylguanosine and the 8-haloguanosines (8-HGuo), especially 8-bromoguanosine (8-BrGuo). The term "modulate" in its various grammatical forms, as used herein, designates enhancement as well as inhibition of an animal cellular response in vitro and/or in vivo.

The cellular response-modulating compositions of this invention also include a diluent ammount of a physiologically tolerable carrier. A response-modulating composition of this invention can be used to provoke differing, although related results depending, inter alia, upon the manner of administration, dosage and the cell population to which it is administered. The active ingredient can be present in the carrier as a suspension of solid 8-substituted guanine derivative in a solid or liquid carrier, or as a solute in the carrier.

Thus, contacting leukocytes such as T lymphocytes, macrophages, neutrophils or B lymphocytes with such a composition of this invention modulates the immune response of those leukocytes. Modulation of B lymphocyte (B cell) responses can be effected by subjecting the B cells to an antigen prior to or simultaneously with contacting the B cells with the immune response modulating composition.

B cell immune responses can also be modulated by subjecting the B cells to antigen and then contacting the cells so subjected with an immune response modulating composition in conjunction with an additional amount of an antigen. These steps can be carried out in an environment exhibiting either the presence or the substantial lack of T lymphocyte helper activity. Immune response modulation can also be effected on senescent B lymphocytes which exhibit a diminished immune response prior to being contacted with a composition of this invention.

Growth of neoplastic cells can be inhibited by contacting such cells with an animal cell response-modulating composition of this invention. Contacting animal cells with a composition of this invention also induces production of interferon even in the absence of naturally occurring microbiological interferon-inducing agents. Similar treatment of macrophages with a composition of this invention in the absence of T cell activity provides an interleukin-1-like activity to the T cells in the absence of antigen, while contacting T cells with a composition of this invention in the presence of IL-2 provides a synergistically enhanced proliferative activity to T cells. Contacting B lymphocytes of a host suffering from autoimmune disease with a composition of this invention suppresses the autoimmune disease.

The compositions and methods of this invention are also useful in enhancing the production of antibodies such as monoclonal antibodies from B cells. Here, for example, an immune response enhancing composition of this invention is contacted with B cells in the animal that is immunized in order to provide an increased frequency of antigen-specific B cells for use in cell fusions to form hybridomas. The monoclonal antibody-producing hybridoma cells can also be contacted in vivo or in vitro with a composition of this invention to enhance the production of monoclonal antibodies from those cells.

The compositions and methods of this invention may be used on cells in vivo as well as in vitro. The compositions may be administered subcutaneously, intraperitoneally, or intraorally as in pill or capsule form, or in liquid form as a slurry, suspension or solution.

The present invention has several benefits and advantages.

One of the salient benefits of this invention is that its use can provide the second message required for B lymphocyte activation and differentiation in response to a first (antigenic) message.

Another benefit of this invention is that the activation and differentiation lead to the induction of protein production, as in the case of immunoglobulin secretion from B cells.

Still another benefit of this invention is that immune-suppressed or immune-deficient conditions and disease manifestations can be improved and/or lessened, respectively, by use of this invention.

Yet another benefit of this invention is that its use can provide improved immunity in hosts with otherwise normally functioning B cell activities.

A particular advantage of the present invention is that enhanced immune responses can be effected in both the presence and absence of T helper cell activity. Thus, enhanced immune responses are noted in both T cell-dependent and T cell-independent systems.

Additional advantages of the present invention are that it can be used to inhibit neoplastic cell growth, stimulate interferon production in the presence or absence of naturally occuring microbiological interferon-inducing agents, and inhibit autoimmune responses.

Still further benefits and advantages of the present invention will be apparent to those skilled in the art from the Figures, Detailed Description, Examples and Claims which follow.

Anthropomorphic descriptions such as the sending and receiving of messages by and to chemicals and cells are used herein for descriptive purposes as aids to the understanding of observed phenomena.

BRIEF DESCRIPTION OF THE DRAWINGS

In the drawings constituting a portion of the disclosure of this invention.

$4 \times 10^6$ Viable splenic B cells from senescent C57BL/6J mice were cultured for 4 days in a volume of 1 ml in the presence or absence of $2 \times 10^6$ SRBC, supplemented with either $10^{-3}$ M 8-MGuo, 0.1 mg/ml LPS, or culture medium alone. Results are expressed as the arithmetic mean of triplicate cultures ± S.E.

Figure 27:
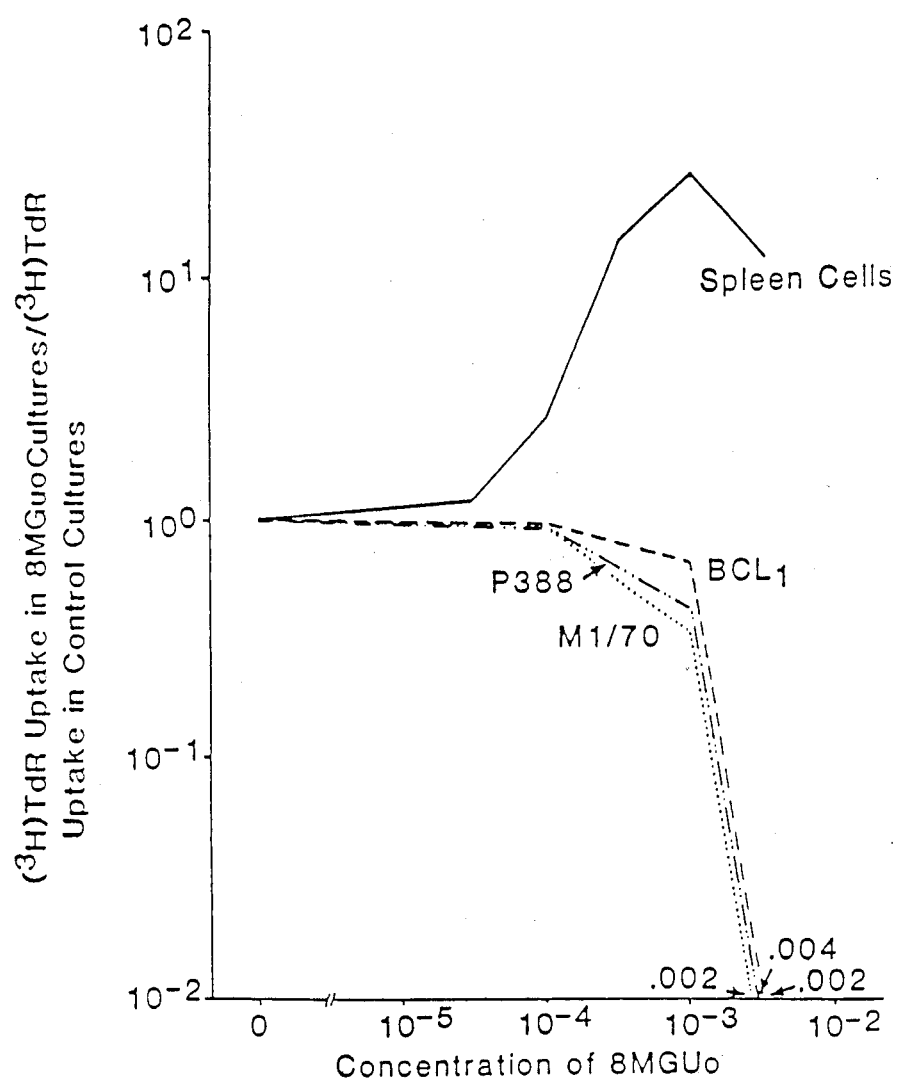

FIG. 27: $4 \times 10^4$ Viable tumor cells or $5 \times 10^5$ normal spleen cells were cultured for two days in the presence of incremental concentrations of 8-MGuo. Cultures were labeled with one micro Ci [$^3$H] TdR for the final 24 hours of incubation. Results are presented as in FIG. 11.

Figure 28:
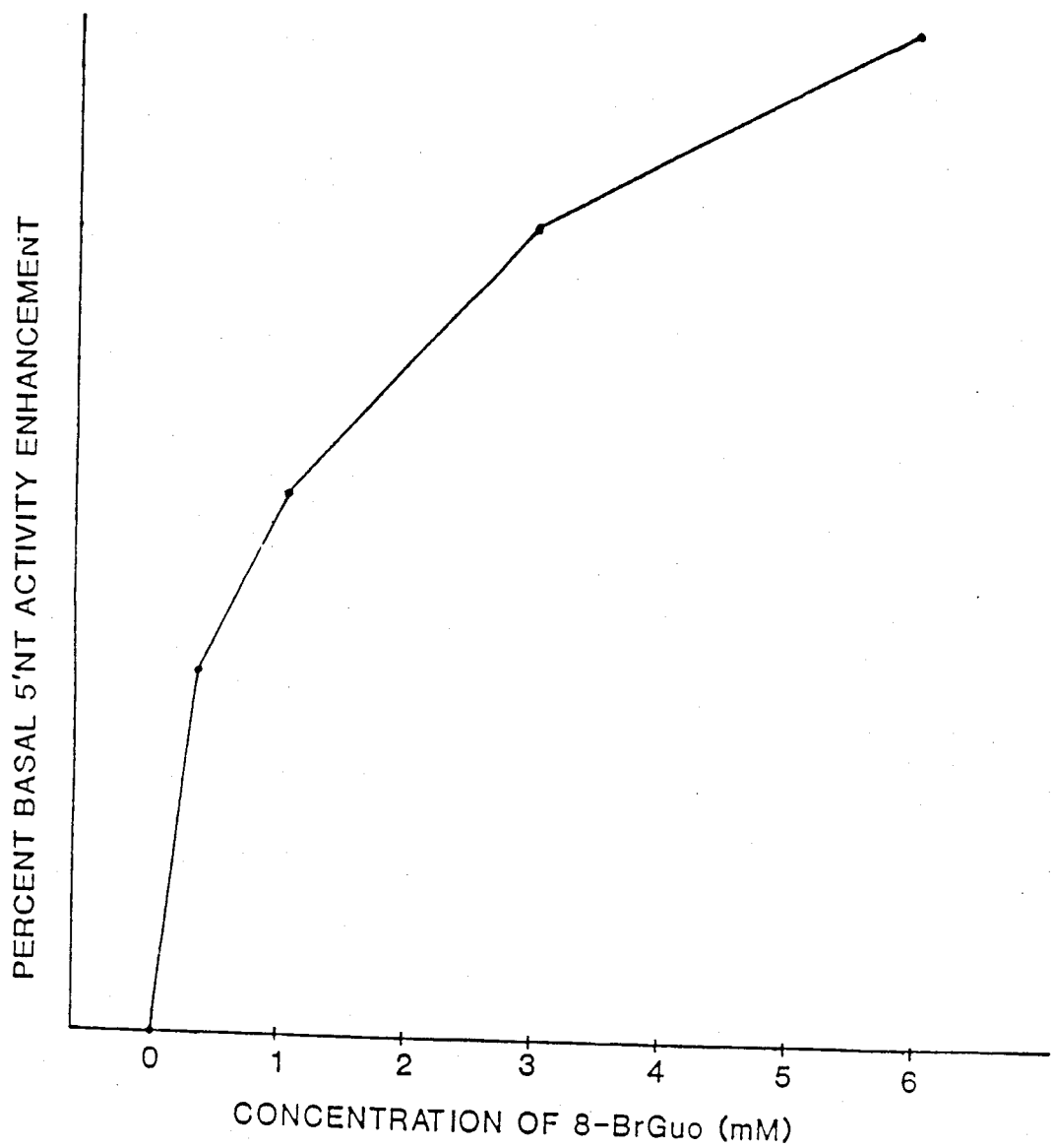

FIG. 28: $10^6$ Viable CBA/CaJ spleen cells were cultured for 3 hours in serum-free medium with 0.1 micro [$^{14}$C] of GMP in the presence of incremental concentrations of 8-BrGuo. At the end of the culture period, cells were centrifuged, the supernate was harvested, supplemented with 1 mM unlabeled Guo or GMP, and analyzed by TLC on PEI cellulose plates. Spots corresponding to Guo or GMP were scraped and beta emissions counted.

Figure 29:
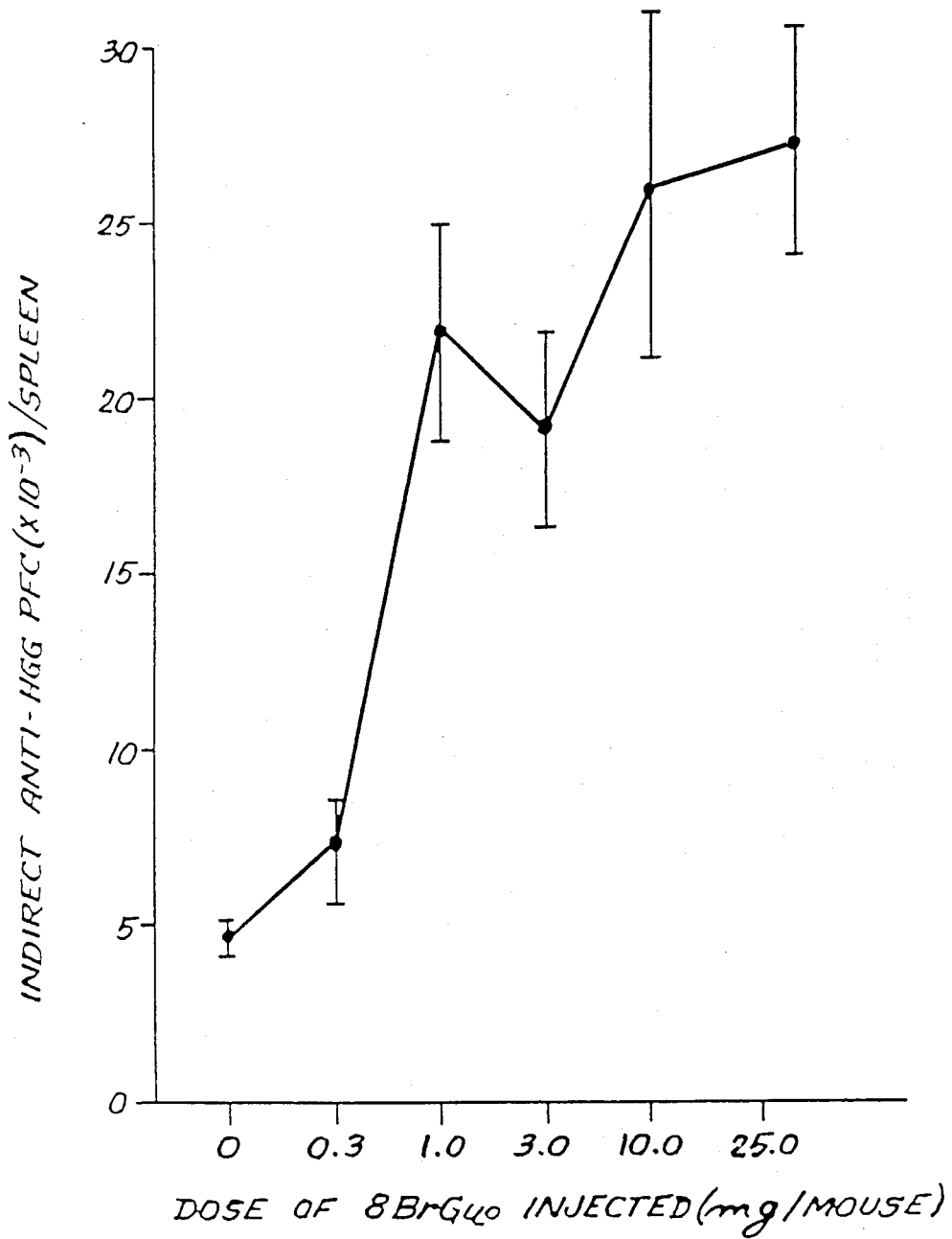

FIG. 29 illustrates the enhancement of the in vivo response to human gamma-globulin (HGG) in A/J mice injected with 400 micrograms of heat aggregated HGG and incremental amounts of 8-BrGuo. The number of indirect (IgG) anti-human gamma-globulin plaque forming cells per spleen were determined six days after immunization with a minimum of 11 mice per datum point. Results are presented as the arithmatic 1 mean ± S.E.

Figure 30:
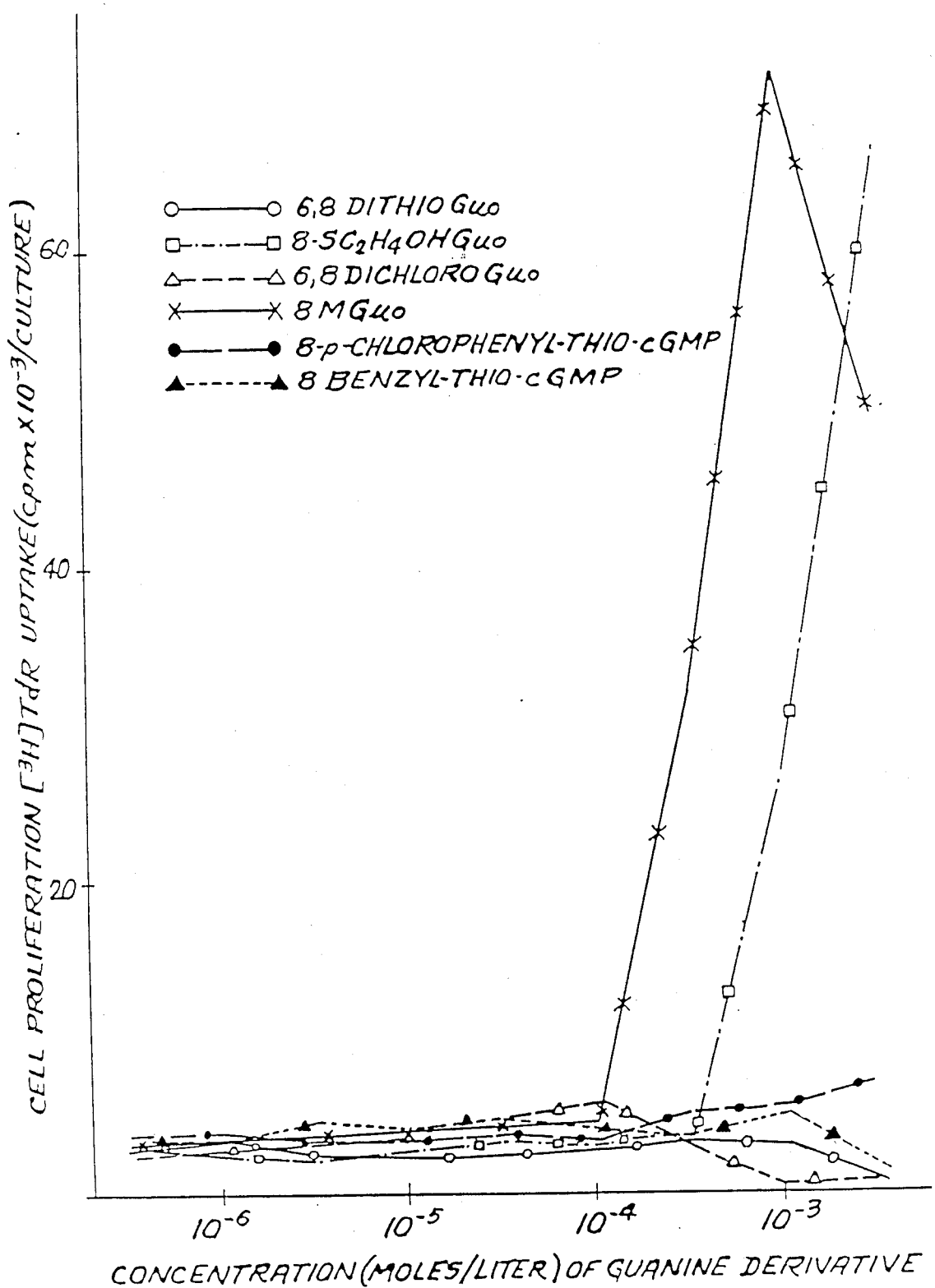

FIG. 30 illustrates the ability of guanine derivatives to promote mitogenesis. $4 \times 10^5$ Viable CBA/CaJ spleen cells were cultured for two days with incremental concentrations of the guanine derivative. Results are presented as in Fiure 10A.

Figure 31:
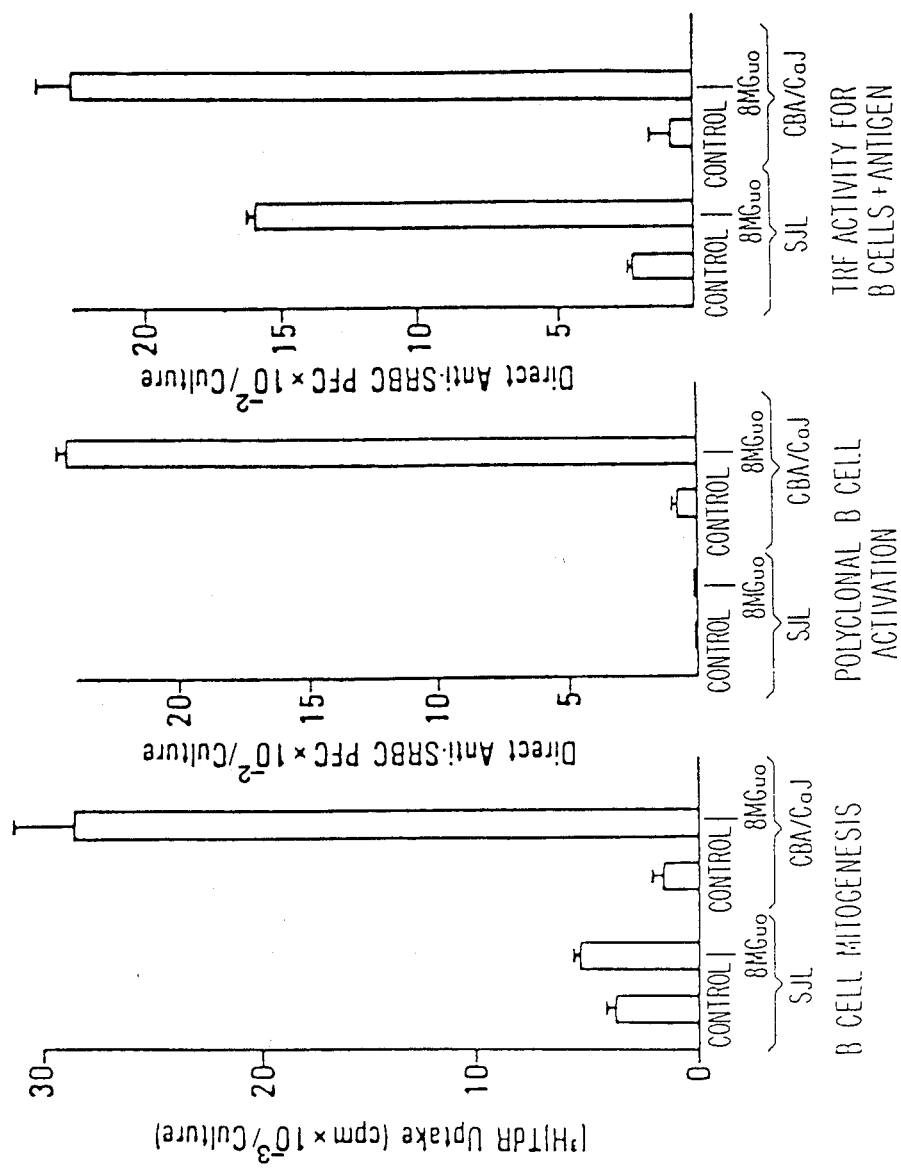

FIG. 31 illustrates the difference between B cell mitogenesis and polyclonal B cell activation as compared to T cell-replacing factor (TRF) activity for murine B cells. SJL or CBA/CaJ B cells were cultured for two days (left panel), three days (middle panel) or four days (right panel) in the assay shown. Using the assay methods referred to hereinbefore in FIG. 11, after 24 hours of culture, the mitogenesis cultures were labeled with [$^3$H] TdR for another 24 hours period and were then harvested. Direct PFC to SRBC were determined for the middle panel as discussed in FIG. 24, while direct PFC to SRBC of the right panel were determined as discussed in FIG. 20.

Figure 32:
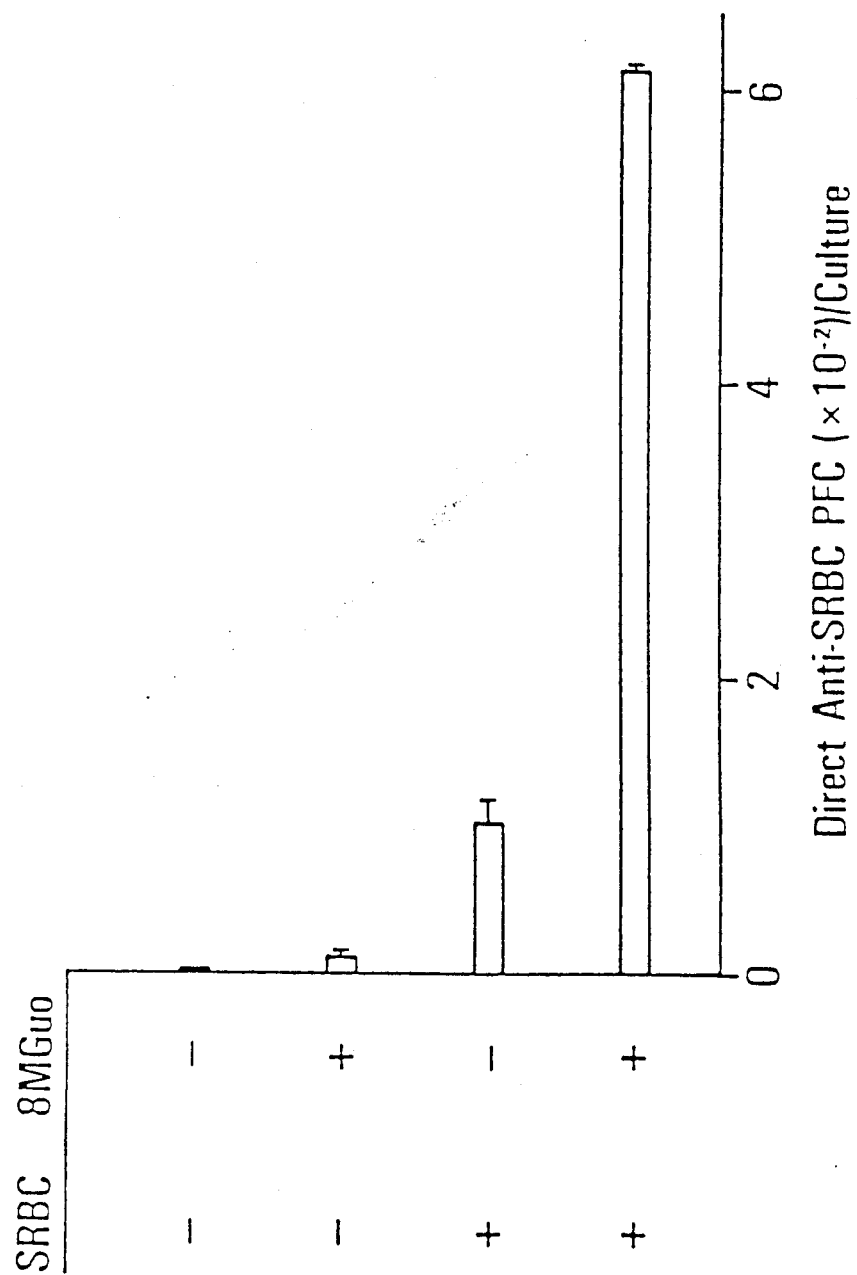

FIG. 32 illustrates an 8-MGuo induced enhancement of human primary immune response to SRBC as antigen. $2 \times 10^6$ Viable human peripheral blood lymphocytes depleted of cells bearing the $H_2$ histamine receptor by "panning" with plates commercially available from Seragen, Inc. of Boston, M.A., using the technique of Wysocki and Sato, Proc. Natl. Acad. Sci. USA, 75:2844 (1978) were cultured for six days in a volume of 1.0 milliliters in a medium containing 10 percent heat-inactivated fresh autologous plasma. $5 \times 10^6$ SRBC and/or a final concentration of $1 \times 10^{-3}$ molar 8-MGuo were present (+) or omitted (−) as indicated. PFC were evaluated using the plaque assay discussed hereinbefore. Results are reported as the arithmetic mean ± S.E. of triplicate cultures.

DETAILED DESCRIPTION OF THE INVENTION

A list of abbreviations utilized herein is set forth in Table I, below.

TABLE I

| Abbreviation | Meaning |
| --- | --- |
| AECM | N—(2-aminoethyl)carbamylmethyl |
| cAMP | adenosine 3',5'-cyclic monophosphate |
| ATS | rabbit anti-mouse thymocyte serum |
| B Cells | bone marrow-derived lymphocytes |
| 8-BrcGMP | 8-bromoguanosine 3',5'-cyclic monophosphate |
| 8-BrGuo | 8-bromoguanosine |
| Con A | concanavalin A |
| CR | complement receptor |
| cGMP | guanosine 3',5'-cyclic monophosphate |
| EA | erythrocyte-antibody complexes |
| EAC | erythrocyte-antibody-complement complexes |
| FcR | Fc receptor |
| FCS | fetal calf serum |
| Guo | guanosine |
| 8-HGuo | 8-haloguanosine |
| [$^3$H]TdR | tritium labelled deoxyribosylthymidine |
| Ia antigen | antigens controlled by the immune response genes |
| IgA, D, E, G and M | immunoglobulins A, D, E, G and M |
| IL | interleukin |
| IL-1 | interleukin-1 |
| IL-2 | interleukin-2 |
| LPS | bacterial lipopolysaccharide |
| Lyb 1-7 | lymphocyte antigens on murine B cells |
| Lyt | lymphocyte antigens on murine T cells |
| 8-MGuo | 8-mercaptoguanosine |
| MHC | major histocompatibility complex |
| MLC | mixed leukocyte culture |
| 5'NT | 5'-Nucleotidase |
| PFC | plaque-forming cell |
| PHA | phytohemagglutinin |
| RBC | red blood cell |
| RIA | radioimmunoassay |
| SRBC | sheep red blood cells |
| S.E. | standard error |
| T cells | thymus-derived lymphocytes |
| TCA | trichloroacetic acid |
| TI-1,-2 | thymus-independent type 1 and 2 responses |
| TNP | 2,4,6-trinitrophenyl |
| TRF | T cell-replacing factor |

In studying the effects of the reportedly mitogenic agents cGMP and 8-BrcGMP, we found that a new class of low molecular weight guanine derivatives, when present in an effective amount as the active ingredient of a composition containing a diluent amount of a physiologically tolerable carrier, provide remarkable effects in modulating responses of animal cells. Enhancement of antigen-specific humoral immune responses resulting in potent adjuvanticity, TRF-like activity and immunoreconstituting activity are particular examples of the animal cellular responses that can be modulated in accordance with the present invention.

The new class of cell response-modulating agents is 8-substituted guanine derivatives that are bonded 9-1' to an aldose having 5 or 6 carbon atoms in the aldose chain. One preferred grouping of active ingredients within this class is constituted by the 8-haloguanosines. Another preferred grouping of active ingredients within this class is constituted by the sulfido or thio (—S—) linkage-containing 8-mercapto- and 8-(substituted mercapto) guanosines. Other preferred groupings within this class are constituted by the oxo (=o) and oxy (—o—) linkage-containing 8-oxo-guanosines and 8-(substituted oxy) guanosines, respectively. It should be noted that the 8-mercapto and 8-oxo guanosines include their tautomeric forms.

The 8-substituent on guanine contains fewer than about 15 atoms, and more preferably contains fewer than about 10 atoms. Most preferably, the 8-substituent contains 1 to about 7 atoms.

Preferred 8-substituents include halo groups such as chlorine, bromine and iodine. The bromine group is particularly preferred. Other preferred substituent groups include a sulfido or thio linkage to the 8-position of the guanine derivative. Exemplary of such groups are those in which the sulfido linkage is part of a mercapto group, an $C_1$–$C_4$ acyl mercapto group such as acetyl mercapto, and an $C_1$–$C_4$ alkyl sulfidogroup such as methyl sulfide or a methylthio group ($CH_3$—S—). Still other preferred 8-substituents include an oxo linkage to the 8-position of the guanine derivative. Exemplary of such substituents include 8-oxo guanosine and 7-methyl-8-oxoguanosine.

One convenient way of characterizing useful 8-substituents of the guanine derivative is by their electron withdrawing inductive effects relative to hydrogen. Hammett substituent sigma constants (sigma constant) calculated for ionization of meta substituents of benzoic acids are useful in predicting relative inductive effects, and are well known to those familiar with physical organic chemistry. See, for example, Hine, *Physical Organic Chemistry*, McGraw-Hill Book Company, New York, pp. 85–88 (1962).

Those substituents that have a greater inductive electron withdrawing effect than hydrogen have positive sigma constant values. Those substituents that exhibit less of an inductive electron withdrawing effect than hydrogen, i.e., electron donors, have negative sigma constant values.

Preferred 8-substituents have an inductive electron withdrawing effect greater than that of hydrogen. Illustrative of such 8-substituents are halo, mercapto, acyl mercapto such as acetyl mercapto, alkyl sulfides such as methyl sulfide (—$SCH_3$), nitro, cyano, oxo, alkoxy, keto such as acetyl, halomethyl such as chloromethyl, and methyleneoxy alkyl ethers such as methyleneoxyethyl (—$CH_2$—O—$CH_2CH_3$).

With reference to Hammett substituent sigma constants for meta benzoic acid substituents, the preferred 8-substituents have positive values. More preferably, the 8-substituents have sigma constants of about 0.1 to about 0.7. The most preferred 8-substituents have sigma constants of about 0.1 to about 0.4. It is noted that sigma constants have not been measured for all of the preferred 8-substituents. However, the absence of such a measurement for a 8-substituent is not an indication that the 8-substituent is not among the preferred class of substituents.

We have found that 8-aminoguanosine and 8-benzyloxyguanosine are ineffective in modulating responses of animal cells and are more inhibitory to B cell activation than is Guo in which the 8-substituent is hydrogen. The amino group has a negative sigma constant (−0.16, Hine, p. 87, supra). The inhibitory effect of the 8-amino group is expected in view of the negative sigma constant for an amino group as a meta substituent. The inhibitory effect of the 8-benzyloxy group is surprising in view of the enhancing effect of the 8-methoxy group as discussed hereinafter and the positive sigma constants reported in Hine, p. 87, supra, for methoxy and phenoxy groups in the meta position. It is found, however, that the sample of 8-benzyloxyguanosine tested is impure, and it is believed that the inhibitory effect found relative to that of Guo is due to the presence of impurities.

The 8-substituted guanine derivatives useful herein are bonded 9-1' to an aldose having 5 or 6 carbon atoms in the aldose chain. The phrase "bonded 9-1'" is used herein to mean that the 9-position of the guanine is bonded to the 1' position of the aldose, as is usual for bonding in nucleoside chemistry. The useful aldoses are saccharides terminated by an aldehydo group, and have 5 or 6 carbons in the chain of carbon atoms comprising the saccharide backbone.

Suitable aldoses can be represented by the structural formula:

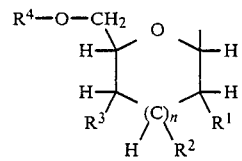

wherein
n is one or zero;
$R^1$ is hydrogen, hydroxy, methoxy, ethoxy or acetoxy;
$R^2$ is hydroxy, methoxy, ethoxy, acetoxy, amino, mono- or di-substituted $C_1$–$C_2$ amino, or acetamido;
$R^3$ is hydroxy, methoxy, ethoxy or acetoxy; and
$R^4$ is hydrogen, methyl, ethyl, or the acyl portion of a carboxylic acid having one to about 24 carbon atoms.

No stereochemical relationships between any groups bonded to the above ring structure are meant to be implied by the structure illustrated.

In preferred practice, n is zero, $R^1$ is hydrogen or hydroxy, $R^2$ is not present due to n being zero, $R^3$ is hydroxy and $R^4$ is hydrogen. Ribose, deoxyribose and their methyl and acetyl derivatives are particularly preferred aldoses. Ribose is especially preferred.

Exemplary of the other particularly preferred aldoses are ribose, 2',3',5'-tri-0-acetylribose, 2'-0-methylribose and deoxyribose. Exemplary of preferred aldoses are arabinose, tylose, lyxose, glucose, galactose, talose, allose, altrose, mannose, gulose and idose. Exemplary of acyl portions of carboxylic acids having one to about 24 carbon atoms are those derived from formic, acetic, propionic, hexanoic, decanoic, lauric, myristic, palmitic, stearic, oleic and arachidonic acids.

The 8-substituted guanine derivatives useful for present purposes herein are electrically neutral in charge. They are free from electrically charged functionality either on the guanine or aldose portions of the molecule, except for the nitrogens of the guanine moiety which can possess an electric charge in water or an aqueous environment due to protonation. Thus, phosphate derivatives such as 8-BrcGMP or 8-BrGMP which bear the electrically charged functionality of the phosphate group are excluded from the group of useful active ingredients. The positively charged 8-BrGuo derivatives such as the 7-methyl-8-bromoguonosinium ion, prepared by bromination of 7-methyl Guo following bromination procedures discussed hereinafter, however, were found to be unstable and therefore unsuitable for the purposes of this invention.

Physiologically tolerable carriers, dosages, specific compositions, routes of administration and the like for the useful cell response modulating compositions of this invention are discussed hereinafter.

Lymphocyte Activation

We unexpectedly found that per molecule taken up, 8-BrGuo is about 1.5 to about 2 orders of magnitude more effective as a B cell activator than is 8-BrcGMP, and that exogenous cGMP itself has insignificant mitogenic potential. See Goodman and Weigle, *Proc. Natl. Acad. Sci. U.S.A.*, 78:7604 (1981), incorporated herein by reference.

Induction Of Immunoglobulin Secretion

8-BrcGMP has a slight effect on inducing the maturation of precursor B cells to polyclonal immunoglobulin secretion. However, per molecule absorbed by the cells, 8-BrGuo is about 2 to about 2.5 orders of magnitude more biologically potent in both serum-free and 5% FCS-containing medium. The promotion of induced polyclonal immunoglobulin secretion is also dose-dependent in the presence and absence of serum. Guo and cGMP inhibit the polyclonal response of B cells to 8-BrGuo. See Goodman and Weigle, *J. Immunol.*, 128: 2399 (1982), incorporated herein by reference.

Other guanine derivatives, such as 8-oxoguanosine, 8-methoxyguanosine, 7-methyl-8-oxoguanosine, 8-MGuo and 8-thiomethylguanosine, in addition to 8-BrGuo, also induce immunoglobulin secretion in spleen cells, as shown in Table II.

TABLE II

Induction of Immunoglobulin Secretion in Spleen Cells by Guanine Derivatives

| Guanine Derivative | Immunoglobulin Secreting Cells/Culture | |
|---|---|---|
| | Control | Treated[a] |
| 8-oxo-Guo[b] | 7 | 320 |
| 8-methoxyGuo[c] | 7 | 85 |
| 7-met-8-oxo-Guo[d] | 7 | 800 |
| 8-MGuo[e] | 7 | 543 |
| 8-methylMGuo[f] | 7 | 462 |

[a]Cells cultured with a one millimolar concentration of guanine derivative, at $5 \times 10^6$ cells/milliliter, and assayed after three days of incubation.
[b]8-Oxoguanosine.
[c]8-Methoxyguanosine.
[d]7-Methyl-8-oxoguanosine.
[e]8-Mercaptoguanosine.
[f]8-Methylthioguanosine.

Resistance To Cell Metabolism

8-BrGuo is not metabolized by B cells, nor does it interfere with enzymatic processing of Guo. These findings demonstrate that 8-substituted guanine derivatives cannot be assumed to be used by cells like their unsubstituted congeners, or that they are metabolized similarly by the cell. See Goodman and Weigle, *J. Immunol.*, 129:2715 (1982), incorporated herein by reference.

The single cell suspensions of CBA/CaJ spleen cells used in these studies were prepared as described by Goodman et al., *J. Immunol.*, 121:1905 (1978). Erythrocytes were lysed in a solution of 0.83% ammonium chloride, and T lymphocytes were eliminated by treatment with a monoclonal anti-thy-1.2 antibody and complement following the procedure of Goodman and Weigle, *J. Exp. Med.*, 145:473 (1977). The resultant B cell populations were cultured under serum-free conditions in an RPMI 1640-based medium as detailed in Goodman et al. above.

Radiolabeled compounds were prepared, and thin layer chromatography of lymphocyte extracts were carried out in accordance with the respective procedures discussed in Goodman and Weigle, *Proc. Natl Acad. Sci. U.S.A.*, supra.

In Vitro Adjuvanticity

Figure 1:
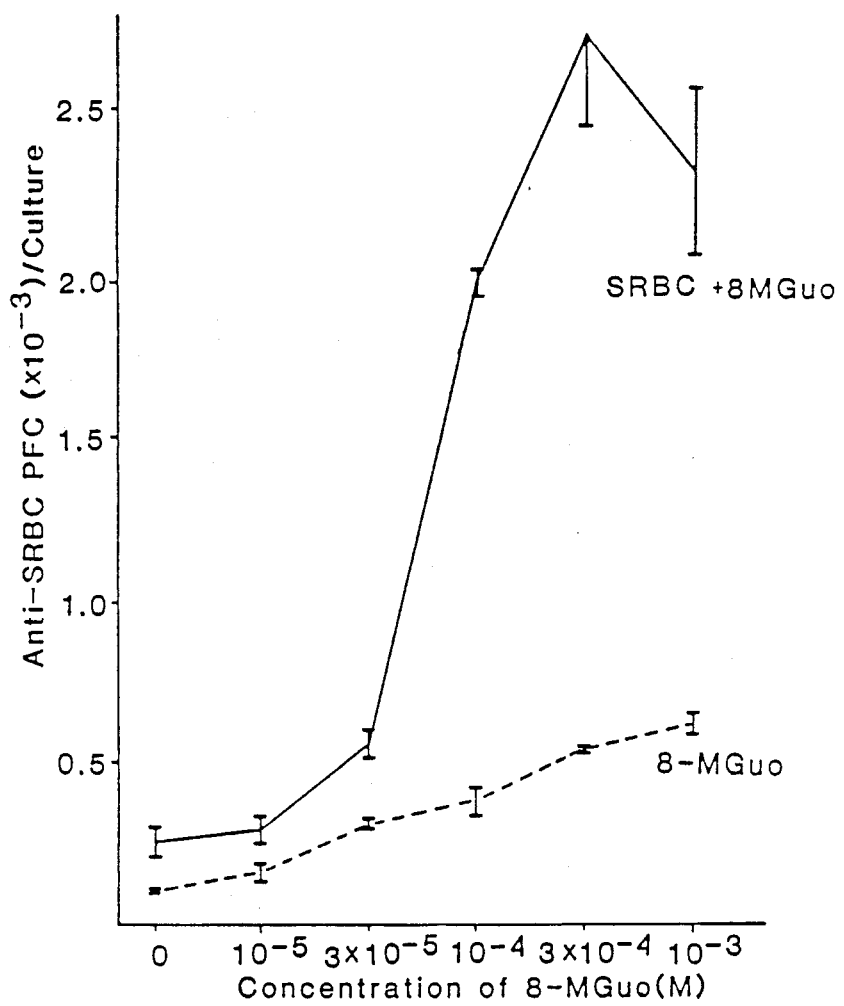
FIG. 1 illustrates enhancement of the primary antibody response by 8-MGuo. $10^7$ Viable CBA/CaJ spleen cells were cultured in the presence or absence of SRBC with incremental concentrations of 8-MGuo. Direct PFC to SRBC were determined after 4 days of culture. Results are expressed as the arithmetic mean of triplicate cultures ± standard error (S.E.).

FIG. 1 illustrates the effect of 8-MGuo as an adjuvant on the primary antibody response to SRBC evaluated in vitro. At optimal concentrations, compositions containing this nucleoside derivative enhanced the response to SRBC by more than an order of magnitude. The effect is dose dependent, with its greatest effect in the range of 0.3 millimolar 8-BrGuo for the culture studied. Enhancement of the antibody response (2725 PFC) could not be accounted for by the additive effects of the specific response to SRBC (253 PFC) and the polyclonal response to 8-MGuo (540 PFC).

Figure 2:
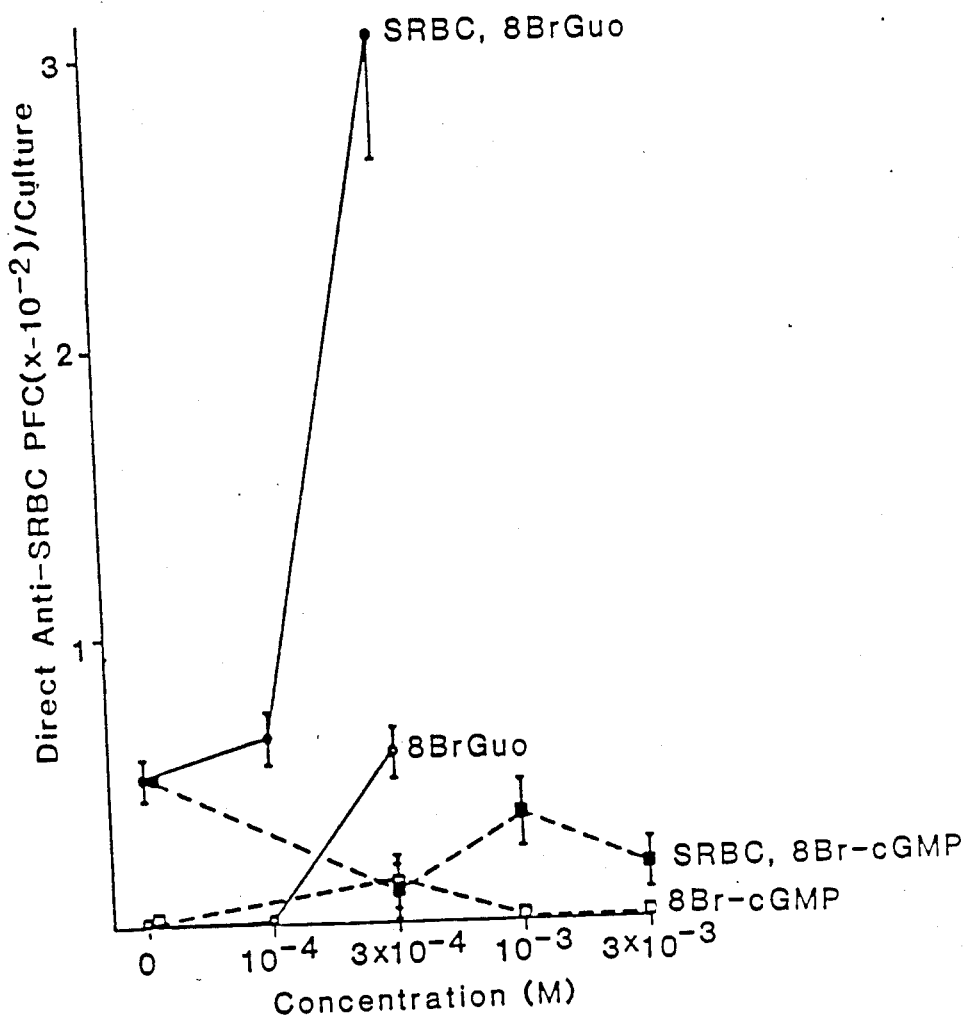
FIG. 2 illustrates enhancement of the primary antibody response by 8-BrGuo versus 8-BrcGMP. $10^7$ Viable CBA/CaJ spleen cells were cultured in the presence or absence of SRBC with incremental concentrations of 8-BrGuo or 8-BrcGMP. Direct PFC to SRBC were determined after 4 days of culture. Results are expressed as in FIG. 1.

By comparison, 8-BrcGMP did not augment the primary response to SRBC (FIG. 2) even at concentrations as high as 3 millimolar. 8-BrGuo, in contrast, markedly enhanced the antibody response to this antigen. For purposes of comparison, the data also show the polyclonal responses on Day 4 (i.e., without antigen), illustrating again that the observed adjuvant effect was not due to polyclonal activation of B cells.

Figure 3:
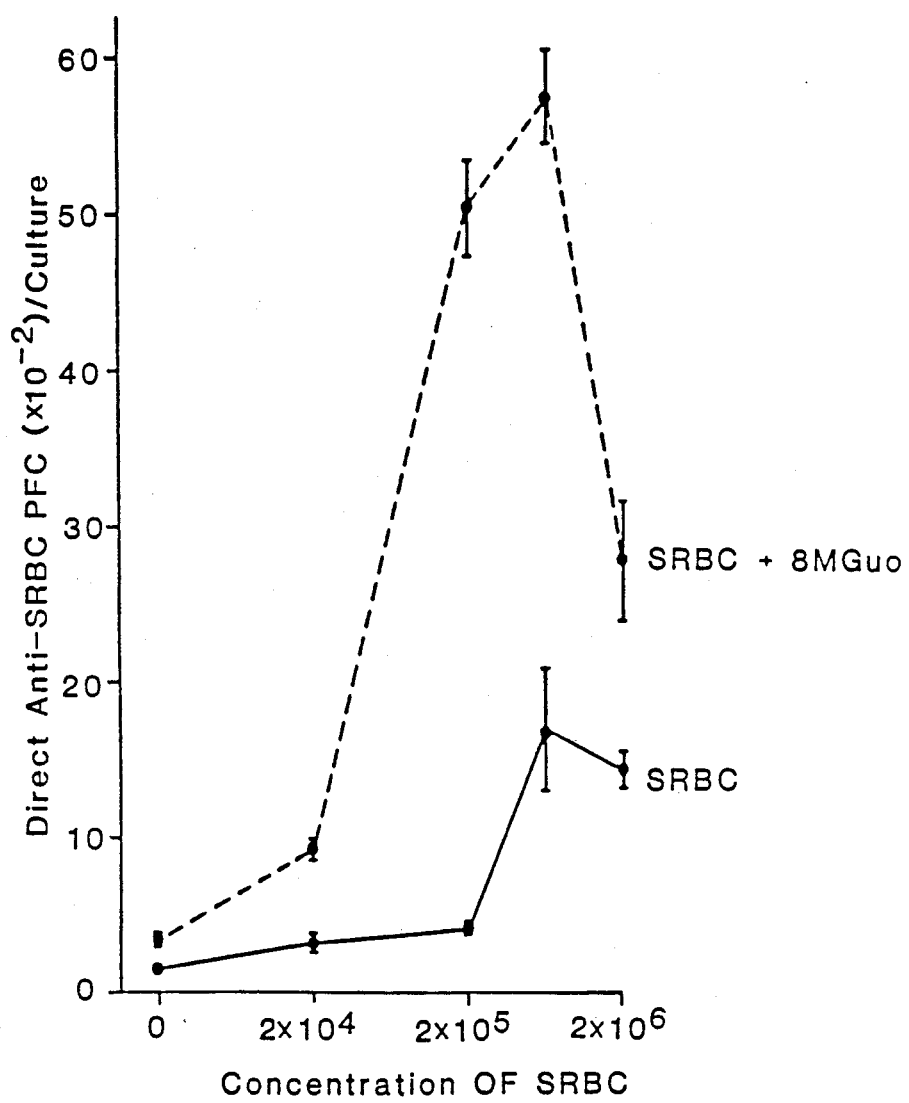
FIG. 3 illustrates enhancement of the secondary IgM antibody response by 8-MGuo. $10^7$ Viable SRBC-primed CBA/CaJ spleen cells were cultured in the presence or absence of 0.3mM 8-MGuo with incremental concentrations of SRBC. Results are expressed as in FIG. 1.
Figure 4:
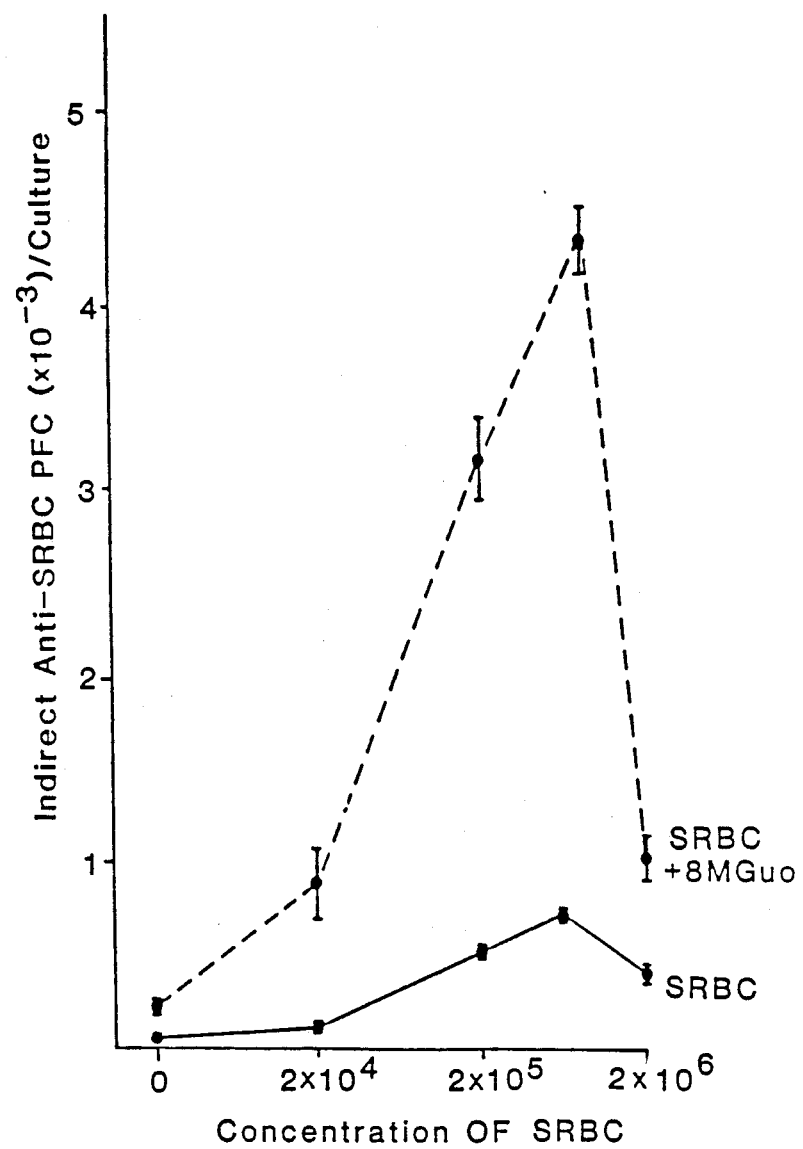
FIG. 4 illustrates enhancement of the secondary IgG antibody response by 8-MGuo. $10^7$ Viable SRBC-primed CBA/CaJ spleen cells were cultured in the presence or absence of 0.3mM 8-MGuo with incremental concentrations of SRBC. Indirect PFC to SRBC were determined after 4 or 5 days of culture. Results are expressed as in FIG. 1.

The adjuvant effect of compositions containing 8-MGuo exerted on antigen-experienced as well as naive cells is also of interest. The effects of compositions containing 8-MGuo on the secondary IgM and IgG responses to SRBC are illustrated in FIGS. 3 and 4.

Both responses were markedly enhanced by contacting the cells with compositions containing the nucleoside derivative. The IgM (direct) response was enhanced by a factor of 12.2 and the IgG (indirect) response was enhanced by a factor of 7.2. This adjuvant effect was dependent upon the concentration of antigen added to culture. The nucleoside concentration that elicited the observed peak level secondary responses was about the same as the optimal dose for the primary IgM response (0.3 millimolar) for the culture examined.

The effectiveness of the compositions of this invention on cells of human origin is demonstrated by the adjuvanticity of 8-MGuo on human peripheral blood lymphocytes in the presence of a specific antigen; i.e. SRBC. These results are illustrated in FIG. 32. As can be seen from examination of FIG. 32, contacting human peripheral blood lymphocytes with a composition of this invention containing 8-MGuo in the presence of a specific antigen provided about a 6-fold enhancement of the primary response to the antigen as measured by direct anti-SRBC PFC.

Figure 5:
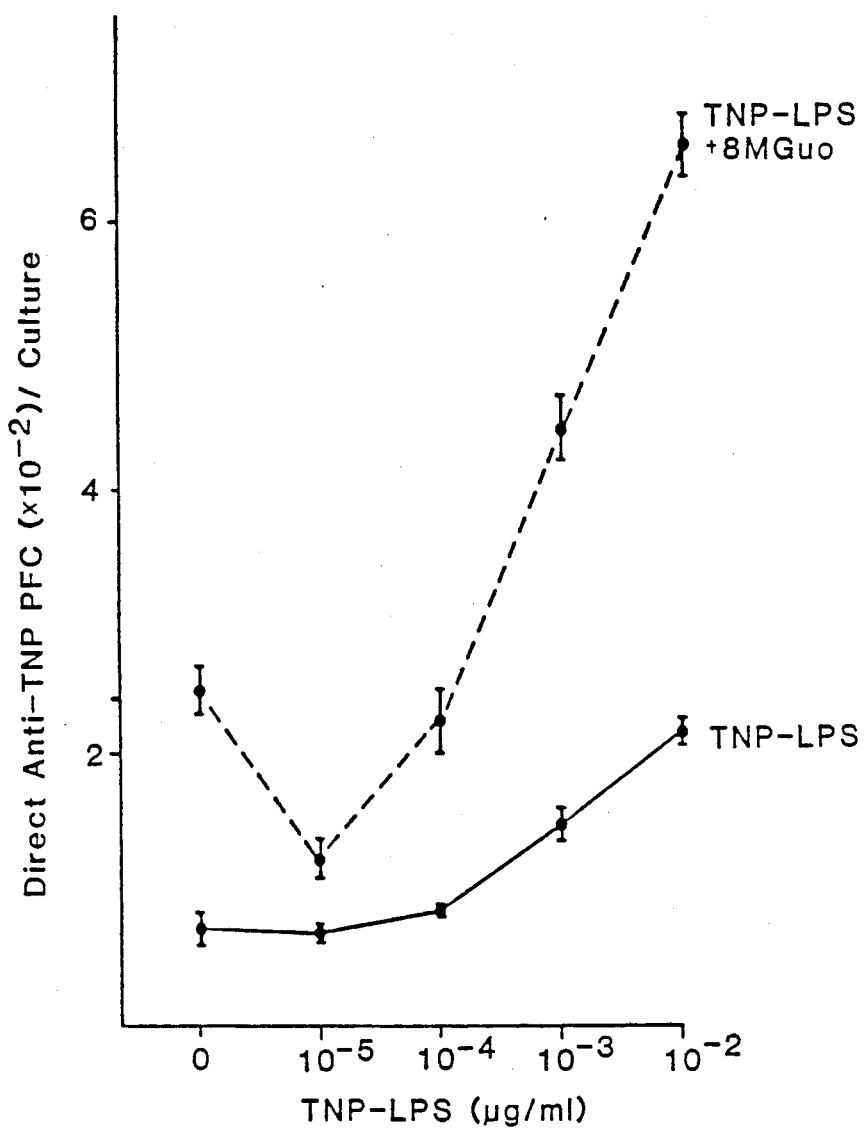
FIG. 5 illustrates enhancement of the antibody response to a TI-1 antigen by 8-MGuo. $10^7$ Viable CBA/CaJ spleen cells were cultured in the presence or absence of 0.3mM 8-MGuo with incremental concentration of TNP-LPS. Direct PFC to TNP were determined after 3 days of culture. Results are expressed as in FIG. 1.
Figure 6:
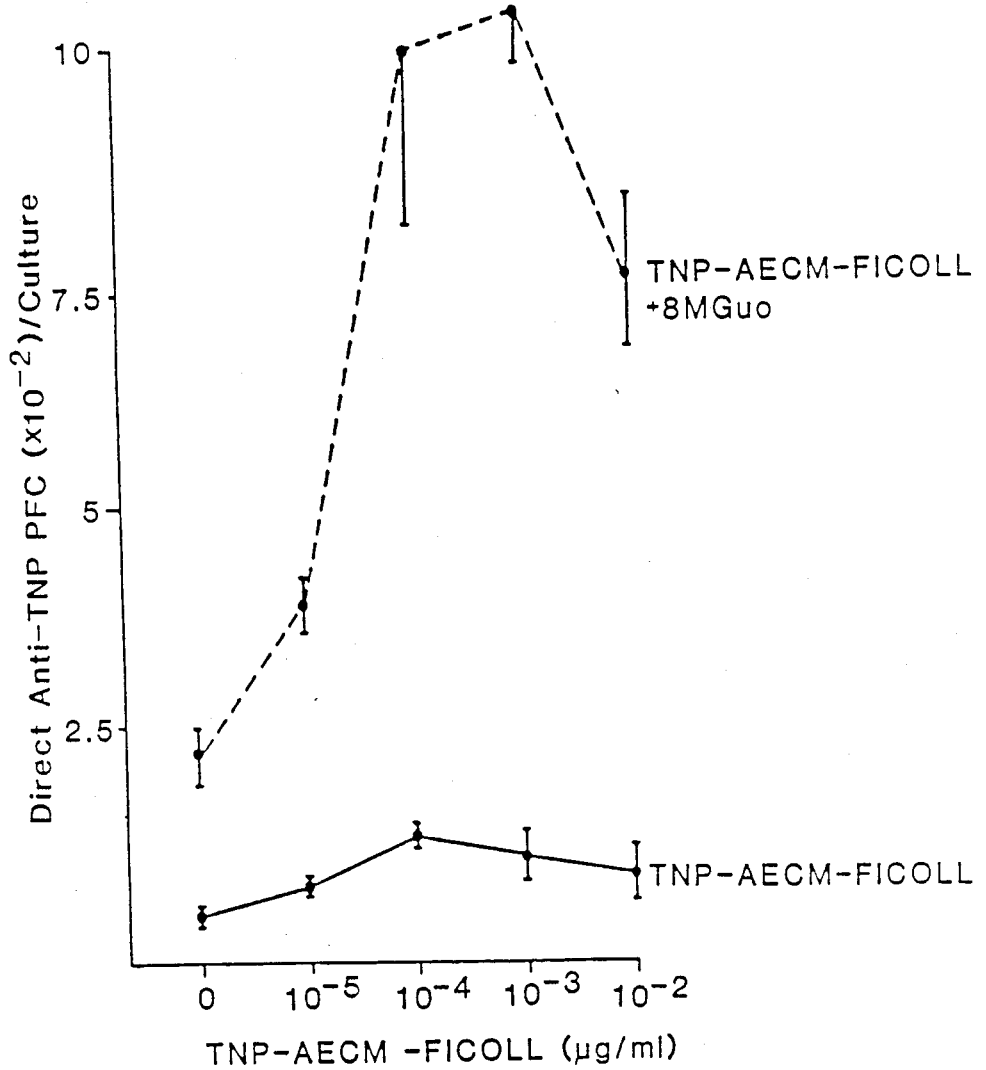
FIG. 6 illustrates enhancement of the antibody response to a TI-2 antigen by 8-MGuo. $10^7$ Viable CBA/CaJ spleen cells were cultured in the presence or absence of 0.3mM 8-MGuo with incremental concentrations of TNP-AECM-ficoll. Direct PFC to TNP were determined after 3 days of culture. Results are expressed as in FIG. 1.

The ability to enhance antibody responses to T-independent antigens was also examined to determine whether the adjuvant effect of 8-MGuo is exerted primarily upon T helper cells or upon the antibody-producing B cell. At antigen doses below those that induce polyclonal activation, the response to TNP-LPS, an antigen of the TI-1 class, was enhanced about 3 fold, as illustrated in FIG. 5. In contrast, the response to TNP-AECM-ficoll, an antigen of the TI-2 class, was augmented 8.9 times as can be seen in FIG. 6.

Figure 7:
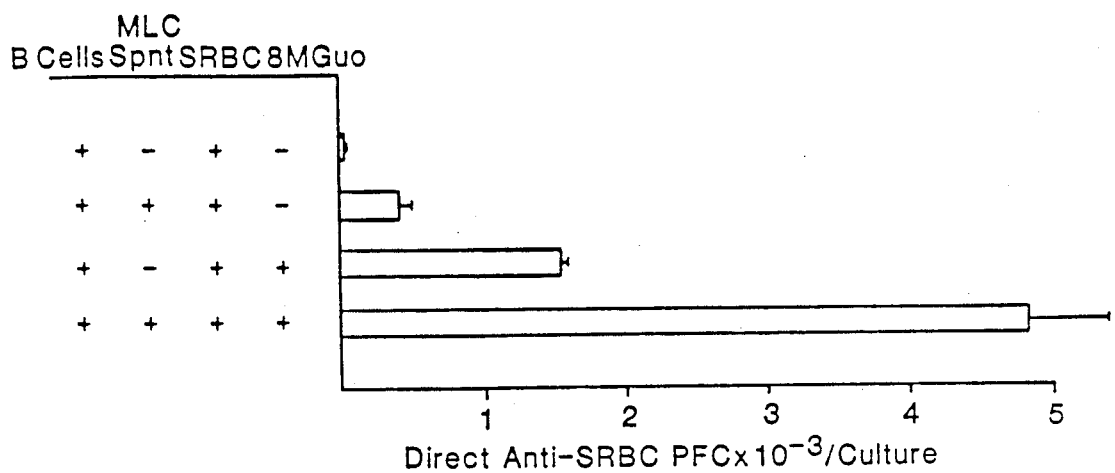
FIG. 7 illustrates enhancement of the antibody response in the absence of intact T cells. $5\times10^6$ Viable CBA/CaJ B cells were cultured with SRBC in the presence or absence of 5% MLC supernatant and/or 0.3mM 8-MGuo. Direct PFC to SRBC were determined after 4 days of culture. Results are expressed as in FIG. 1.

Studies in which intact T cells were replaced by supernatant fluids from mixed lymphocyte cultures (MLC) that contained soluble T helper activity further determined if the cellular target of the enhancing effects of 8-MGuo was the antibody producing cell or the T cell. See Britton, *Scand. J. Immunol.*, 1:89 (1972). FIG. 7 shows that the antibody response generated by B cells in the presence of antigen and MLC supernate was increased by more than an order of magnitude when a composition containing 8-MGuo was added to contact the cells. Moreover, the data of FIG. 7 indicate that this nucleoside can substitute for T helper cells in the absence of an MLC supernate.

The nature of the signals provided by the supernatant factor and the nucleoside-containing composition appear to be distinct, inasmuch as a marked synergy was observed when both were added to culture simultaneously. Thus, adjuvant effects of 8-MGuo do not appear to be mediated by intact T cells, but can be exerted directly upon the responsive B cell or upon the antigen-presenting cell.

Figure 8:
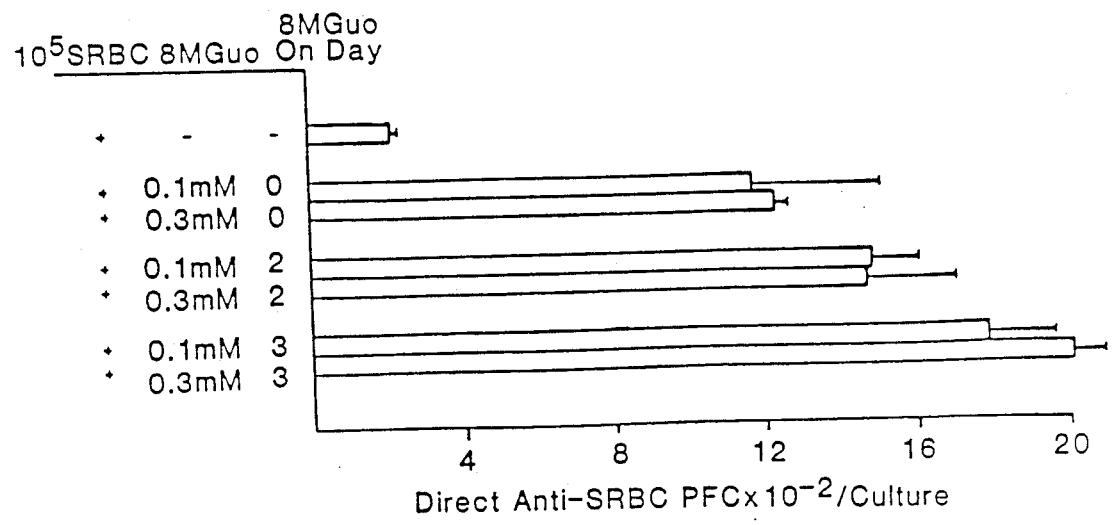
FIG. 8 illustrates kinetic profile for addition of 8-MGuo. $10^7$ Viable CBA/CaJ spleen cells were cultured in the presence or absence of SRBC with either 0.1 mM or 0.3 mM 8-MGuo added on sequential days of culture. Direct PFC to SRBC were determined after 4 days of culture. Results are expressed as in FIG. 1.

It is known that certain adjuvants, such as LPS, lose their enhancing capacity if added to culture a day or more after antigen. See Ortiz-Ortiz and Jaroslow, *Immunology*, 19:38 (1970). Sensitivity to the adjuvant effect of 8-MGuo, however, was not limited to the early part of the incubation period as can be seen from FIG. 8. Marked enhancement of the underlying antibody response occurred even when cultures were supplemented with the nucleoside derivative on Day 3 of a 4-day culture period. It therefore appears that the adjuvant action was exerted on events occurring relatively late in the response.

One of the important potential uses for an adjuvant is the amelioration of immunodeficiency states. To determine if 8-BrGuo is of value in this regard, its effect on the antibody response of immunodeficient (CBA/N×-CBA/CaJ)F$_1$ mice was evaluated.

Figure 9:
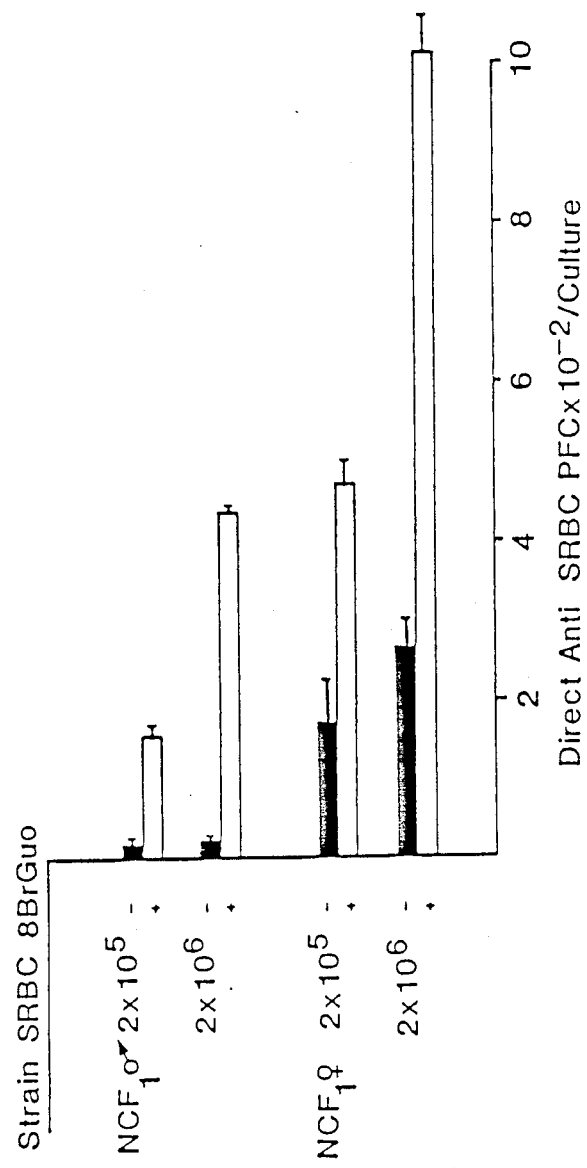
FIG. 9 illustrates augmentation of the antibody response of immunodeficient mice by 8-BrGuo. $10^7$ Viable spleen cells from male or female $NCF_1$ mice were cultured in the presence of absence of 0.3 mM 8-BrGuo with either $2\times10^5$ or $2\times10^6$ SRBC. Direct PFC to SRBC were determined after 4 days of culture. Results are expressed as in FIG. 1.

The underlying antibody response to a thymus-dependent antigen was observed to be very low in the deficient (male) animals as compared to the control (female) animals as shown in FIG. 9, and as reported by others. See, for example, Janeway and Barthold, *J. Immunol.*, 115:898 (1975). However, supplementation of cultures with compositions containing the 8-substituted guanine derivative, 8-BrGuo, as active ingredient resulted in marked enhancement (about 20-fold) of the response generated by cultures containing immunodeficient cells. This enhancement raised the response above the level achieved by normal cells alone, and was in the range of the enhanced response produced by normal cells in the presence of 8-BrGuo and low doses of antigen.

The foregoing results indicate that the composition of this invention, when contacted with cells, provides a distinct second message that is not dependent upon the presence of a helper T cell signal. The above results also illustrate a specific, dose-dependent augmentation of antibody response at a concentration about one-half an order of magnitude lower than that which induces maximal mitogenesis and polyclonal immunoglobulin secretion. (See Goodman and Weigle, *Proc. Natl. Acad. Sci. U.S.A.* and *J. Immunol.*, 128:2399, supra.)

It is to be noted that while the compositions and methods of this invention are useful in enhancing mitogenesis, polyclonal responses and adjuvanticity as already noted, those three properties are thought to result from at least two different pathways wherein mitogenesis and a polyclonal response often are co-incident results while adjuvanticity results frequently differ. See for example Goodman et al., *J. Exp. Med.*, 147:800 (1978); McIntire et al., *J. Immunol.*, 117:674 (1976); and Hoffman et al., *J. Exp. Med.*, 146 (1977).

The dissociation of the above three properties can be further illustrated by examination of FIG. 31. It is there seen that normal (CBA/CaJ) mice respond to the pleiotropic effects of 8-MGuo in assays for the three properties. However, the abnormal mouse strain (SJL) fails to respond to 8-MGuo with proliferation or polyclonal (non-specific) antibody response, but does respond in the presence of a specific antigen (SRBC).

In a separate study using SJL B cells in the presence and absence of SRBC as antigen and 8-MGuo to provide a T-like signal, mitogenesis and TRF-like activity were both found to exhibit dose dependence upon the 8-MGuo concentration. However, mitogenesis only increased by a factor of about 4- to about 5-fold, while the TRF-like activity increased by about 140-fold and then dropped to about a 40-fold increase over the same concentration range ($10^{-5}$ to $10^{-3}$ molar) of 8-MGuo while the concentraion of SRBC was held constant at 0.01 percent.

In addition, the dose depending mitogenesis observed is seen only in the presence of specific antigens.

It is further noted that mitogenesis continued to increase over the dose range of 8-MGuo studied, while the TRF-like activity peaked in that concentration range. The results further indicate that the mitogenic activity does not account for the TRF-like activity observed.

While immune responses were observed to be enhanced at all doses of antigen, the degree of enhancement was usually greatest at optimal or near optimal antigen concentrations. Our results showed that adjuvanticity of either 8-MGuo or 8-BrGuo was synergistic with antigen and not just due to the sum of antigen specific and polyclonal (nonspecific) responses.

Enhancement of antibody production by 8-MGuo involves not only naive, antigen-inexperienced B cells, but also antigen-experienced or memory B cells. Thus, the primary IgM as well as the secondary IgM and IgG responses were augmented by contacting the culture with a composition containing an effective amount of 8-MGuo as active ingredient.

8-MGuo is thought to enhance the primary humoral immune response by acting directly upon the B cell and/or the antigen-presenting cell. Thus, use of this nucleoside derivative enhanced the antibody response mounted against T-independent antigens, responses that involve B cells and antigen-presenting cells. In addition, compositions containing 8-MGuo exert their adjuvant effect in cultures initiated in the absence of intact, functional T cells. A replacement of T cells with T cell helper activity contained in MCL supernates did not diminish the ability of 8-MGuo to augment the antibody response. Still further, the synergy observed between the soluble T cell signal and the guanine derivative-containing composition indicates that the signal supplied by each is qualitatively distinct. This synergy was observed over a range of supernate concentrations, indicating that the guanosine derivative was not simply providing more of a MLC-like signal. A comparable degree of synergy can be observed when such B cell cultures are supplemented with T cells rather than with MLC supernates (which are in fact T cell derived), in the presence of antigen and contacted with a guanidine derivative-containing composition of this invention.

T cell-mediated effects of the adjuvanticity of 8-MGuo are not ruled out by the observation of T-independence for that adjuvanticity, i.e., the existance of a T cell-independent facet does not bear upon the existance of a T cell-dependent phase. Thus, more substantial enhancement by compositions containing the guanosine derivative was observed under conditions of stimulation with low doses of T-dependent and T-independent type 2 antigens (T cell dependent situations) than with T-independent type 1 antigens (more completely T cell-independent), which suggests the presence of a T cell-dependent component.

A test of an adjuvant's value is its ability to restore the immune response of immunodeficient subjects. Thus, CBA/N mice were used as a murine model of X chromosome-linked (X-linked) primary B cell immunodeficiency. This strain is thought to be deficient in the functional activity of a subpopulation of mature B lymphocytes bearing the Lyb 3/5/7 antigens. See Huber et al., *J. Exp. Med.*, 145:1 (1977); Ahmed et al., *J. Exp. Med.*, 145:101 (1977); and Subbarao, *J. Immunol.*, 122:2279 (1979) The inability of NCF$_1$ male mice bearing this defect to respond normally to T-dependent antigen (Janeway and Barthold, supra) was corrected to levels above those of control animals by supplementation of cultures with 8-BrGuo.

Particulars of the above-discussed results are found in Materials and Methods Section A, hereinafter. [See Goodman and Weigle, *J. Immunol.* 130:2580 (1983)].

The results discussed hereinabove in this Section illustrate that a T cell-like signal is transmitted to B cells by contact of those B cells in the presence of antigen with a composition of this invention, and that that signal synergizes with certain other signals derived from T cells or their products.

Ability of Beta-Interferon and 8-MGuo To Promote Increased T-Cell-Like Inductive Signaling in B Cells In the course of studies on the effects of C8-derivatized nucleosides on B lymphocyte function, a relationship regarding the ability of the nucleosides to transmit a T cell-like signal to B cells in the presence of antigen was observed. Consequently, the T cell-like inductive effects of 8-MGuo on B cells and antigen in the presence of a form of supernate containing a variety of T cell- and macrophage-derived cytokines were studied.

Figure 23:
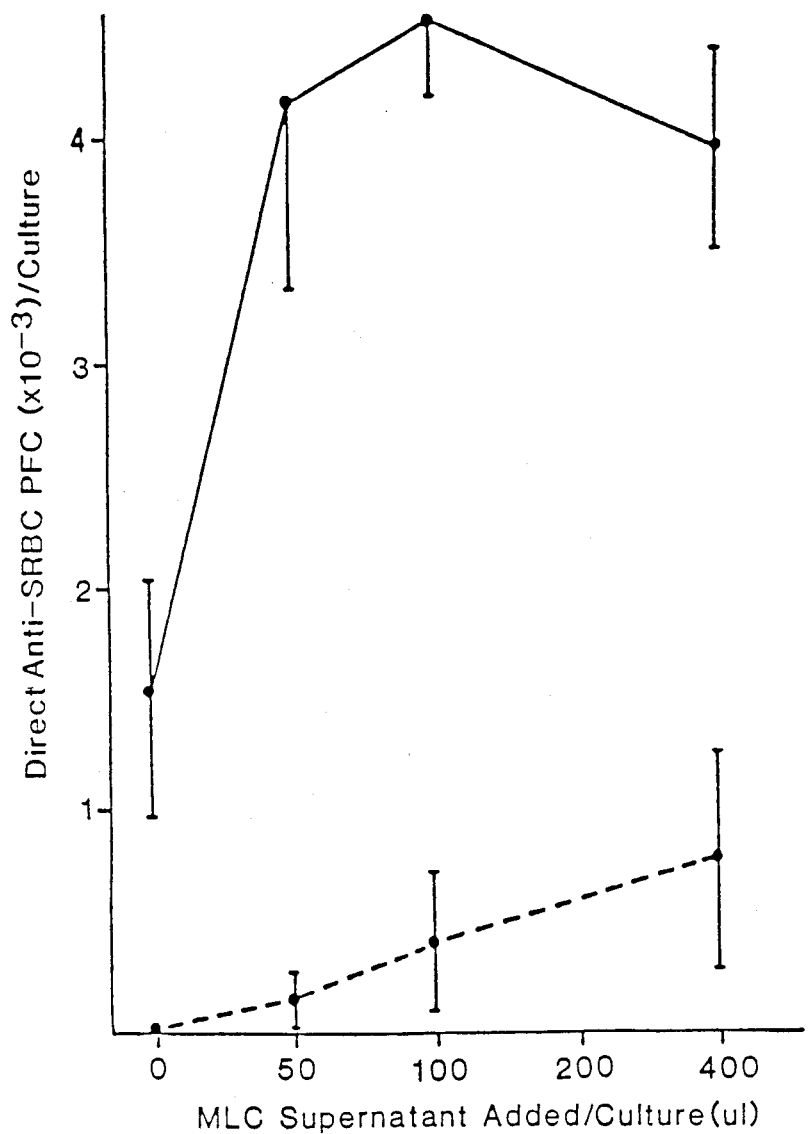
FIG. 23 illustrates the synergy between MLC supernatant and 8-MGuo. $5 \times 10^6$ Viable CBA/CaJ splenic B cells were cultured with or without SRBC in the presence of incremental quantities of MLC supernatant. One set of cultures (—) was made $3 \times 10^{-4}$M with 8-MGuo, the other (----) was not. Direct PFC to SRBC were determined after 4 days. Results are expressed as the arithmetic mean of the difference of triplicate experimental and control (control=88±3 PFC) cultures ± S.E.

The cytokines were obtained as cell-free supernates from mixed lymphocyte cultures between CBA/CaJ and (C57Bl/6J × DBA/2)F$_1$ mice. Such supernates contain interleukin-1, interleukin-2, B cell growth factors, T cell replacing factors, and interferons, among others. A co-culture of B cells in the presence of antigen and these supernates along with 8-MGuo resulted in a synergistic response (antigen-specific antibody-secreting cells) as seen in FIG. 23, relative to that seen with B cells and antigen in the presence of 8-MGuo or supernate alone.

Studies are in progress to identify the cytokine(s) responsible for synergistically amplifying the antigen-specific response of purified B cells in the presence of 8-MGuo. The interferons, in particular, appear promising in this regard, and initial results utilizing beta-interferon are shown in Table III, below.

TABLE III

Ability of Beta-Interferon and 8-MGuo Alone and Together To Promote Increased T Cell-Like Inductive Signaling in B Cells[a]

| SRBC[b] | 8-MGuo[b] | Beta-IFN[b] (Units/ml) | PFC[c] |
|---|---|---|---|
| − | − | − | 38 ± 7 |
| + | − | − | 63 + 20 |
| − | + | − | 575 ± 31 |
| + | + | − | 2404 ± 283 |
| + | − | 1 | 50 ± 5 |
| + | + | 1 | 3104 ± 56 |
| + | − | 10 | 103 ± 28 |
| + | + | 10 | 3417 ± 227 |
| + | − | 100 | 213 ± 16 |
| + | + | 100 | 3675 ± 0 |
| + | − | 1000 | 411 ± 45 |
| + | + | 1000 | 6175 ± 628 |
| − | − | 1000 | 57 ± 7 |

[a]Triplicate cultures were prepared containing 5 × 10$^6$ CBA/CaJ B cells per milliliter (ml) along with 0.01% SRBC, 3 × 10$^{-4}$ molar 8-MGuo and/or the units shown of Beta-IFN as is indicated in the Table. Each culture was fed once daily as described in Mishell and Dutton, J. Exp. Med., 126:423 (1967). PFC determination was done on the fourth day of culture.
[b]The presence of the sheep red blood cell (SRBC) antigen, 8-MGuo and/or beta-interferon (Beta-IFN) is indicated by a "+" sign, while the absence of any of the above is indicated by a "−" sign.
[c]Plaque forming cells after four days of culture; determined as per FIG. 1.

As the data in Table III indicate, murine beta-interferon is capable of providing a T cell-like inductive signal for B cells and antigen, as is 8-MGuo. However, in the presence of both 8-MGuo and beta-interferon, a definite synergy of the response elicited is observed. The enhanced immune response observed in vitro by contacting cells such as B cells in the presence of antigen with a composition of this invention containing about $1 \times 10^{-5}$ to about $1 \times 10^{-3}$ molar 8-substituted guanosine derivative can be improved synergistically when that composition also contains about $1 \times 10^3$ to $5 \times 10^9$ units/liter of interferon, such as beta-interferon. More preferably, in vitro, the concentration of interferon is about $1 \times 10^4$ to about $5 \times 10^6$ units/liter.

For in vivo applications in humans, the interferon dosage should be about $1 \times 10^3$ to about $5 \times 10^9$ units per day in single or repeated doses, and more preferably about $1 \times 10^4$ to about $5 \times 10^6$ units per day. For animal applications, dosages are proportional to those of humans, based upon the animals body weight. The effective dosages of 8-substituted guanine derivatives of this application such as 8-MGuo for use in conjunction with interferon such as beta-interferon are discussed hereinafter. Those dosages are typically in the range of about 1 to about 1000 milligrams per kilograms of body weight of the human or other animal being treated. Studies utilizing alpha- and gamma-interferons, as well as other cytokines, are currently in progress, and it is believed will exhibit a similar synergy.

Figure 10:
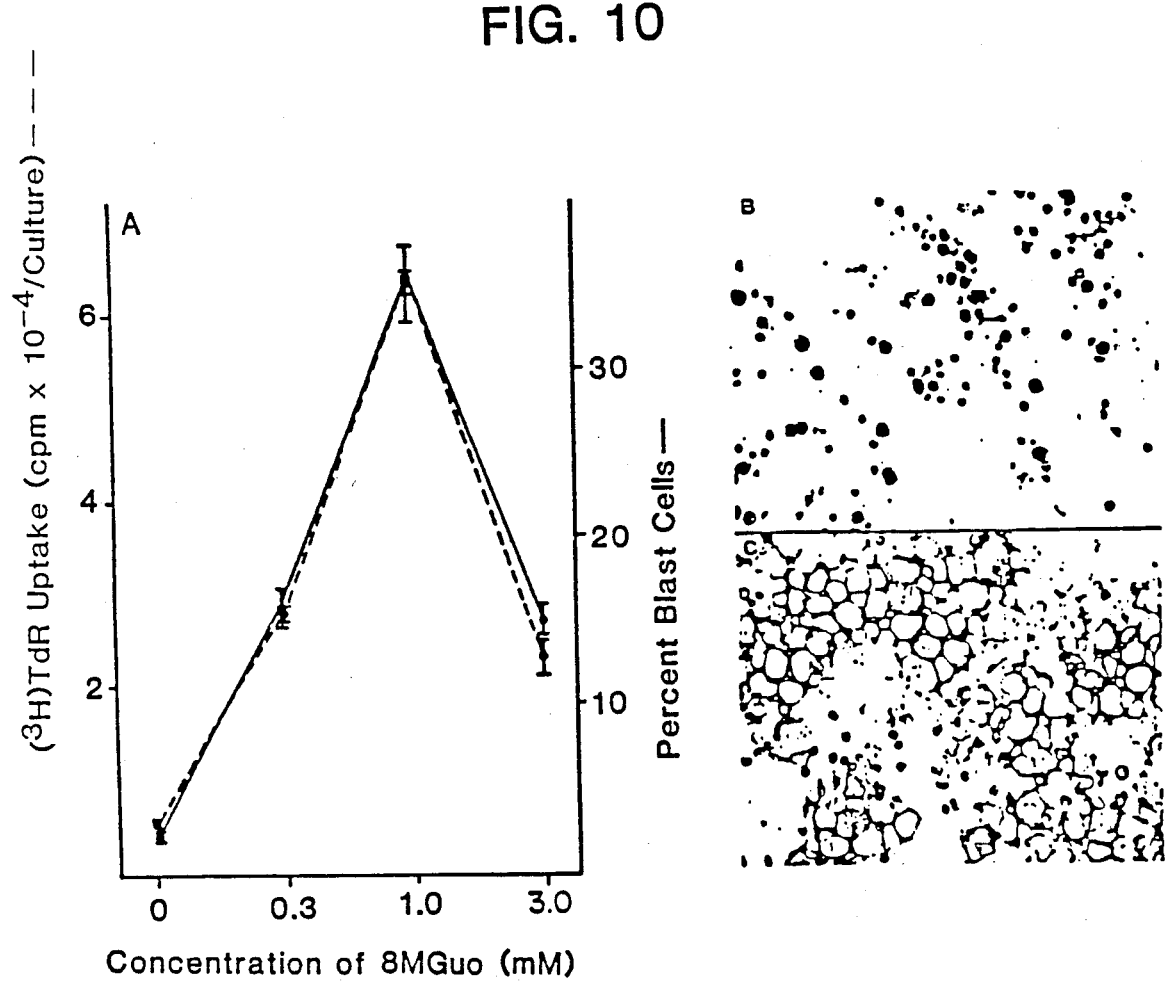
FIG. 10 illustrates ability of 8-MGuo to induce blast transformation. A. $4 \times 10^5$ Viable CBA/CaJ spleen cells were cultured with incremental concentrations of 8-MGuo for 2 days and evaluated for [$^3$H] TdR uptake or blastogenesis as described under Materials and Methods hereinbelow. Results are the mean of 5 (TdR uptake) or 4 (blastogenesis) replicate cultures ± S.E. B. Photomicrograph of unstimulated cells. C. Photomicrograph of cells incubated with 1 mM 8-MGuo for 2 days.

Characterization Of Lymphocyte Subpopulations Activated By An 8-Sulfidoguanine Derivative FIG. 10 illustrates results of incubation of spleen cells from CBA/CaJ mice incubated under serum-free conditions with compositions containing incremental concentrations of 8-MGuo. The graph shows resultant [$^3$H]TdR uptake and blast formation measured at two days of culture wherein the peak values were normalized. Representative fields of unstimulated and stimulated cells are seen in FIGS. 10B and 10C, respectively. The results illustrated in FIGS. 10A and 10C show that compositions containing the 8-sulfido substituted guanine derivative induced lymphocyte activation (as an indicator for proliferation) in a dose-dependent manner.

Spleen cells from congenitally athymic (nu/nu) C57BL/6J mice and from their heterozygous (nu/+) littermates were cultured in the presence of compositions containing incremental doses of 8-MGuo in serum-free medium. The response to the known T lymphocyte mitogen, Con A, was elicited to control for T cell contamination 8-MGuo evoked a [$^3$H]TdR uptake dose-response profile parallel to that seen for cultures of CBA/CaJ mice in both the C57BL/6J nude mouse and its heterozygous littermate, as can be seen from FIG. 11. That functional T cells did not contaminate these populations is indicated by the lack of stimulation induced by Con A in nu/nu cultures. This is shown on the right side of FIG. 11.

Figure 12:
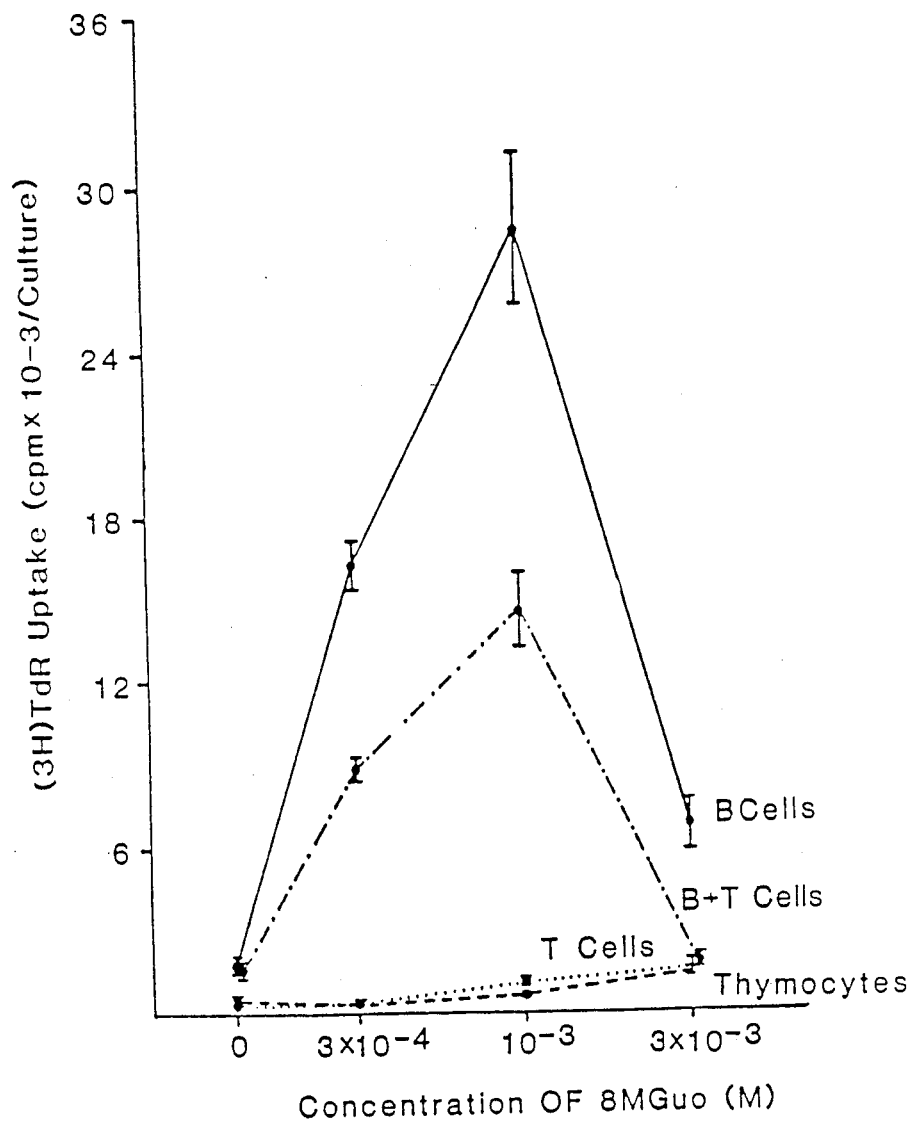
FIG. 12 illustrates the ability of 8-MGuo to activate B-enriched and T-enriched lymphocyte populations. $4 \times 10^5$ Viable CBA/CaJ thymocytes (----), splenic B cells (----), splenic T cells (....), or a 1:1 mixture of splenic B and T cells (-.-), were cultured with incremental concentrations of 8-MGuo for 2 days. Results are presented as in FIG. 11. B cells were capable of only 4% of the Con A response of unseparated cells, and T cells generated only 5.9% of the LPS response of unseparated cells.

Results of culturing CBA/CaJ thymocytes, spleen cells enriched for B cells, and T cells cultured under serum-containing conditions are illustrated in FIG. 12. The plots in FIG. 12 illustrate that B lymphocytes mounted a vigorous proliferative response to 8-MGuo while neither thymocytes nor splenic T cells showed a significant response. However, both thymocytes and splenic T cells were observed to mount strong responses to the T cell mitogen Con A.

The cell surface phenotype of 8-MGuo responsive cells was determined using splenic lymphocytes depleted of cells bearing various surface markers as described more specifically in Materials and Methods Spleen cells separated into FcR+ and FcR− populations by the EA-rosetting technique demonstrated that whereas FcR− cells were virtually unreactive toward 8-MGuo, FcR+ cells responded well (Table IV, C). Separation of spleen cells into populations bearing or lacking receptors for complement (i.e., C3) was accomplished by EAC-rosetting. Populations depleted of CR+ cells exhibited a small but significant response to 8-MGuo. The CR+ subset was observed to be highly responsive to compositions containing this nucleoside derivatives (Table IV, D).

Reactivity to 8-MGuo was evaluated in the CBA/N immunodeficiency model using the mice discussed hereinbefore for that pupose. Here, incubation of compositions containing 8-MGuo with cells of $NCF_1$ female mice resulted in a strong response. Only a modest response was observed upon culture with cells from $NCF_1$ male mice (Table IV, E).

TABLE IV

| | Surface Phenotype of 8-MGuo-Responsive Cells | | | |
|---|---|---|---|---|
| | ($[^3H]$TdR uptake, cpm/culture) Mitogen Added: | | | |
| Cell Population | Medium | 8-MGuo (1 mM) | LPS (100 μg/ml) | Con A (1 μg/ml) |
| A. | | | | |
| normal spleen | 8,800 ± 120 | 101,700 ± 1,100 | 124,700 ± 2,900 | 275,500 ± 3,400 |
| M - negative[a] | 2,500 ± 340 | 5,600 ± 600 | 7,500 ± 500 | 310,200 ± 8,200 |
| B. | | | | |
| normal spleen | 5,200 ± 500 | 76,900 ± 2,400 | 96,400 ± 2,200 | 62,200 ± 1,200 |
| D - negative[b] | 2,900 ± 300 | 23,500 ± 1,300 | 20,200 ± 1,000 | 62,200 ± 4,300 |
| C. | | | | |
| FcR+[c] | 5,500 ± 600 | 26,100 ± 1,200 | — — | — — |
| FcR− | 2,300 ± 900 | 3,500 ± 300 | — — | — — |
| D. | | | | |
| CR+[d] | 3,800 ± 100 | 78,800 ± 900 | — — | — — |
| CR− | 1,600 ± 100 | 13,600 ± 300 | — — | — — |
| E. | | | | |
| $NCF_1$ (female)[e] | 11,000 ± 1,100 | 97,800 ± 2,900 | — — | — — |
| $NCF_1$ (male) | 2,900 ± 700 | 10,600 ± 500 | — — | — — |

[a] $4 \times 10^5$ Viable CBA/CaJ spleen cells, after 2 pannings on petri dishes coated with either 5% FCS-containing medium or anti-IgM antibodies, were cultured with 8-MGuo, LPS, or Con A for 2 days.
[b] $4 \times 10^5$ Viable CBA/CaJ spleen cells, after 2 pannings on petri dishes coated with either 5% FCS-containing medium or anti-IgD antibodies, were cultured with 8-MGuo, LPS, or Con A for 2 days.
[c] $4 \times 10^5$ Viable CBA/CaJ spleen cells isolated from either the FcR+ fraction (pellet) or FcR− fraction (interface) of EA-rosetted cells, were cultured with or without 8-MGuo for 2 days.
[d] $4 \times 10^5$ Viable CBA/CaJ spleen cells, isolated from the CR+ fraction (pellet) or from the CR− fraction (interface) of EAC-rosetted cells, were cultured with or without 8-MGuo for 2 days.
[e] $4 \times 10^5$ Viable spleen cells from either $NCF_1$ female or male mice were cultured with or without 8-MGuo for 2 days.

Section B. When surface IgM heavy chain-bearing cells were removed followed by re-depletion of the same cells, the resultant-depleted population was unresponsive to 8-MGuo or LPS, but was fully reactive to the T cell mitogen, Con A (Table IV, A, below). Applying the same technique to cells bearing a surface IgD heavy chain, using the monoclonal product of the 10-4.22 cell line, it was found that populations depleted of surface IgD heavy chain-bearing cells were capable of a small, but significant response to 8-MGuo (Table IV, B). The non-adhered population was observed to be modestly responsive to LPS, but retained full reactivity for Con A.

CBA/CaJ ($H-2^k$) and BALB/c ($H-2^d$) spleen cells were incubated with various dilutions of A.TH anti-A.TL antiserum (anti-$Ia^k$) in the presence of or absence of compositions containing optimal concentrations of 8-MGuo to determine whether responses to 8-MGuo were susceptible to inhibition by anti-Ia antibodies. As can be seen from examination of Table V, below, high concentrations of antiserum exhibited nonspecific inhibitory effects, while specific inhibition was observed at lower dilutions. The observed incomplete inhibition suggests that a significant number of 8-MGuo-reactive cells either lack surface Ia or bear such low concentrations that cellular activity is not inhibited by binding of antibody.

TABLE V

| | Effect of Anti-Ia Antibodies on the Mitogenic Response to 8-MGuo | | | |
|---|---|---|---|---|
| | | 8$[^3H]$TdR Uptake[a] | | |
| Exp. | Anti-$Ia^k$ dilution: | CBA/CaJ ($H-2^k$) | % | Balb/c ($H-2^d$) | % |
| I | medium | 49,800 ± 810 | (100%) | 27,480 ± 800 | (100%) |

TABLE V-continued

Effect of Anti-Ia Antibodies on the Mitogenic Response to 8-MGuo

| Exp. | Anti-Ia$^k$ dilution: | CBA/CaJ (H-2$^k$) 8[$^3$H]TdR Uptake$^a$ | % | Balb/c (H-2$^d$) | % |
|---|---|---|---|---|---|
|  | 1:40 | 0 ± 2,100 | (0%) | 6,100 ± 600 | (22%) |
|  | 1:80 | 0 ± 2,300 | (0%) | 19,000 ± 580 | (69%) |
|  | 1:160 | 26,470 ± 1,740 | (53%) | 27,220 ± 660 | (99%) |
| II | medium | 31,260 ± 1,250 | (100%) | 17,700 ± 1,580 | (100%) |
|  | 1:100 | 7,650 ± 990 | (24%) | 19,950 ± 2,800 | (113%) |

$^a$ 4 × 10$^5$ CBA/CaJ or Balb/c spleen cells were cultured in 0.1 ml serum-free medium in the presence or absence of 1 mM 8-MGuo with various dilutions of anti-Ia antisera, as shown. Cultures were pulsed with 1 µCi [$^3$H]TdR for the final 24 hr of the 2 day incubation period. Results are expressed as the arithmetic mean of 5 replicate cultures ± S.E.

Figure 13:
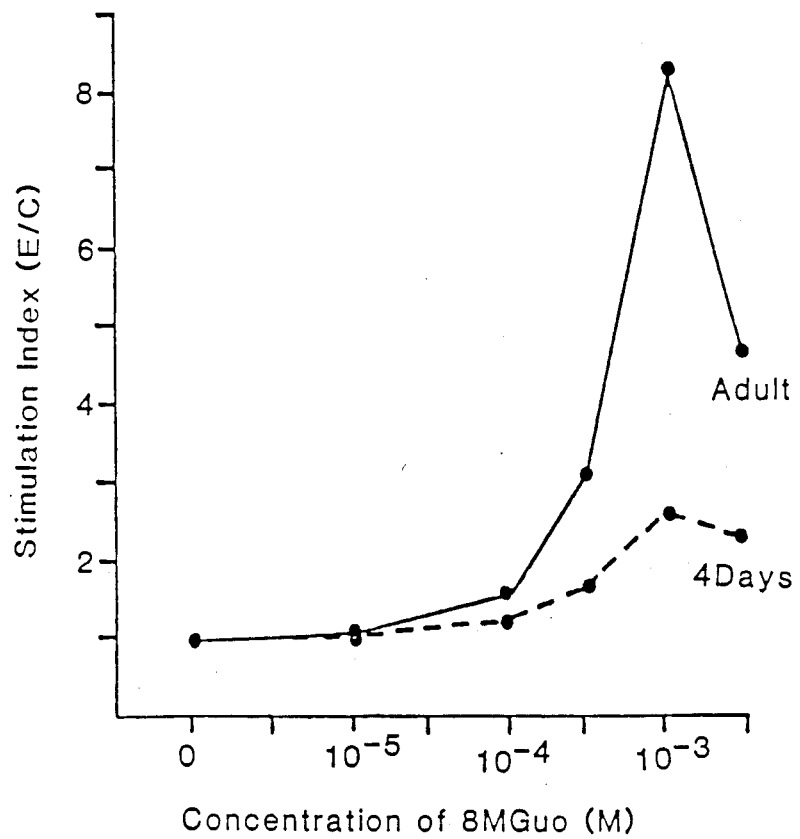
FIG. 13 illustrates the ontogeny of the mitogenic response to 8-MGuo. $4 \times 10^5$ Viable CBA/CaJ spleen cells from either 4 day old (---) or adult, 56 day old (----) mice were cultured with incremental concentrations of 8-MGuo for 2 days. Results are presented as the ratio of cpm in 8-MGuo-containing cultures to control cultures.

To corroborate that the low level responses mounted by IgD−, Ia−, CR−, or Lyb 3/5/7− cells are not attributable to a few contaminating cells positive for the above surface markers, the ontogeny of the mitogenic response was evaluated directly, using CBA/CaJ mice of various ages. The data presented in FIG. 13 show that at four days of age, prior to the expression of these markers at the cell surface, the stimulation index was approximately 20-25% of that generated in cultures of eight-week old mice.

Figure 14:
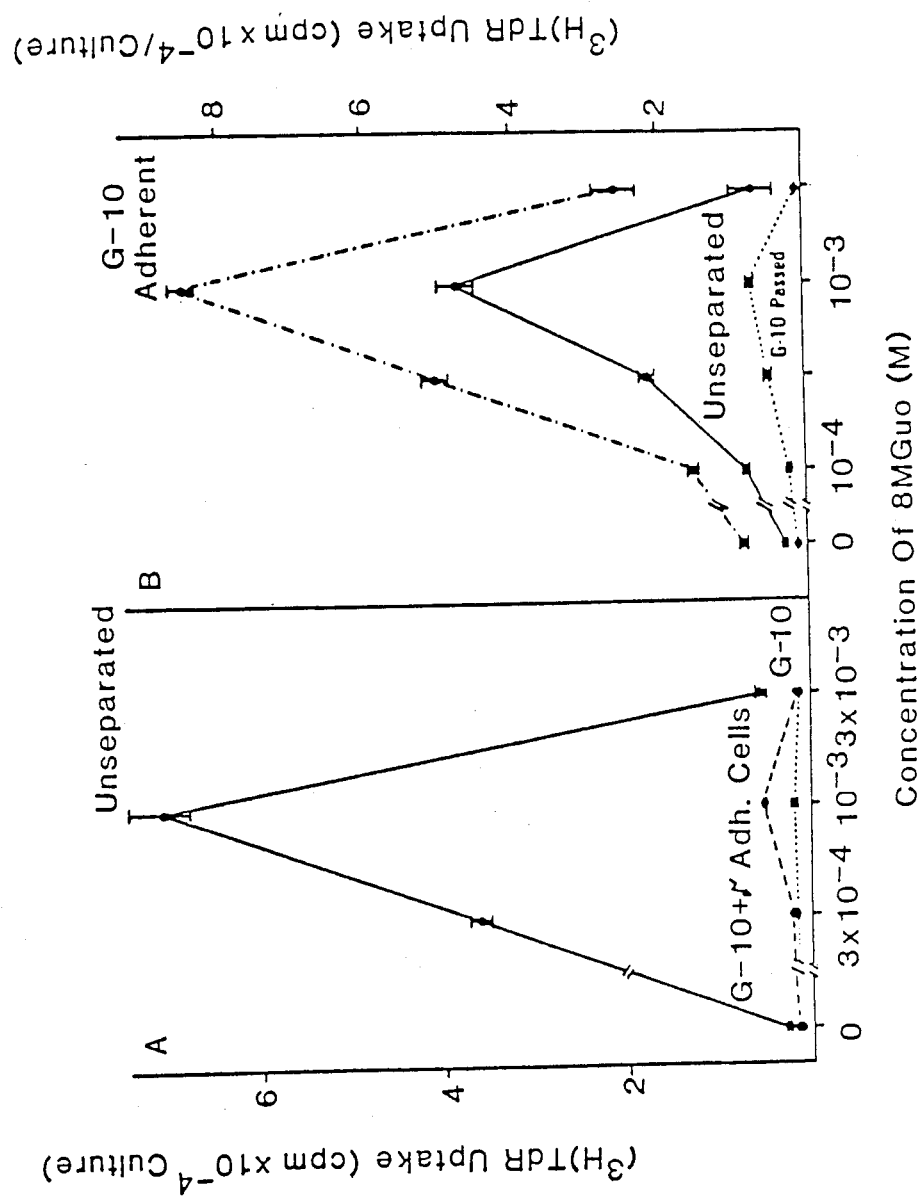
FIG. 14 illustrates the ability of 8-MGuo to activate effluent and retained cells from Sephadex G-10 columns. A. $4 \times 10^5$ Viable CBA/CaJ spleen cells were cultured either before (—) or after (...) passage over G-10 columns. A third group contained G-10 effluent cells supplemented with 5% splenic adherent cells (---). These three groups of cells were incubated with various concentrations of 8-MGuo for 2 days. Results are presented as in FIG. 11. B. $4 \times 10^5$ Viable CBA/CaJ unseparated (—), G-10 effluent (...), or G-10 adherent (-.-) cells were cultured with incremental concentrations of 8-MGuo for 2 days. Results are presented as in FIG. 11.

The response to 8-MGuo was evaluated before and after passage over Sephadex G-10 resin to illustrate the role played by adherent cells in response to compositions that include this guanine derivative as the active ingredient. Effluent cells from such columns are incapable of response to 8-MGuo, and addition of irradiated splenic adherent cells to the non-adherent cell cultures did not reconstitute their response to 8-MGuo. This is illustrated in FIG. 14A. FIG. 14B illustrates that the cell population adherent to Sephadex G-10 was enriched in cells reactive to 8-MGuo.

8-MGuo stimulates normal splenic B cells, as well as spleen cells from congenitally athymic (nu/nu) mice lacking functional T cells. The presence of T cells in B cell cultures did not enhance the mitogenic response to 8-MGuo. The action of 8-MGuo appears to be antigen nonspecific in that a large proportion of splenic B cells responded to it by blast transformation. Also, the presence of specific antigen is not required.

Lymphocytes that respond mitogenically to 8-MGuo appear to be exclusively B cells, predominantly of a mature surface phenotype. Virtually all of the responsive cells are characterized by the surface phenotype IgM+ FcR+ Thy 1.2−. Most of the cells also appear to bear the surface Ia antigen, IgD heavy chain, C3 receptors, and Lyb 3/5/7 antigens. Another group of B cells, either lacking the above markers altogether or bearing them in a very low density, may also be involved in the response.

Particulars for the results discussed above are found in Materials and Methods Section B, hereinafter. [See Goodman and Weigle, *J. Immunol.*, 130:551 (1983)].

In Vivo Modulation Of Immune Response

Figure 15:
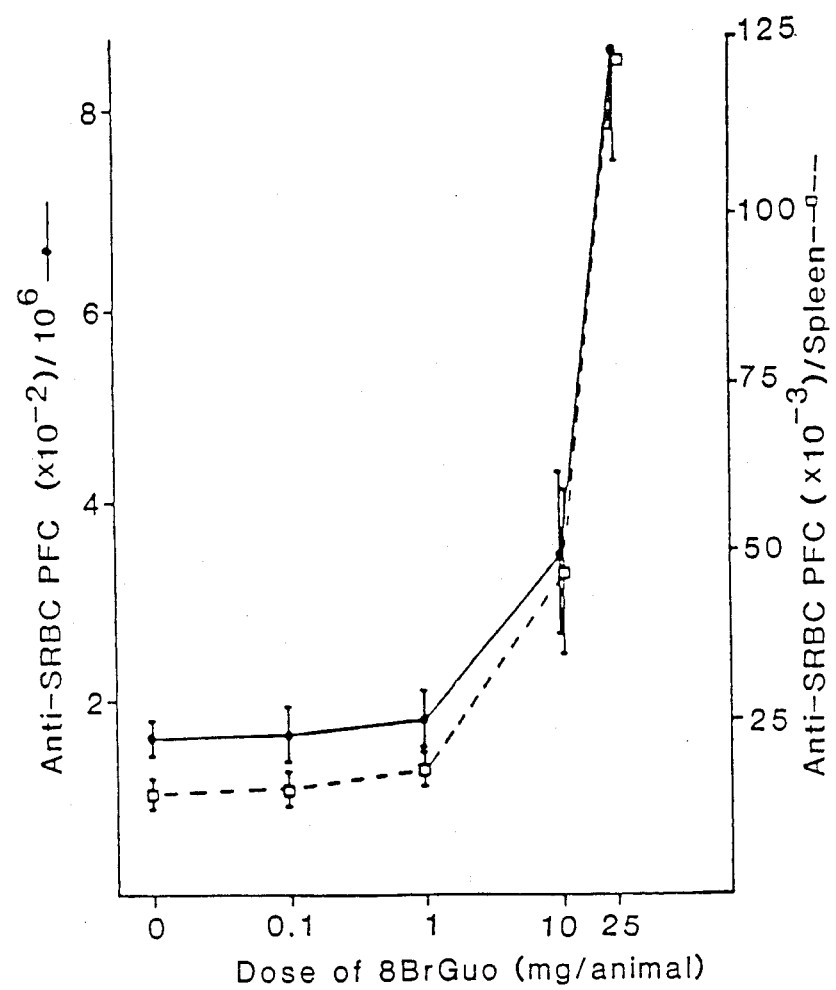
FIG. 15 illustrates results when groups of 4 CBA/CaJ mice were injected with $2 \times 10^7$ SRBC i.p. and incremental concentrations of insoluble 8-BrGuo. Direct PFC to SRBC were determined 7 days later.
Figure 16:
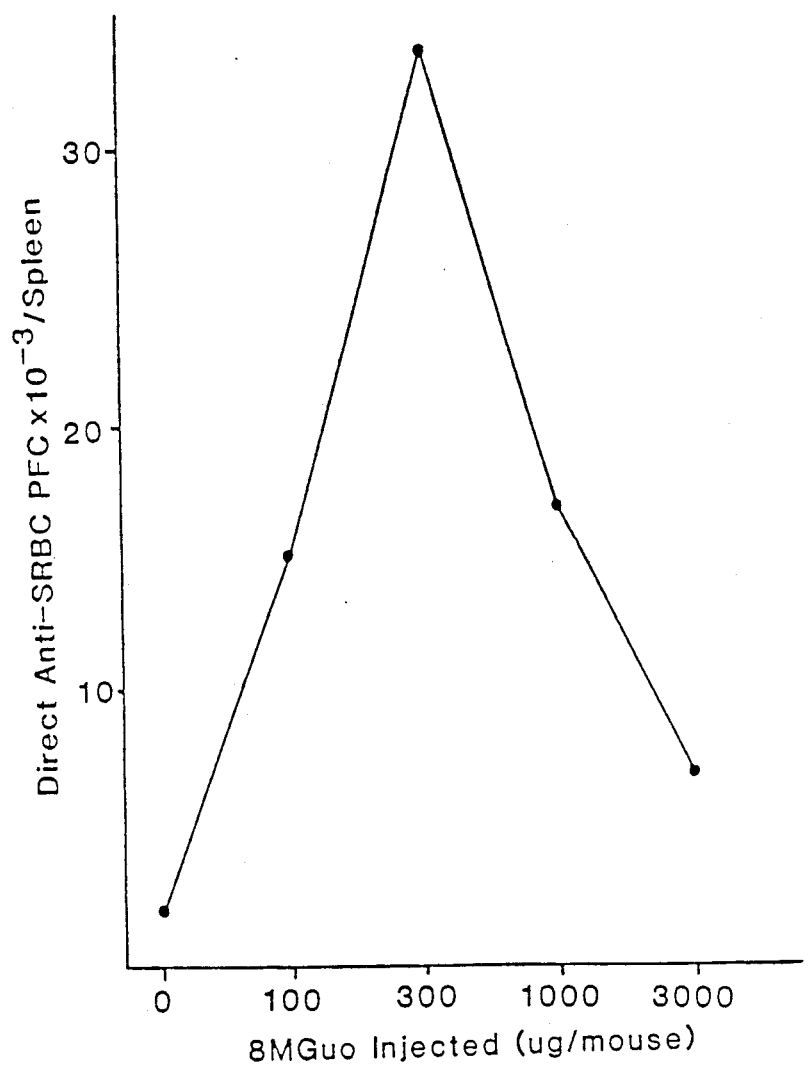
FIG. 16 illustrates results when groups of 4 CBA/CaJ mice were injected with $6 \times 10^6$ SRBC i.p. and 3 days later with incremental amounts of insoluble 8-MGuo. Direct PFC to SRBC were determined 5 days later.

FIG. 15 illustrates the striking immunopotentiating effects on the primary antibody response to SRBC in vivo observed when a composition containing a suspension of 8-MGuo was injected into CBA/CaJ mice thirty minutes after injection of the SRBC antigen. The relatively high dosages, i.e., about 25 milligrams per animal (about one gram per kilogram) were well tolerated by the animals. FIG. 16 illustrates that when administration of 8-MGuo was delayed until about 3 or 4 days after administration of the antigen, the concentration eliciting maximal adjuvanticity falls by approximately 2 orders of magnitude to a value of about 300 micrograms per mouse (about 0.01 grams per kilogram).

Figure 17:
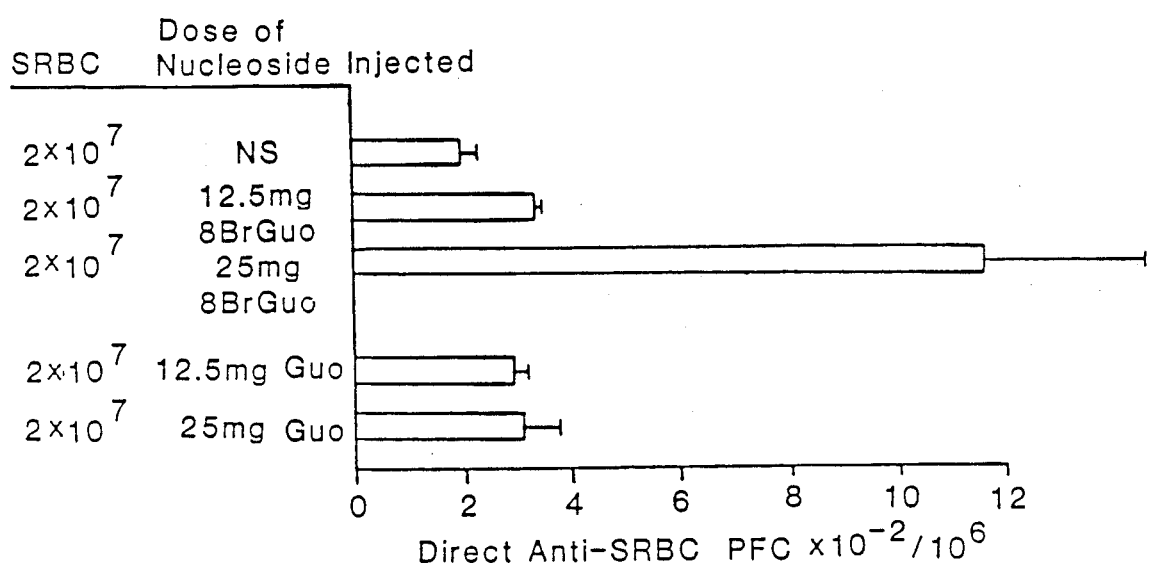
FIG. 17 illustrates results when groups of 4 CBA/CaJ mice were injected with SRBC i.p., followed by either saline (NS), 8-BrGuo, or Guo as shown. Direct PFC to SRBC were determined 7 days later.

FIG. 17 illustrates that substitution at the 8-position of the guanine derivative is critical to adjuvanticity, as it is to mitogenicity and induction of polyclonal immunoglobulin secretion as discussed hereinbefore. Thus, CBA/CaJ mice were again injected intraperitoneally (i.p.) with SRBC followed by similar injections with either normal saline (NS), 8-BrGuo or Guo. As can be seen in FIG. 17, NS and Guo produced similar, low primary antibody responses, while 8-BrGuo produced a striking antibody response.

Figure 18:
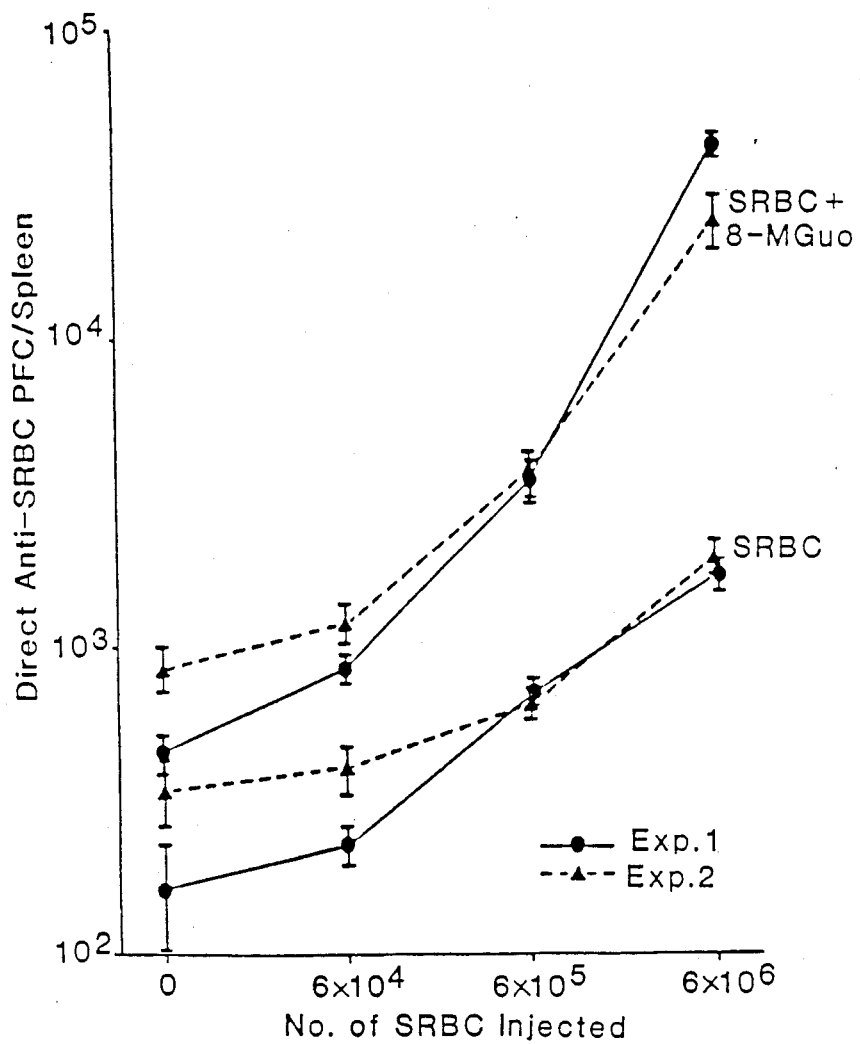
FIG. 18 illustrates results when groups of 4 CBA/CaJ mice were injected with incremental numbers of SRBC i.p. and either saline or 25 mg 8-MGuo i.p. Direct PFC to SRBC were determined 5 days later.

FIG. 18 illustrates the antigen dose dependency of the above mice to adjuvant effects of a constant level of 8-MGuo (25 milligrams per animal) injected i.p., with NS i.p. injections as a control. This figure illustrates that while there was an enhancement in the immune response at all levels of antigen injection, the enhancement became greater as the magnitude of the underlying response increased. Thus, whereas 8-MGuo magnifies the response at low dosages of antigen by about 2- to about 3-fold, at optimal antigen doses the response was amplified by approximately an order of magnitude.

Figure 19:
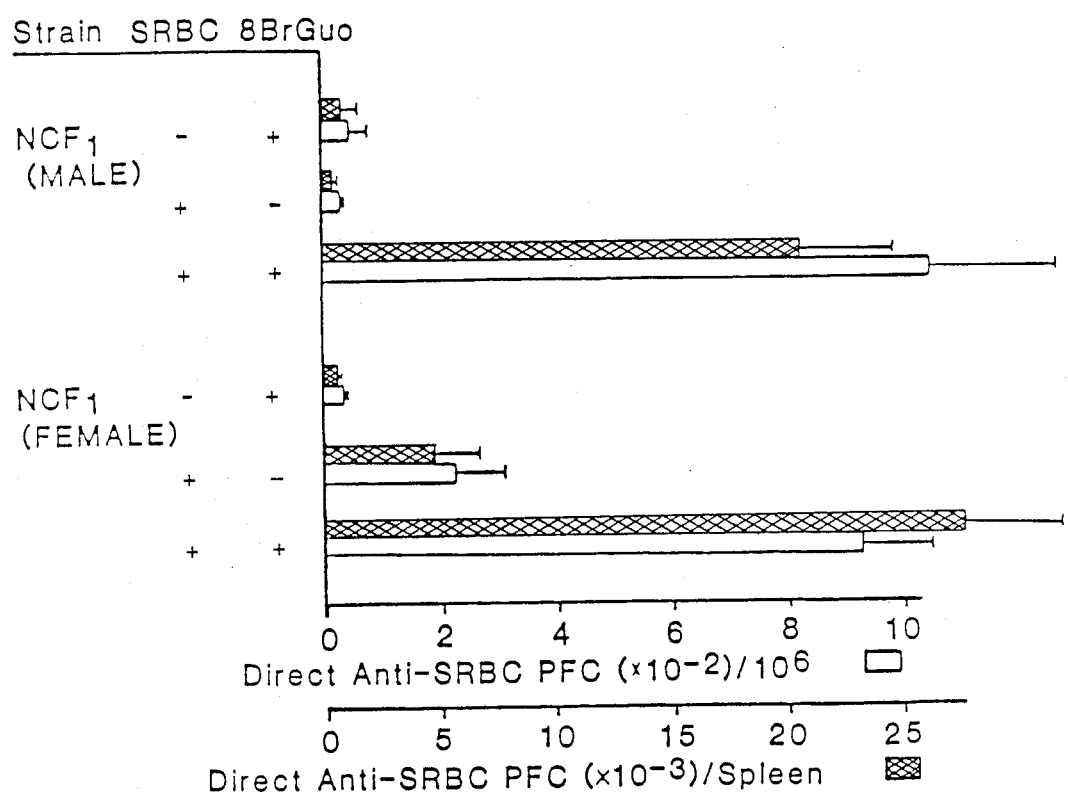
FIG. 19 illustrates results when groups of 4 NCF$_1$ male or female mice were injected with $6 \times 10^6$ SRBC i.p., followed by either saline or 25 mg of insoluble 8-BrGuo. Direct PFC to SRBC were determined 7 days later.

FIG. 19 illustrates the effectiveness of a composition of this invention containing 8-BrGuo as an adjuvant in ameliorating an immunodeficient state in vivo. This in vivo demonstration corresponds to the in vitro amelioration illustrated hereinbefore in FIG. 9.

Immunodeficient (CBA/N×CBA/CaJ) F$_1$ mice were injected i.p. with an antigenic amount of SRBC followed either by an i.p. injection of saline or of a composition containing a suspension of 25 milligrams of 8-BrGuo per animal. FIG. 19 illustrates that the underlying antibody response to a thymus-dependent antigen is virtually nil for the deficient (male) animal as compared to control (female) animals. This has been reported by Janeway and Barthold, supra, and by Scher et al., *J. Immunol.*, 123:477 (1979). This figure shows that the injection with 8-BrGuo results in a marked enhancement (more than 20-fold) of this response. This modulating enhancement raises the response levels in the deficient male mice above those achieved in normal, female mice with antigen alone, and is comparable to the enhanced response produced in normal mice by 8-BrGuo.

The above results demonstrate that optimal effects occur at a dose level for these particular animals at about 25 milligrams per animal (about one gram per kilogram) when injected shortly after antigen; i.e., within about the same 24 hour period as the antigen injection, and at about 300 micrograms per animal (0.01 grams per kilogram weight) when administration is delayed for at least about 3 to 4 days after the animal cells were subjected to the antigen in vivo.

The striking adjuvanticity of a composition of this invention occuring later in the course of the ongoing response suggests that the immunoenhancing modulatory effects are not attributable to clonal expansion of antigen-reactive cells. Rather, it is thought that the compositions of this invention provide a final triggering signal to a population of cells whose activation could not otherwise progress beyond an intermediate stage and would ultimately have been aborted.

The results further show that the compositions of this invention are more effective when cells are contacted at a time after antigen administration and are consistant with our hereinbefore discussed results of in vitro studies which demonstrated that these compositions can be used to contact cell cultures about 3 days after antigen with equal or better results than if added to the culture at the outset.

While the compositions of this invention enhance cellular responses at all doses of antigen, the degree of enhancement was usually greatest at optimal or near optimal concentrations. The adjuvanticity of the compositions of this invention has been demonstrated not to be the sum of the antigen specific and nonspecific (polyclonal) responses.

The in vivo adjuvanticity of the compositions of this invention is further illustrated by their ability to induce antibody responses in mice having a X-linked primary B cell immunodeficiency. The above results demonstrate that mice bearing this genetic defect respond normally to a T-dependent antigen when their cells are contacted by a supplemental injection of a composition of this invention.

Thus, the compositions of this invention demonstrate powerful adjuvanticity when administered in vivo. In addition, their use is beneficial in that they are nonmicrobial in nature, do not require injection of necrotizing oil emulsions, and offer a novel capability of enhancing an ongoing immune response.

The particulars of the before mentioned results are illustrated in Materials and Methods Section C. [See Goodman and Weigle, *Proc. Natl. Acad. Sci. U.S.A.*, 80:3452 (1983)].

The secondary response of mice to human gamma-globulin (HGG) as antigen in vivo has also been examined. Eleven A/J mice, five as control mice and six as treated mice, were injected intravenously in vivo with 400 micrograms of heat aggregated HGG, purified on DEAE Sephadex (Pharmacia Fine Chemicals, Piscataway, NJ) according to the procedure of Chiller and Weigle, *J. Immunol.* 110:1051 (1973), incorporated herein by reference. The control mice were then injected intraperitoneally with a solution of 10 milligrams/milliliter of carboxymethyl cellulose (CMC) in saline (0.15 molar NaCl), and the treated mice were injected intraperitoneally with 25 milligrams of an insoluble suspension of 8-BrGuo in a similar CMC solution. On day 10, the mice were administered an additional 400 micrograms of heat aggregated HGG intraperitoneally. On day 14, the mice were evaluated for specific antibody-secreting cells against HGG, according to the procedure of Chiller and Weigle, *J. Immunol.*, supra. The results obtained were 2064 PFC/spleen for the control group (HGG+CMC) and 8947 PFC/spleen for the group immunized with HGG and 8-BrGuo in CMC, both numbers representing the arithmatic means of the respective groups.

The primary response to HGG with repeated doses of nucleoside was also examined using the above techniques. 400 micrograms of heat aggregated HGG was administered intravenously in vivo on day 0 to nineteen mice. On each of days 0, 2, 4, 6 and 8, four of the mice were injected intraperitoneally with carboxymethyl cellulose solution, five with 30 microgram doses of 8-BrGuo in CMC, five with 300 microgram doses of 8-BrGuo in CMC, and five with 3000 microgram doses of 8-BrGuo in CMC. On day 10, the mice were sacrificed and the number of PFC/spleen was measured to provide data shown in Table VI, below.

TABLE VI

| | PFC/Spleen After Repeated Injections With CMC[a] or 8-BrGuo in CMC | | | |
|---|---|---|---|---|
| | | Concentration of 8-BrGuo per Repeated Injection | | |
| | CMC | 30[b] | 300[b] | 3000[b] |
| PFC/Spleen | 461 | 1046 | 1224 | 2480 |

[a]CMC = 10 milligrams per milliliter of carboxymethyl cellulose in saline (0.15 molar Nacl).
[b]Dose administered per mouse in micrograms.

As illustrated in FIG. 29, the effect of a single dose of 8-BrGuo on the primary PFC response in mice to HGG was also studied. A/J mice were injected on day 0 with 400 micrograms of heat aggregated HGG intraveneously in vivo. Three hours later either a carboxymethyl cellulose solution or 8-BrGuo suspended in CMC solution was injected. On day 6, the spleens were removed and examined for PFC against HGG. The bars on FIG. 29 are standard error bars and the data points reflect 12, 11, 12, 12, 12 and 13 test mice, respectively, from left to right. FIG. 29 illustrates that the in vivo PFC response in mice to the protein antigen human gamma-globulin increases steadily with increased dosages of 8-BrGuo.

While the above results with 8-haloguanine derivatives such as 8-BrGuo are encouraging, preliminary toxicity studies with such materials indicate that the 8-haloguanine derivatives, and particularly 8-BrGuo, may be too toxic for in vivo use at the preferred concentrations.

T Cell-Replacing Activity

Figure 20:
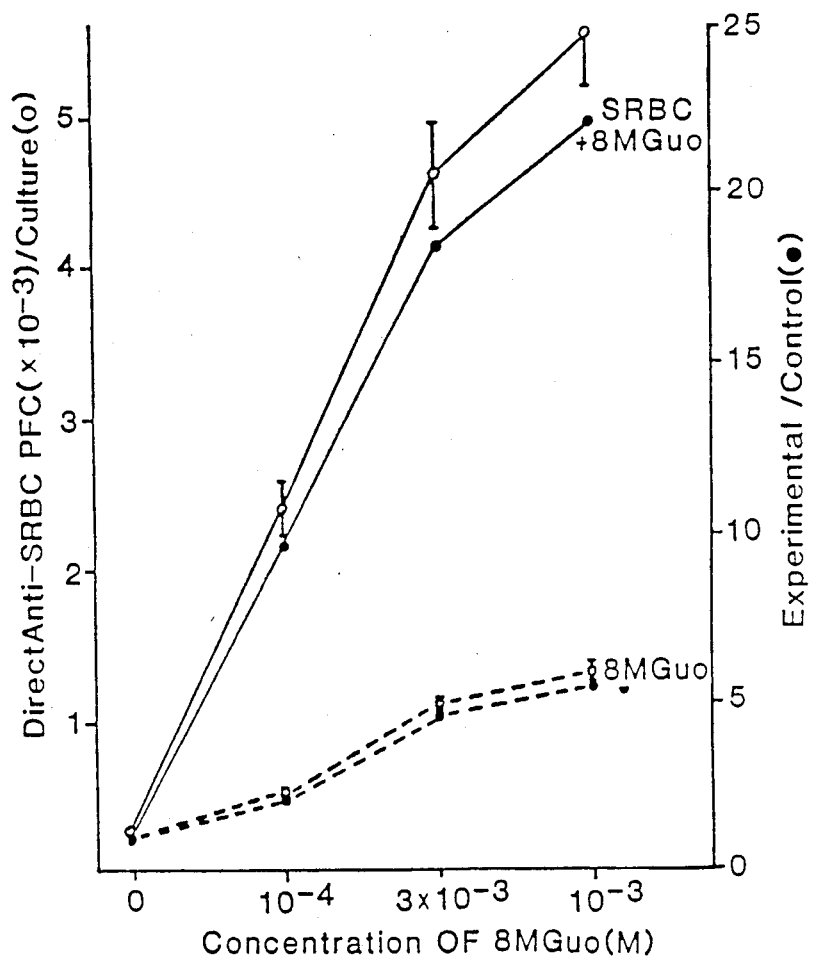
FIG. 20 illustrates the ability of 8-MGuo to replace T cells in the primary antibody response in vitro. $4 \times 10^6$ Viable CBA/CaJ splenic B cells were cultured with or without SRBC in the presence of incremented concentrations of 8-MGuo. Direct PFC to SRBC were determined 4 days later. Results are expressed as the arithmetic mean of triplicate cultures ± SE (○), or as the ratio of experimental to control (i.e., no 8-MGuo) cultures (●).

The ability of the compositions of this invention to substitute for T cells in the antibody response to a T-dependent antigen is illustrated in FIG. 20. Here, B cells generated in vitro by treatment with monoclonal anti-thy 1.2 plus complement were cultured with or without SRBC in the presence of compositions containing incremental concentrations of 8-MGuo. The data of FIG. 20 illustrate that under these conditions isolated B cell cultures are unable to respond to antigen unless supplemented with 8-MGuo. The 8-MGuo-modulated response is dose-dependent as well as antigen-dependent. In addition, this response cannot be attributed to non-specific polyclonal activation of B cells (lower curve); the response of normal spleen cells to SRBC ranges from about 600 to about 1000 PFC per culture.

Figure 21:
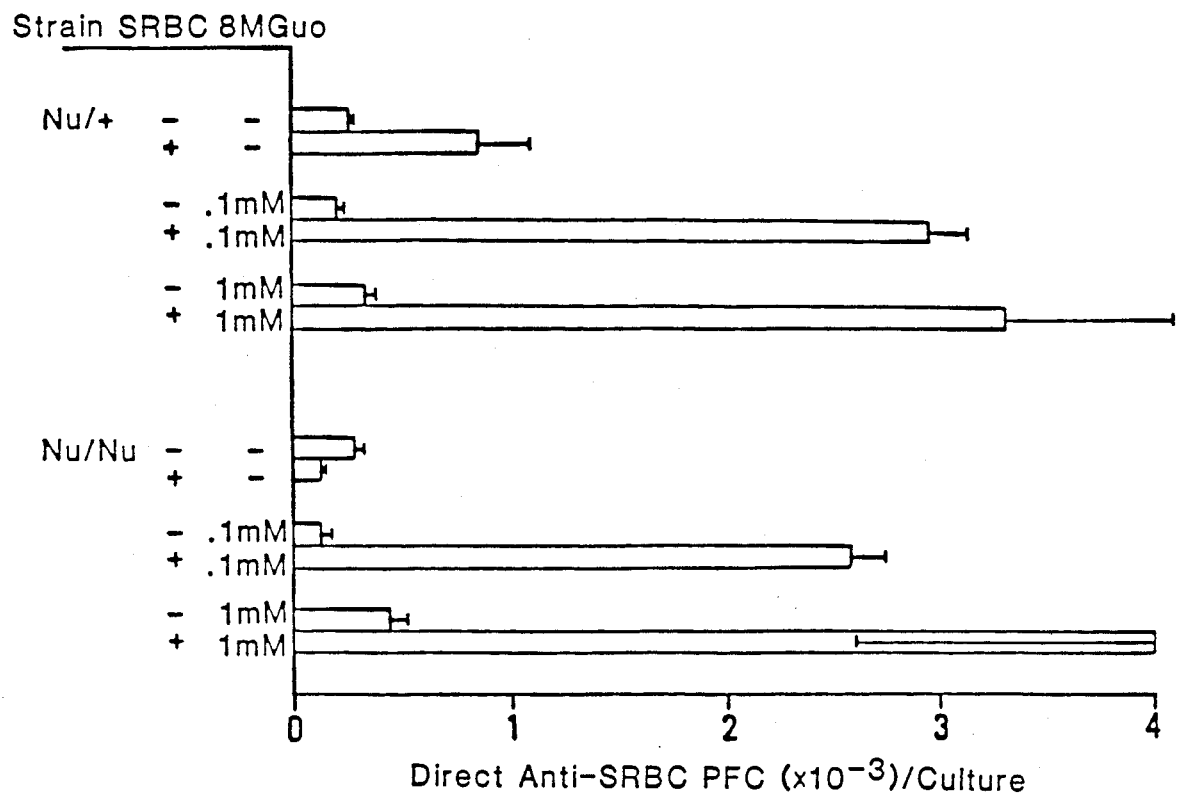
FIG. 21 illustrates the ability of 8-MGuo to replace T cells in the primary antibody responses of congenitally athymic mice. $10^7$ Viable C57BL/6J nu/nu or nu/+ spleen cells were cultured with or without SRBC in the presence or absence of 8-MGuo as shown. Direct PFC to SRBC were determined 4 days later. Results are expressed as the arithmetic mean of triplicate cultures ± S.E.

The ability of compositions of this invention to provide an alternate source of T cell-like signals is illustrated in FIG. 21 in which the capacity of the composition of this invention to reconstitute the primary antibody response of cells from congenitally athymic (nu/nu) mice is shown. Here, heterozygous (nu/+) littermates served as controls.

Supplementation of these cultures with concentrations of 8-MGuo as low as 0.1 millimolar not only reconstituted the primary antibody responses of cells from nu/nu animals, but also induced an additional adjuvant effect. The resulting ultimate responses were observed to be significantly greater than the response of nu/+ cultures to antigen alone, and were comparable in magnitude to responses generated by the nu/+ cultures supplemented with both antigen and, a composition of this invention. These results suggest that the presence of mature T cells may be unnecessary to the activity of the composition of this invention.

The above-cultured cell populations were likely to have maintained precursor T helper cells. To inhibit the IL-2 dependent proliferation of such precursor cells, as well the generation of IL-2 under circumstances of the primary immune response, whole spleen cell populations were cultured with antigen in the presence or in the absence of compositions that contain optimal concentrations of 8-MGuo. Incremental concentrations of cyclosporin A were added over the dose range shown to inhibit IL-2 production. Bunjes et al., *Eur. J. Immunol.*, 11:657 (1981).

Figure 22:
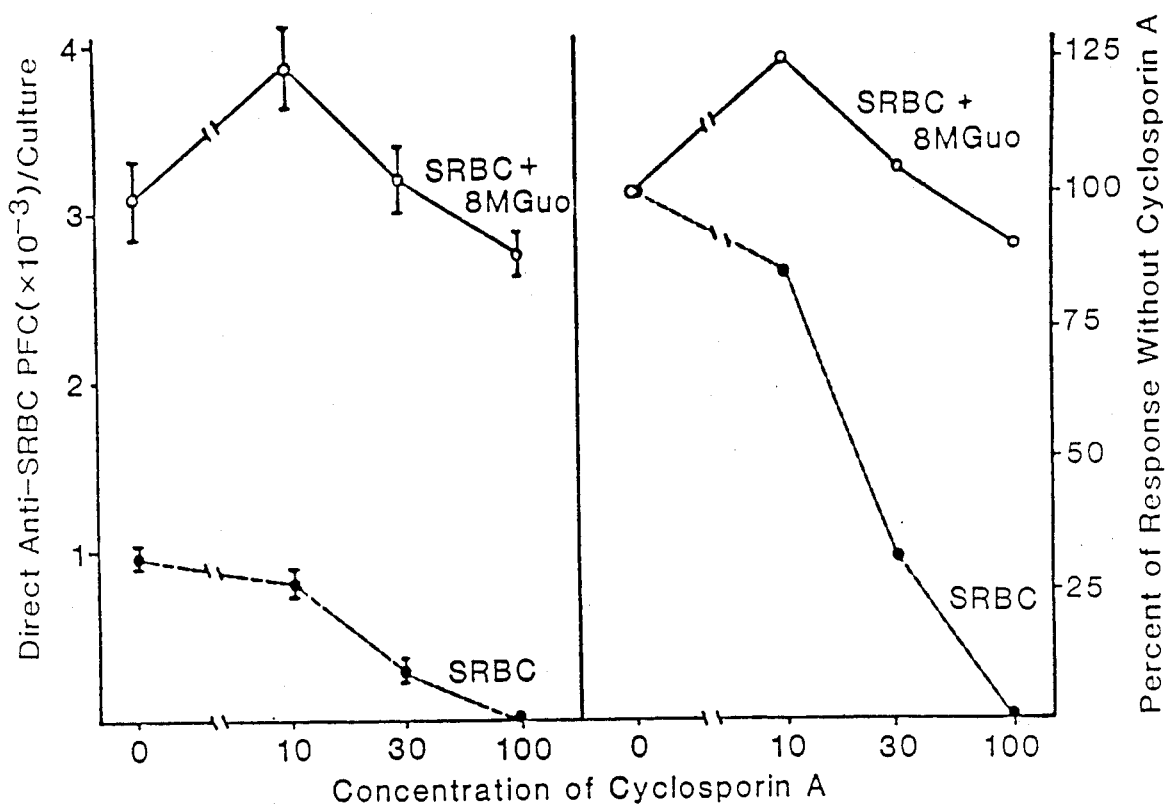
FIG. 22 illustrates the IL-2 independence of the T cell-replacing activity of 8-MGuo. $10^7$ Viable CBA/CaJ spleen cells were cultured with or without SRBC in the presence or absence of $3 \times 10^{-4}$ M 8-MGuo. Incremental concentrations of cyclosporin A were added at initiation of culture. Direct PFC to SRBC were determined 4 days later. Results are presented as the arithmetic mean of the difference of triplicate experimental and control (control=220±59 PFC) cultures ± S.E. (left panel). On the right, each response is normalized to 100% of the response to SRBC in the absence of cyclosporin A.

The data in the left panel of FIG. 22 illustrate that cyclosporin A progressively interfered with the spleen cell response to SRBC until it fell below background levels. Cultures supplemented with 8-MGuo were resistant to this inhibitory effect of cyclosporin A, thereby demonstrating the IL-2 independence of this effect.

In the right-hand panel of FIG. 22, the spleen cell response was normalized to 100% of the response to SRBC in the absence of cyclosporin A.

The responses of B cell populations containing antigen to incremental amounts of MLC supernate, which may contain IL-2 or other lymphokines, in the presence or absence of 8-MGuo, is illustrated in FIG. 23. The data of FIG. 23 illustrate that while MLC supernatants were capable of supporting a significant response to antigen in B cell cultures, the magnitude of this response was amplified several fold in the presence of 8-MGuo. Thus, administration of the composition of this invention to cells induced specific antibody formation by a mechanism distinct from that of MLC lymphokines.

The composition of this invention and T cell-derived lymphokines were added to B cell populations generated by in vivo and then in vitro treatments at either the onset of culture or 72 hours afterwards. The results of these determinations indicate that these cultures lose the ability to respond to IL-2-associated lymphokines when lymphokine addition was delayed, but responded to 8-BrGuo added at this time. These results are shown in Table VII, below. Moreover, addition of such IL-2 preparations at the onset of culture and 8-BrGuo 72 hours after culture initiation produced an additive effect, further substantiating that these two classes of adjuvant operate by distinct mechanisms.

TABLE VII

| | Kinetic Properties of 8-BrGuo and IL-2 T Cell-Replacing Effects | | |
|---|---|---|---|
| | Day of Addition[a] | | Direct PFC |
| SRBC | Day 0 | Day 3 | to SRBC/Culture[b] |
| − | −− | −− | 190 ± 21 |
| + | −− | −− | 230 ± 14 |
| + | IL-2 | −− | 1,250 ± 130 |
| + | − | IL-2 | 220 ± 8 |
| + | − | 8-BrGuo | 760 ± 4 |
| + | IL-2 | 8-BrGuo | 2,050 ± 120 |

[a] $5 \times 10^6$ Viable CBA/CaJ splenic B cells, severely depleted of T cells, were cultured for 4 days with or without $2 \times 10^6$ SRBC. On either the day of culture initiation or 3 days later, IL-2-associated lymphokines (10 units/ml) or $10^{-3}$M 8-BrGuo (final concentrations) were added to culture.
[b] Results are expressed as the arithmetic mean of quadruplicate cultures ± S.E.

The above data illustrate that the compositions of this invention provide a T cell-like signal to antigen-stimulated B cells, supplanting the need for T cells altogether under conditions of an otherwise T-dependent response. Thus, supplementation of T cell cultures, depleted of thy 1.2-bearing T cells, with a composition containing 8-MGuo entirely replaced the requirement for T helper cells in the generation of a primary antibody response to SRBC. This was true whether splenocytes were depleted of T cells by in vitro treatment with monoclonal, anti-thy 1.2 and complement, or by in vivo injection ATS followed by in vitro treatment with ATS, anti-thy 1.2, anti-Lyt 1, and anti-Lyt 2 and complement as described by Harwell et al., *J. Exp. Med.* 152:893 (1980). The TRF-like activity of 8-MGuo-containing compositions was clearly dose dependent and cannot be accounted for by nonspecific polyclonal activation in the B cells.

The possibility that the composition of this invention induced T helper precursors to mature and thereby contribute to observed responses was eliminated by the above determinations using cyclosporin A in amounts previously demonstrated to interfere with IL-2 production wnich could have contributed to the clonal expansion of such cells. (Bunjes et al., supra). While cyclosporin A could totally abrogate the response of spleen cells to SRBC in the absence of 8-MGuo, responses to subjecting those cells to the antigen in the presence of 8-MGuo were cyclosporin A resistant.

Thus, the TRF-like effect of 8-MGuo is entirely IL-2 independent. Moreover, the adjuvant increase induced by contacting cells with compositions containing 8-MGuo over cultures containing T cells and antigen but without 8-MGuo was also T cell independent and IL-2 independent. Therefore, the compositions of this invention acted as substitutes for either intact T cells or soluble T cell-derived molecules in the primary humoral response to antigen.

The above results also demonstrate that the mechanism of action of a composition of this invention was distinct from that of T cell-derived lymphokines and the T cell-replacing (or B cell stimulating) activity contained therein. This was shown by the synergistic effects of 8-MGuo and T helper factor generated in MLC supernates wherein the anti-SRBC PFC response supported by the supernates was amplified about 2- to about 3-fold by addition of compositions containing 8-MGuo.

In addition, compositions of 8-BrGuo acted with entirely different kinetic properties than those of the IL-2-associated lymphokines that co-chromatograph with IL-2 on a DEAE-Sephadex column, in that preparations containing the lymphokines were entirely ineffective when the addition to culture was delayed, while contacting cells with compositions containing 8-BrGuo 72 hours after culture initiation enabled the generation of a specific response to antigen.

Still further, when the foregoing lymphokine preparations were added initially followed by a delayed addition of 8-BrGuo, the resultant response was a summation of the individual responses supported by each agent. This observed lack of synergy with IL-2-associated lymphokines as contrasted with that observed for MLC supernates is believed attributable to effects of other lymphokines in the MLC supernates, such as interferon (See Table III, hereinbefore). Therefore, although compositions of the present invention nurture T cell independent and IL-2 independent antigen specific responses, their mechanism of action must be substantially different from that of the TRF activity of IL-2-associated lymphokines, and resemble more nearly in their temporal characterics, the properties of late-acting T cell-replacing factors, such as that described by Schimpl et al., Nature (New Biol.), 237:15 (1972).

The experimental details of the work described hereinabove are provided in Materials and Methods Section D. [See Goodman and Weigle, J. Immunol., 130:2042 (1983), incorporated herein by reference.]

Modulation of Humoral Immune Responses in Immunodeficient, Senescent Mice

Figure 24:
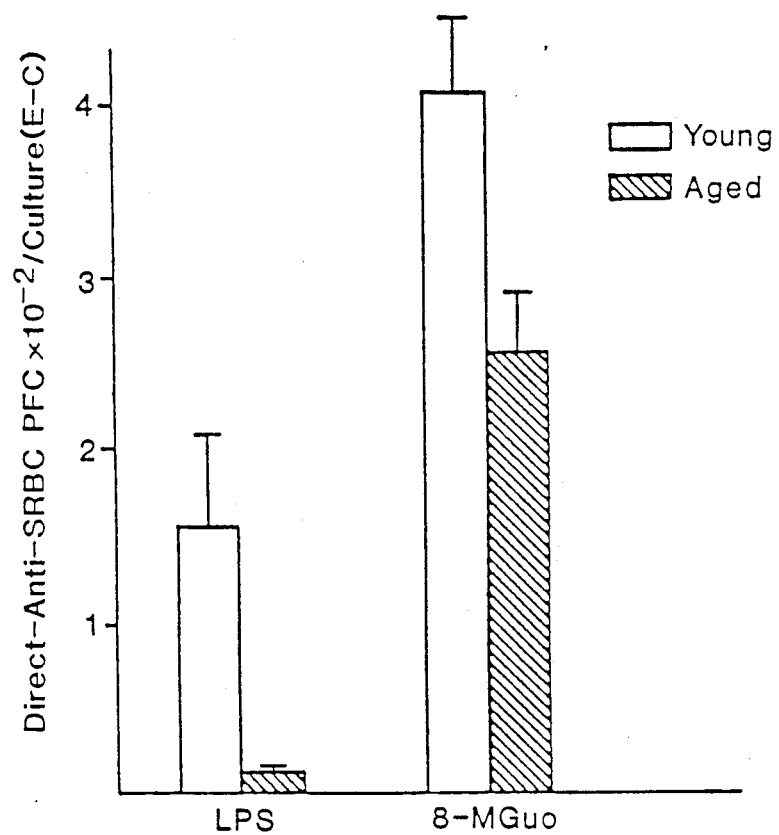
FIG. 24 illustrates induction of immunoglobulin secretion in cells from young and senescent mice. $5 \times 10^6$ Viable C57Bl/6J spleen cells were cultured for 3 days in a volume of 1 ml in the presence of medium alone, 0.1 mg/ml LPS, or $10^{-3}$ M 8-MGuo. Results are expressed as the arithmetic mean of the difference of triplicate experimental-control values (control=62 PFC/culture for young cells, 3 PFC/culture for old cells).

The relative capacities of 8-MGuo and LPS to activate murine B lymphocytes to immunoglobulin secretion was investigated in cultures of spleen cells from young and senescent C57BL/6J mice. The results of these studies shown in FIG. 24 illustrate that both 8-MGuo and LPS effectively induced polyclonal immunolglobulin secretion in spleen cell cultures taken from young adult mice (open bars). Cells from senescent mice responded vigorously when contacted with compositions containing 8-MGuo although they failed to respond to LPS (hatched bars). While the response of cells from senescent animals to 8-MGuo was less than that from cells of younger animals, the aged response to 8-MGuo was greater than the response of young cells to LPS.

LPS has been previously shown to exert potent adjuvant effects on the primary antibody response in vitro. Chiller et al. Proc. Natl. Acad. Sci. U.S.A., 70:2129 (1973); Skidmore et al. J. Immunol., 114:770 (1975). The adjuvant effect of the compositions of this invention have been illustrated hereinbefore. The relative capacities of LPS and a composition of this invention to act as adjuvants for the primary antibody response to SRBC has been evaluated in cultures of spleen cells from senescent C3H/HeN mice whose cultures are only capable of statistically insignificant responses to SRBC in the absence of adjuvant as is shown in FIG. 25.

Figure 25:
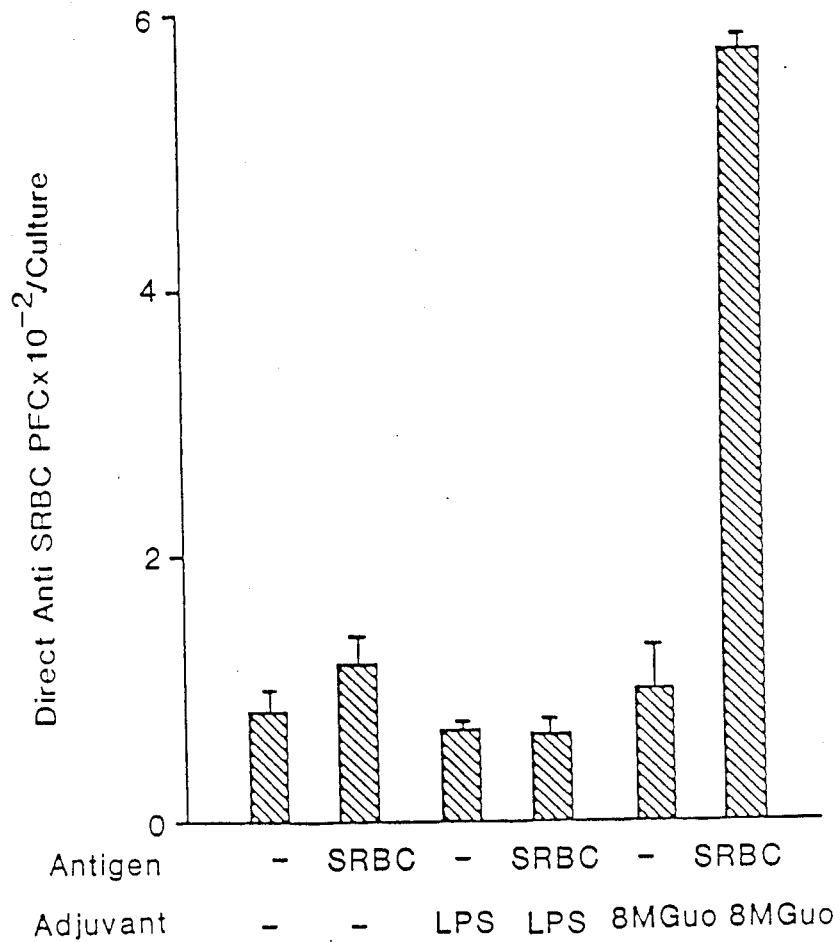
FIG. 25 illustrates adjuvanticity of 8-MGuo and LPS in senescent mice. $10^7$ Viable spleen cells from senescent C3H/HeN mice were cultured for 4 days in a volume of 1 ml in the presence or absence of $10^{-3}$ M 8-MGuo or 0.1 mg/ml LPS with or without $2 \times 10^6$ SRBC. Results are expressed as the arithmetic mean of triplicate cultures ± S.E.

As can be seen in FIG. 25, neither 8-MGuo nor LPS exert a significant polyclonal effect in this situation. It is believed that the lack of polyclonal effect for the composition containing 8-MGuo was due to the differences in dose and kinetic requirements for optimal polyclonal and antigen specific responses. However, supplementation of cultures with antigen in the presence of 8-MGuo allowed the expression of a striking response to antigen whose magnitude was comparable with the responses of cells from young adult mice to antigen in the absence, but not the presence, of 8-MGuo. The addition of LPS to cultures of antigen-stimulated cells of senescent mice consistently failed to restore their response to antigen.

TRF-like activity was demonstrated for 8-MGuo (hereinbefore) and LPS in vitro [Sjoberg et al., Eur. J. Immunol., 2:326 (1972)]whereby either normal splenic B cells or spleen cells from nu/nu mice were made capable of generating an antibody response to T-dependent antigens in the presence of either one of these activators. The relative TRF-like activities of these two agents have been evaluated in cultures of B cells from senescent C57BL/6J mice.

Figure 26:
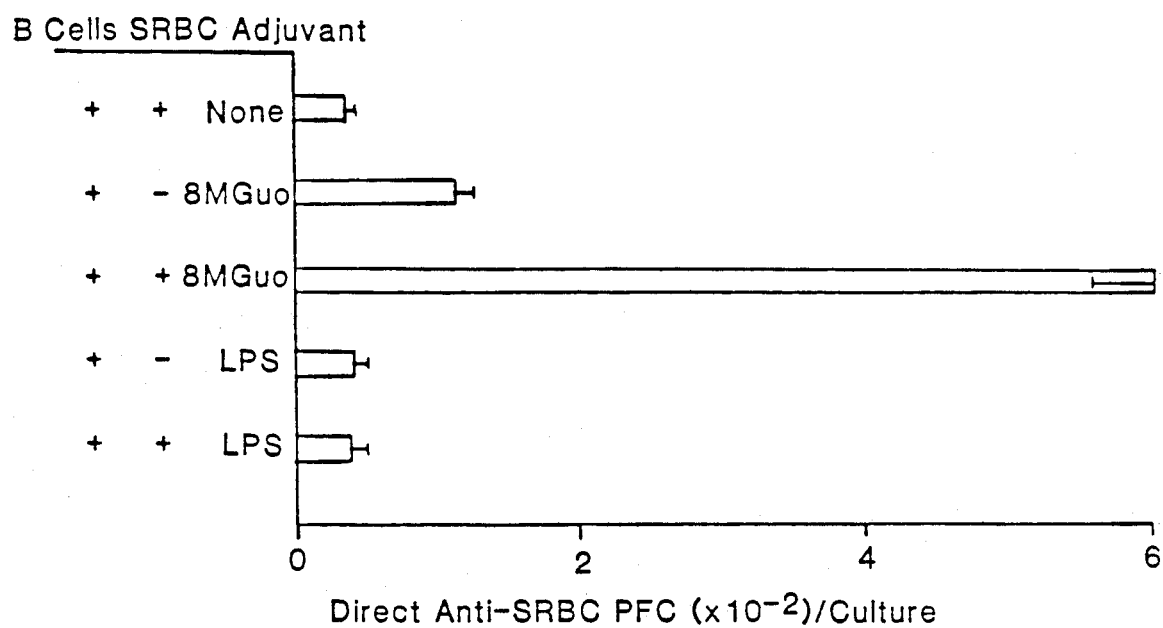
FIG. 26 illustrates relative TRF-like activities of 8-MGuo and LPS in senescent mice.

FIG. 26 illustrates that B cells alone failed to respond to either antigen or to LPS individually, and that these agents did not elicit a greater response when present in culture together. Supplementation of B cells with antigen and 8-MGuo, however, induced the expression of marked PFC response to antigen, that was comparable in magnitude to that evoked by antigen alone from cells of young adult mice. In this situation, a modest polyclonal response to the composition containing the 8-substituted guanosine derivative in the absence of antigen was discernible, and is believed to be due to the three-fold higher concentration of 8-MGuo used in these experiments. These data clearly demonstrate that circumvention of normal T cell requirements for the response to SRBC is not simply the result of an additive effect between the polyclonal response and the background.

The above data clearly demonstrate that administration of compositions of this invention to animal cells is capable of restoring antigen specific, as well as nonspecific humoral immunity in cell cultures derived from aging, senescent mice whose immune response was diminished prior to that administration. Polyclonal immunoglobulin secretion was induced very effectively by the compositions of this invention, but poorly (if at all) by LPS. This difference is believed to lie in the rapid uptake of the 8-substituted guanosine derivatives into the cell and the independence of their effects from membrane function. Transduction of the signal across the membrane thus appears to limit the responsiveness of cells from senescent mice.

This membrane defect, however, appears to discriminate between antigen specific and antigen nonspecific signals. This is illustrated by data from adjuvanticity and T cell-replacing studies. In these cases, antigen alone evoked little or no antibody response. LPS, with or without antigen, also failed to induce antibody formation as previously reported by Kishimoto et al., J. Immunol., 166:294 (1976). 8-MGuo alone provoked a low level of polyclonal response after four days of culture. However, when the 8-substituted guanosine derivative was combined with antigen, a striking response to antigen was generated.

The magnitude of the response to administration of a composition of this invention together with antigen precludes a trivial explanation such as an additive effect of background and nonspecific responses. These results indicate that antigen does transmit a signal to B cells from aging mice. This first signal, while necessary for all antigen-specific responses, is not sufficient in the case of T-dependent antigens. The above data indicate that senescent T cells provide an ineffective second signal, as does LPS. The effectiveness of a composition of this invention containing an 8-substitued guanosine derivative to transmit the second signal is thought to be attributable to its ability to bypass membranedependent events.

T cells cannot appear to play an important role in the immune-reconstituting effect of the compositions of this invention on senescent mice. Populations of B cells and macrophages responded to antigen in the absence of functional T cells so long as the composition of this invention provided a T cell-like second signal, with the magnitude of response in the presence or absence of T cells being generally comparable. Previous reports that T cells from aging mice function poorly in humoral responses [Morgan et al., *Cel. Immunol.*, 63:16 (1981); Krogsrud et al., *J. Immunol.*, 118:1607 (1977)] and produce little IL-2 [Miller et al., *Eur. J. Immunol.*, 11:751 (1981)] provide a rational basis for understanding these observations.

Appreciation of the potential survival value to the host of modulating inadequate immune responses has led to intensive investigation of methods for augmenting systemic immunity. Nowhere is the importance of this approach more apparent than for the immunodeficiency which frequently accompanies the aging process. Elderly individuals are subject to a wide variety of immune-related disorders. The above results in senescent mice substantiate the ability of the compositions of this invention to short circuit one link (i.e., cell membrane function) in the chain of events that culminates in induction of B lymphocyte function, a link known to be defective in aged animals.

The experimental conditions utilized in obtaining the above-mentioned results may be found in Materials and Methods Section E, hereinafter.

Adjuvanticity By Oral Administration

Adjuvanticity of the compositions of this invention administered by in vivo i.p. injection was discussed hereinbefore. The present results relate to adjuvanticity of the compositions of this invention which were administered orally through a tube extending into the stomachs of the animals. These results were obtained using the conditions discussed in Materials and Methods Section C.

SRBC were injected i.p. and PFC determinations were made seven days after the initial i.p. injection of the SRBC. The compositions of this invention containing 8-MGuo were administered perorally within either the same 24-hour period as the antigenic dose of SRBC or 72 hours thereafter. The data from these determinations are shown hereinbelow in Table VIII.

TABLE VIII

Adjuvanticity of Orally Administered 8-MGuo[a]

| Antigen | Dose of 8-MGuo[b] | Day of 8-MGuo Administration | |
|---|---|---|---|
| | | Day 0 | Day 3 |
| | | PFC Against SRBC/Spleen[c] | |
| SRBC | None | 5,415 | 5,415 |
| SRBC | 0.3 mg | 16,391 | 29,950 |
| SRBC | 3.0 mg | 21,803 | —[d] |
| SRBC | 30.0 mg | 18,653 | —[d] |

[a]CBA/CaJ mice were injected with 0.3 ml of a 0.1% suspension of SRBC i.p. on Day 0.
[b]Dosage rates are per animal.
[c]PFC determination was carried out as per FIG. 15.
[d]Not measured.

As can be seen from the above data, administration of a composition of this invention provided an enhanced primary response to the antigen whether contacted with the cells within the same 24-hour period that those cells were subjected to the antigen, or 72 hours thereafter. As has been shown hereinabove, adjuvanticity is improved when there is a delay of at least about 3 days between subjecting the cells to the antigen and contacting them with a composition of this invention.

Cell Activation and Differentiation By 8-Bromoguanosine Derivatives

Cell activation and differentiation studies (mitogenesis) were conducted using 8-bromo-2'-methyl guanosine, 8-bromo-2', 3', 5'-tri-O-acetyl guanosine and 8-bromo-2'-deoxy-guanosine following procedures substantially similar to those illustrated in Goodman and Weigle, *Proc. Natl. Acad. Sci. U.S.A.*, supra. The unbrominated guanosine derivatives were obtained from Sigma Chemical Company, St. Louis, Mo. Bromination was conducted as described in the referenced papers to provide a single spot on polyethyleneimine cellulose plates as described in the referenced papers. Cell cultures were initiated in the presence of the 8-substituted guanine derivative for a period of 24 hours followed by administration of [$^3$H]TdR, followed by a further 24-hour period of incubation and then harvesting. Determination of [$^3$H]TdR was carried out as discussed in the above cited references. Data for the above-mentioned 8-BrGuo derivatives are shown in Table IX below.

TABLE IX

Mitogenesis by 8-BrGuo Derivatives[a]

| Concentration of 8-BrGuo Derivative[c] | [$^3$H]TdR Uptake Per Culture (cpm)[b] | | |
|---|---|---|---|
| | 8-BrGuo-1[d] | 8-BrGuo-2[e] | 8-BrGuo-3[f] |
| 0 | 5,670 ± 230 | 7,350 ± 520 | 4,906 ± 1,417 |
| 1 × 10$^{-4}$ | 7,890 ± 420 | 19,870 ± 370 | 5,616 ± 339 |
| 3 × 10$^{-4}$ | 16,670 ± 140 | 38,280 ± 1,260 | 4,866 ± 325 |
| 1 × 10$^{-3}$ | 56,170 ± 2,720 | 83,100 ± 2,110 | 10,682 ± 761 |
| 3 × 10$^{-3}$ | 86,890 ± 1,480 | 1,950 ± 230 | 46,231 ± 1,080 |
| 1 × 10$^{-2}$ | 1,890 ± 360 | —[g] | 1,249 ± 321 |

Figure 11:
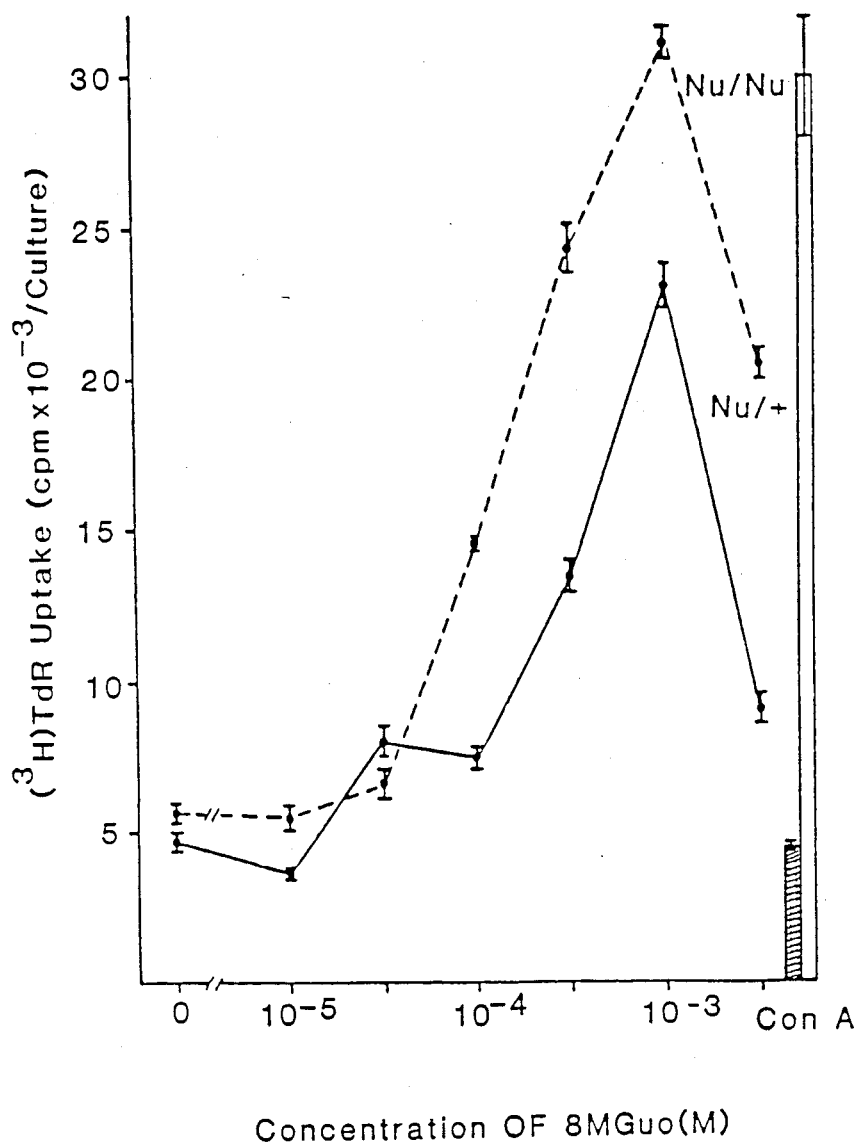
FIG. 11 illustrates the ability of 8-MGuo to promote DNA synthesis in cultures from congenitally athymic mice. $4 \times 10^5$ Viable C57BL/6J nu/nu (----) or nu/+(----) spleen cells were cultured with incremental concentrations of 8-MGuo or 1 micro g/ml Con A for 2 days. Results are presented as in FIG. 10A.

[a]4 × 10$^5$ Viable CBA/CaJ spleen cells were cultured in 0.1 ml of serum-free medium with compositions containing incremental concentrations of the 8-BrGuo derivatives.
[b][$^3$H]TdR uptake was measured as per FIG. 11.
[c]Molar concentration of mitogen per culture.
[d]8-Bromo-2',3',5'-triO—acetyl guanosine.
[e]8-Bromo-2'-O—methyl guanosine.
[f]8-Bromo-2'-deoxy-guanosine.
[g]Data not taken.

The above data amply illustrate that derivatives on the aldose portion of 8-substituted guanine derivatives provide cell activation differentiation effects similar to that of 8-BrGuo.

Using the techniques discussed hereinbefore regarding mitogenesis, further comparisons were made as reflected in Table X and FIG. 30. In order to obtain the data therein, the assay procedure of Goodman and Weigle, *J. Immunol.*, 130:551 (1983) was utilized and is incorporated by reference. Table X illustrates that various oxo and mercapto guanine derivatives promote mitogenesis. FIG. 30 further illustrates the ability of 8-MGuo and 8-thio-(beta-hydroxyethyl)Guo to promote mitogenesis.

While it has been noted that mitogenesis and polyclonal activation to immunoglobulin secretion as compared to adjuvanticity and TRF-like activity for antigen-specific responses need not be coincident, it is believed that the 8-substituted guanine derivatives described as useful herein that are mitogenic, as exemplified in Table X, and provide polyclonal activation, as exemplified in Table II, also provide adjuvanticity and TRF-like activity for antigen-specific responses as do 8-MGuo and 8-BrGuo.

TABLE X

| Cell Type | Guanine Derivative | [3H]TdR Uptake (cpm/culture)[a] | | | |
|---|---|---|---|---|---|
| | | Control | .3 mM[b] | 1 mM[b] | 3 mM[b] |
| Spleen | 8-oxoGuo[c] | 4,000 | 7,000 | 41,000 | 31,000 |
| | 8-methoxyGuo[d] | 3,700 | 5,800 | 25,300 | 54,700 |
| | 7-met-8-oxoGuo[e] | 3,800 | 111,000 | 141,000 | 43,000 |
| | 8-MGuo[f] | 3,400 | —[h] | 76,600 | —[h] |
| | 8-methylMGuo[g] | 3,400 | 13,500 | 68,600 | 72,900 |
| Spleen | 8-oxoGuo[c] | 6,000 | 12,000 | 51,000 | 91,000 |
| | 8-methoxyGuo[d] | 6,000 | 8,300 | 22,000 | 65,000 |
| | 7-met-8-oxoGuo[e] | 6,000 | 149,000 | 170,000 | 85,000 |
| | 8-MGuo[f] | 6,000 | —[h] | 100,000 | —[h] |
| | 8-methylMGuo[g] | 5,000 | 35,000 | 97,000 | 88,000 |
| B cells | 8-methoxyGuo[d] | 7,000 | 13,000 | 40,000 | 71,000 |
| | 8-methoxyGuo[d] | 7,000 | 9,000 | 21,000 | 51,000 |
| | 7-met-8-oxoGuo[e] | 7,000 | 132,000 | 168,000 | 81,000 |
| | 8-MGuo[f] | 7,000 | —[h] | 88,000 | —[h] |
| | 8-methylMGuo[g] | 5,000 | 25,000 | 45,000 | 63,000 |

[a] [3H]TdR uptake was measured as described in relation to FIG. 11.
[b] Millimolar concentration of mitogen per culture.
[c] 8-oxoguanosine
[d] 8-methoxyguanosine
[e] 7-methyl-8-oxoguanosine
[f] 8-mercaptoguanosine
[g] 8-methylthioguanosine
[h] Data not taken.

Inhibition Of The Growth Of Neoplastic Cells

While the previous discussion has centered primarily around the cell growth-stimulating and adjuvant effects provided by administering compositions of this invention to various cells, and particularly to leukocytes, the present results relate to the inhibition of proliferation of neoplastic cells that is afforded by contacting those neoplastic cells with a composition of this invention. More specifically, cultured lymphoma B cells, neoplastic macrophage and hybridoma cell cultures were incubated in the presence of incremental amounts of 8-MGuo using similar cell cultures containing no 8-MGuo as controls. Non-neoplastic splenic cells were also cultured in the presence and absence of 8-MGuo to be used as a comparison to the cultures of neoplastic cells.

The results of these culture studies are illustrated in FIG. 27 wherein the uptake of [3H]TdR in the presence of 8-MGuo divided by the similar uptake and control cultures is plotted against the concentration of 8-MGuo for each of the four cultured cell types. Examination of FIG. 27 shows that while splenic cells are stimulated to proliferate in the presence of 8-MGuo, the growth of each of the three neoplastic cells types is greatly inhibited by concentrations of 8-MGuo in excess of about 0.1 millimolar. Examination of the kinetics of uptake indicate that administration of a composition of this invention to the neoplastic cells causes cytotoxicity at a stage during metabolism of the cells, rather than lysis.

The mechanism by which growth of neoplastic cells is inhibited by contacting those cells with the composition of this invention is unknown. However, as neoplasticity can be explained as a manifestation of a cellular message that causes the cells to replicate at a much higher rate than is normal, it may be that the compositions of this invention spur those rapidly replicating cells still further to a point at which the cells are replicating so rapidly that they die.

Induction Of Interleukin-1-Like Activity

IL-1, produced by macrophages, assists in the production of IL-2 in T cells. IL-2 is a growth factor for T cells and assists in the transformation of T helper cells. Using supernates from irradiated spleen cell cultures in which only the macrophages survived irradiation [Gorczynski, J. Exp. Med., 134:1201 (1971)] and which were supplemented with compositions of this invention that contained incremental concentrations of 8-MGuo, it was found that thymocytes could be made to proliferate in a manner similar to that by which thymocytes proliferate in the presence of IL-1. Consequently, it is believed that the compositions of this invention stimulate what may be termed IL-1 like activity in that such macrophage supernatants induce thymocytic responses similar to those that are exhibited by thymocytes in the presence of IL-1. The data in Table XI, below, illustrate the effects provided by contacting thymocytes with supernates that contain no IL-1, or have IL-1-like activity present.

TABLE XI

Induction of IL-1-Like Activity by 8-MGuo[a]

| Supernate Make-up | | [3H]TdR Uptake Per Culture (cpm)[d] |
|---|---|---|
| Spleen Cells[b] | Concentration of 8-MGuo[c] | |
| + | None | 235 ± 80 |
| + | $1 \times 10^{-4}$ | 710 ± 70 |
| + | $3 \times 10^{-4}$ | 860 ± 40 |
| + | $1 \times 10^{-3}$ | 3,440 ± 170 |
| + | $3 \times 10^{-3}$ | 3,260 ± 120 |
| − | $1 \times 10^{-4}$ | 380 ± 60 |
| − | $3 \times 10^{-4}$ | 540 ± 50 |
| − | $1 \times 10^{-3}$ | 640 ± 110 |
| − | $3 \times 10^{-3}$ | 1,480 ± 180 |

[a] $5 \times 10^4$ Viable CBA/CaJ thymocytes were cultured with or without supernatants from irradiated spleen cell cultures generated in the presence of compositions containing incremental concentrations of 8-MGuo.
[b] The presence of spleen cells in the supernate is indicated by a "+" sign, while the absence of spleen cells is indicated by a "−" sign.
[c] Molar concentration of 8-MGuo in the cultures.
[d] [3H]TdR uptake was determined as per FIG. 11.

The above data illustrate that radioactive thymidine is incorporated into thymic cells in the presence of splenic cell supernates which contained compositions of this invention.

Inducement Of Endogenous Interferon Production

Splenic cells were cultured as described in the previously referenced paper by Goodman and Weigle J. Immunol, supra for periods of 24 and 48 hours, after which time the cells were harvested, and the supernatant from the harvested cell cultures was examined for production of interferon. This examination revealed that relatively high levels of interferon were produced as assayed by inhibition of viral plaque formation [Armstrong, Appl. Microbio., 21:723 (1971)].

Mitogenic agents are known to stimulate interferon production in the absence of viral interferon-inducing agents. However, most of such mitogenic, interferon-inducing agents are not tolerated by animals, and therefore cannot be used. On the other hand, the compositions of the present invention are well tolerated and are therefore efficacious in inducing endogenous interferon production in the absence of naturally occurring microbiological interferon production-inducing agents and in providing adjuvanticity for interferon production in the presence of interferon production-inducing agents. In addition, on the basis of the ability of the compositions of this invention to enhance cellular responses to an eliciting agent (adjuvanticity), it is believed that such compositions likewise increase the production of interferon in the presence or absence of interferon-inducing agents.

Enhanced 5'-Nucleotidase Activity in Immunodeficient States

As noted previously, an important use of an adjuvant is in the amelioration of immunodeficient states. X-linked hypogammaglobulinemias represent one such immunodeficient state in which males exhibit reduced lymphocyte cell surface ecto-5'-nucleotidase (5'NT) activity.

The data in FIG. 28 shows the enhancement in percent basal 5'NT activity when lymphocytes of CBA/-CaJ mice were contacted with a composition of this invention containing 8-MGuo. Similar results were obtained using human lymphocytes provided by one of the instant inventors. These data further illustrate the immune-reconstituting capacity of the compositions of this invention when used to contact immunodeficient cells.

Enhancement Of Neutrophil Enzyme Secretion

One of the most active agents for inducing the release of lysosomal enzymes from neutrophils is the complement component C5a. We observe that human neutrophils first sedimented with dextran and spun through a ficoll gradient according to the method of Chenoweth and Hugli, *Pro Natl. Acad. Sci. U.S.A.*, 75:3943(1978), then resuspended in Hank's balanced salt solution at $4 \times 10^6$ cells per milliliter and thereafter contacted with a composition of this invention containing 8-MGuo release enhanced amounts of lysosomal enzyme.

The observed enhancement of lysosomal enzyme secretion was approximately equal to that achieved by use of an optimal concentration of complement component C5a when the concentration of 8-MGuo utilized in the composition of this invention was about 1 to about 10 millimolar. Enzyme secretion was assayed in accordance with the method of Chenoweth and Hugli, supra.

The active ingredients of the present invention are administered to animals perorally or parenterally in customary dosage unit compositions, that is, as compositions in unit dosage form comprising a physiologically tolerable carrier and an effective dosage unit of the active ingredient.

The term "unit dosage form" as used herein refers to physically discrete units suitable as unitary dosages for human patients and other warm blooded animals, each unit containing a predetermined quantity of the active ingredient calculated to produce the desired therapeutic effect in association with the required physiologically tolerable carrier, e.g. a diluent or a vehicle. The specifications for the novel unit dosage forms of this invention are dictated by and are directly dependent on (a) the unique characteristics of the active ingredient and the particular therapeutic effect to be achieved, and (b) the limitations inherent in the art of compounding such an active ingredient for therapeutic use in humans and animals. Examples of suitable unit dosage forms in accord with this invention are tablets, capsules, pills, powder packets, granules, wafers, and the like, segregated multiples of any of the foregoing, as well as solutions and suspensions.

The amount of active ingredient that is to be administered depends on the age and weight of the patient, the particular condition to be treated, the frequency of administration, and the route of administration. The dose range can be about 1 to about 1000 milligrams per kilogram of body weight, more preferably about 5 to about 250 milligrams per kilogram of body weight and most preferably about 10 to about 100 milligrams per kilogram of body weight. The human adult dose is in the range of about 50 to about 50,000 milligrams daily, given as a single dose or in 3 or 4 divided doses. Veterinary dosages will correspond to human dosages with the amounts administered being in proportion to the weight of the animal as compared to adult humans.

EXAMPLE 1

Tablets

Tablets are compounded from the following ingredients:

|  | Parts by Weight |
| --- | --- |
| 8-BrGuo | 5.0 |
| Lactose, powdered | 35.4 |
| Corn starch, dry | 33.0 |
| Finely divided $SiO_2$ | 5.6 |
| Polyvinylpyrrolidone | 0.6 |
| Magnesium sterate | 0.4 |
|  | 80.0 |

8-BrGuo is thoroughly admixed with the lactose, 25.0 parts by weight of the corn starch, and 4.0 parts by weight of the $SiO_2$. The resulting admixture is then uniformly moistened with a 5% ethanolic solution of polyvinylpyrrolidone. The moist mass is then passed through a one-millimeter mesh screen to produce a granulate. The produced granulate is dried for about 24 hours at 60° C. in a drying chamber. The dried granulate is again passed through a one-millimeter mesh screen. 70.0 Parts of the obtained granulate are admixed in a suitable mixer with a mixture consisting of the remainder of the $SiO_2$, the remainder of the corn starch and all of the magnesium stearate which mixture previously had been passed through a one-millimeter mesh screen. The thus-obtained admixture is then pressed into tablets weighing 800 milligrams each and containing 50 milligrams of 8-BrGuo.

EXAMPLE 2

Starch Capsules

Capsule contents are compounded from the following ingredients:

|  | Parts by Weight |
| --- | --- |
| 8-MGuo | 50.0 |
| Lactose | 450.0 |
| Corn Starch | 500.0 |
|  | 1000.0 |

8-MGuo is gradually admixed with the lactose. When all of the lactose has been admixed, the obtained admixture is blended with the corn starch. The resulting blend is then filled into capsules holding 1.0 gram of the blend. Each capsule contains 50 milligrams of 8-MGuo.

EXAMPLE 3

Tablets

A lot of 10,000 tablets, each containing 50 milligrams of 8-BrGuo, is prepared from the following types and amounts of ingredients:

| 8-BrGuo | 500 grams |
| --- | --- |
| Dicalcium Phosphate | 1000 grams |

| | |
|---|---|
| Methylcellulose, U.S.P. (15 cps) | 60 grams |
| Talc | 150 grams |
| Corn Starch | 200 grams |
| Magnesium stearate | 10 grams |

8-BrGuo and dicalcium phosphate are mixed well, granulated with 7.5 percent solution of methyl cellulose in water, passed through a No. 8 screen (U.S. Std. Sieve Series) and dried carefully. The dried granules are passed through a No. 12 screen (U.S. Std. Sieve Series), mixed thoroughly with the talc, starch and magnesium stearate, and compressed into tablets.

These tablets are useful for enhancing antibody production when administered perorally at a dose of one to three tablets every eight hours.

EXAMPLE 4

Injectable Preparation

A sterile preparation suitable for intracavitary injection and containing 75 milligrams of 8-MGuo in each milliliter is prepared from the following types and amounts of ingredients:

| | |
|---|---|
| 8-MGuo | 7 grams |
| Benzyl benzoate | 200 milliliters |
| Methylparaben | 1.5 grams |
| Propylparaben | 0.5 grams |
| Cottonseed oil q.s. to | 1000 milliliters |

One to three milliliters of this sterile preparation are injected intraperitoneally once a day to enhance humoral immunity.

EXAMPLE 5

Aqueous Preparation for Oral Use

An aqueous preparation for oral use containing in each 5 milliliters (1 teaspoon) 50 milligrams of 8-BrGuo is prepared from the following ingredients:

| | |
|---|---|
| 8-BrGuo | 55 grams |
| Methylparaben, U.S.P. | 0.75 grams |
| Propylparaben, U.S.P. | 0.25 grams |
| Saccharin sodium | 1.25 grams |
| Cyclamate sodium | 0.25 grams |
| Glycerin | 300 milliliters |
| Tragacanth powder | 1.0 grams |
| Orange oil flavor | 1.0 grams |
| F.D. and C. orange dye | 0.75 grams |
| Deionized water, q.s. to | 1000 milliliters |

A dose of one teaspoon two to four times per day is useful for enhancing humoral immunity.

MATERIALS AND METHODS

Section A

Mice.

CBA/CaJ male mice, 8–16 weeks of age, were purchased from the Jackson Laboratory, Bar Harbor, Me. A breeding nucleus of CBA/N mice was provided by the Animal Production Section, National Institutes of Health, Bethesda, Md. All mice were maintained on Wayne Lab Blox F6 pellets (Allied Mills, Inc., Chicago, Ill.) and chlorinated water acidified to a pH of 3.0 with HCl.

Priming for secondary in vitro antibody response.

Mice were injected with 0.1 milliliter of a 10% suspension of sheep erythrocytes (SRBC) i.p. Six to 8 weeks after priming, they were boosted with the same dose of SRBC administered i.p., and were used 7 days later.

Antigens.

Pooled SRBC were obtained from the Colorado Serum Co., Denver Colo. TNP-LPS was obtained from Dr. John M. Fidler. TNP-AECM-ficoll was purchased from Biosearch, Inc., San Rafael, Calif.

Lymphocyte cultures.

The serum-containing culture medium employed in these experiments was prepared as follows: 100 milliliter contained 90.9 milliliter RPMI 1640 (Flow Laboratories, Inc., Rockville, MD), 0.1 milliliter of $100 \times$ glutamine, 1.0 milliliter of $100 \times$ sodium pyruvate, 1.0 milliliter of $50 \times$ nonessential amino acids, 1.0 milliliter of 1.0 M HEPES[4] buffer (Microbiological Associates, Bethesda, Md), 1.0 milliliter of water containing $10^4$ units of penicillin G and $10^4$ micrograms of streptomycin, and 5.0 milliliter of a supportive lot of fetal calf serum (FCS). Spleen cell suspensions and populations enriched for splenic B cells were prepared as described in Goodman et al., *J. Immunol.*, 121: 1905 (1978).

For evaluation of the primary humoral immune response to SRBC, $10^7$ murine spleen cells were cultured in 1.0 milliliter of 5% FCS-containing medium for 4 days in the presence of antigen at various concentrations, as shown. For evaluation of the secondary humoral immune response to SRBC, $10^7$ spleen cells from primed mice were cultured with various concentrations of SRBC in 1.0 milliliter of 5% FCS-containing medium for 4 or 5 days. Cells were incubated in culture trays (3008, Falcon Plastics, Oxnard, Calif.) at 37° C. in a humidified atmosphere of 10% $CO_2$ in air using tissue culture boxes (CBS Scientific, Del Mar, Calif.) that were rocked at a frequency of 7 cycles per minute.

Mixed lymphocyte culture supernates.

$1.5 \times 10^7$ CBA/CaJ spleen cells were cultured with $1.5 \times 10^7$ BDF$_1$ spleen cells for 4 days in a volume of 5.0 milliliters in a humidified atmosphere of 10% $CO_2$ in air, at 37° C. Cells were pelleted by centrifugation, and the supernatant medium was subjected to 0.22 micron filtration prior to use.

Assay of plaque forming cells (PFC).

PFC-secreting antibodies against SRBC were evaluated after 4 days of culture using a modification of the hemolytic plaque assay of Jerne and Nordin, Science, 40:405 (1963).

Mice.

CBA/CaJ mice, 8–12 weeks of age, were purchased from the Jackson Laboratory, Bar Harbor, Me. NCF$_1$, C57BL/6J nu/nu and nu/+ male mice, weeks of age, were obtained from the mouse breeding facility at Scripps Clinic and Research Foundation, La Jolla, CA. All mice were maintained on Wayne Lab Blox F6 pellets (Allied Mills, Inc., Chicago, IL) and chlorinated water acidified with HCl to a pH of 3.0.

Culture reagents.

Constituents of the serum-free culture medium employed in these studies are described in Goodman et al., *J. Immunol.*, 121:1905 (1978). For serum-containing medium, supportive FCS was substituted for 5% of the volume of RPMI 1640, and HEPES buffer was omitted. *Escherichia coli* 055:B5 LPS was purchased from Difco Laboratories, Detroit, Mich. Concanavalin A was obtained from Miles-Yeda Ltd., Rehovot, Israel. 8-MGuo was purchased from Vega Biochemicals, Tucson, AZ, and from the Sigma Chemical Co., St. Louis, Mo. A.TH anti-A.TL antiserum was obtained from Dr. D.C. Shreffler through Dr. J. G. Ray, Jr., Immunology, Allergic and Immunologic Diseases Program, NIAID, Bethesda, Md.

Cell preparation.

Spleen and thymus cell suspensions were prepared as described in Goodman et al., supra. Spleen cells enriched for T lymphocytes were prepared by passage through nylon wool (NW) columns according to the protocol of Julius et al., *Eur. J. Immunol.*, 3:645 (1973). B cell-enriched populations were prepared by treating $10^8$ spleen cells with a 1:1000 dilution of monoclonal anti-Thy 1.2 (New England Nuclear, Boston, Mass.) for 30 minutes at 4° C. Treated cells were centrifuged at $280 \times$ gravity for 10 minutes, antibodies removed, and the cells resuspended in a 1:6 dilution of CBA RBC-absorbed guinea pig complement at 37° C. for 45 minutes. Cells were then washed and cultured as above. Adherent cells were depleted by passage over columns of Sephadex G-10 as described by Ly and Mishell, *J. Immunol Methods*, 5:239 (1974). Sephadex G-10 adherent cells were recovered by emptying the columns into petri dishes followed by vigorous pipetting. After the beads settled, the cells in suspension were washed three times and used in culture.

Separation of CR and FcR lymphocytes.

Cells bearing receptors for complement were separated by the rosetting procedure of Parish and Hayward, *Proc. R. Soc. Lond. B*, 187:65 (1974), Papers I and II. Briefly, 1 milliliter of RPMI with 10% FCS was combined with 2 milliliters NH$_4$Cl-treated CBA/CaJ spleen cells at $25 \times 10^6$/milliliter and 1 milliliter of a 5% suspension of SRBC that had been previously sensitized with an optimal titer of rabbit anti-SRBC IgM and fresh mouse complement. This mixture was slowly rotated at 20° C. for 30 minutes, pelleted by centrifugation, and incubated at 4° C. for 10 minutes. Pellets were then gently resuspended, allowed to come to R.T., and gently layered on isopaque/ficoll gradients in siliconized tubes. The gradients were centrifuged at $1200 \times$ gravity for 30 min, and pellet and interface cells collected separately. Rosettes were lysed in 0.83% NH$_4$Cl, and cells were counted, washed, and used in culture. Fc receptor-bearing cells were separated by EA rosetting (Parish and Hayward, supra), following the above protocol, with the omission of fresh mouse complement and with the substitution of rabbit anti-SRBC IgG for rabbit anti-SRBC IgM. Enrichment was verified by examination of the separated fractions microscopically. EAC- and EA-non-rosetting fractions each contained 1% rosettes. Cells binding 4 or more erythrocytes were judged to be positive for a particular marker.

Depletion of IgM heavy chain - and IgD heavy chain-bearing cells.

The panning procedure of Wysocki and Sato, *Proc. Natl. Acad. Sci. U.S.A.*, 75:2844 (1978) was used to deplete spleen cells of IgM heavy chain-bearing or IgD heavy chain-bearing lymphocytes. Briefly, 10 milliliters of rabbit anti-mouse IgM heavy chain (50 micrograms/milliliter, Bionetics, Kensington, Md.) or 10-4.22 supernate (50 micrograms/milliliter) was deaggregated by ultracentrifugation at $150,000 \times$ gravity for 60 minutes and the supernatant liquid gently transferred to $100 \times 15$ millimeter polystyrene bacteriological petri dishes. After 1 hour at 20° C., the supernate was decanted, the plate was gently rinsed 4 times with PBS, and 3 milliliters of NH$_4$Cl-treated spleen cells ($10^7$/milliliter) were added to the petri dishes at 4° C. At 40 min, the plates were gently swirled and allowed to incubate an additional 30 minutes. Nonadherent cells were pooled with those obtained from 2 more swirling rinses with PBS. Adherent cells, when used, were removed with a rubber policeman. Nonadherent cells were unresponsive (anti-IgM) or poorly responsive (anti-IgD) to LPS but fully responsive to Con A.

Lympnocyre cultures.

Murine spleen cells were cultured in microculture plates (No. 3546, Costar, Cambridge, Mass.) at a cell density of $4 \times 10^6$ viable cells/milliliter in a volume of 0.1 milliliter. Microcultures were incubated at 37° C. in a humidified atmosphere of 10% CO$_2$ in air. Cultures were fed daily with 8 microliter of nutritional cocktail, Mishell and Dutton, *J. Exp. Med.*, 126:423 (1967).

Measurement of DNA synthesis.

During the final 24 hours of culture, cells were radiolabeled with 1.0 micro Ci of [$^3$H]TdR/culture (5 Ci/mM, Amersham Radiochemicals, Amersham, England). The microcultures were harvested with a Brandel cell harvester, Model M24V (Biological Research and Development Laboratories, Rockville, Md.) onto glass fiber filter strips. Filter disks were transferred to plastic scintillation vials, covered with liquid scintillation cocktail, and counted in a Beckman LS-230 liquid scintillation counter.

Enumeration of blast cells.

Histological preparations were generated on microscope slides from individual lymphocyte cultures with the aid of a cytocentrifuge. Slides were stained with the methyl green-pyronin Y technique of McManus and Mowry, Staining Methods, Harper and Row, New York (1960) pp. 76–78, to simplify the enumeration of pyroninophilic blast cells. Results are expressed as the arithmetic mean of quadruplicate cultures ± the standard error.

Section C

Mice.

CBA/CaJ male mice, 8–16 weeks of age, were purchased from the Jackson Laboratory, Bar Harbor Me. A breeding nucleus of CBA/N mice was provided by the Animal Production Section, National Institutes of Health, Bethesda, Md. All mice were maintained on Wayne Lab Blox F6 pellets (Allied Mills, Inc., Chicago, Ill.) and chlorinated water acidified to a pH of 3.0 with HCl.

Injections.

Mice were injected i.p. with a suspension of washed SRBC at different concentrations in saline. At various times thereafter, different amounts of 8-MGuo or 8-BrGuo were injected i.p. These nucleoside derivatives are insoluble in normal saline, and were particularly effective when used as a suspension. For oral feeding studies, mice were intubated with poly(propylene) catheter extending from the mouth to the stomach, and the measured amounts of the adjuvant compositions were introduced therethrough.

Assay of plaque-forming cells (PFC).

The number of PFC that secreted antibodies against SRBC were evaluated 5–7 days after injection of antigen, using a modification of the hemolytic plaque assay of Jerne and Nordin, supra.

Section D

Mice.

C57BL/6J nu/nu and nu/+, CBA/CaJ and BDF$_1$ male mice, 8–16 weeks of age, were purchased from the mouse breeding facility at Scripps Clinic and Research Foundation, La Jolla, Calif. All mice were maintained on Wayne Lab Blox F6 pellets (Allied Mills, Inc., Chicago, Ill.) and chlorinated water acidified with HCl to a pH of 3.0.

Tissue culture reagents.

Pooled SRBC were obtained from the Colorado Serum Company, Denver, Colo. 8-MGuo and 8-BrGuo were purchased from the Sigma Chemical Company, St. Louis, Mo. IL-2 preparations, prepared by DEAE fractionation as described by Mier and Gallo, *Proc. Natl. Acad. Sci. U.S.A.*, 77:6134 (1980) were obtained from Collaborative Research, Inc., Waltham, Mass.

Lymphocyte cultures.

The serum-containing culture medium employed in these experiments, as well as the methods for preparation of spleen cell suspensions and populations enriched for splenic B cells have been described by Goodman and Weigle, *J. Exp. Med.*, 145:473 (1977). In certain experiments, B cells were produced by in vivo injection of 60 microliters of ATS (lot 15038, Microbiological Associates) 1 and 3 days before use, followed by in vitro ATS, monoclonal anti-thy 1.2, monoclonal anti-Lyt 1.1 and monoclonal anti-Lyt 2.1 (New England Nuclear) treatment and a mixture of rabbit and guinea pig complement, Harwell et al., *J. Exp. Med.*, 152:893 (1980). For evaluation of the primary humoral immune response to SRBC, $10^7$ murine spleen cells or $4-\times 10^6$ murine splenic B cells were cultured in 1.0 milliliter of 5% FCS-containing medium for 4 days in 24-well plastic culture trays (No. 3524, CoStar, Cambridge, Mass.) in the presence or absence of antigen as shown. Cells were incubated at 37° C. in a humidified atmosphere of 10% $CO_2$ in air using tissue culture boxes that were rocked at a frequency of seven cycles per minute.

Measurement of cellular antibody Production.

The direct plaque forming cell (PFC) response to SRBC was evaluated after 4 days of culture using a modification of the hemolytic plaque assay of Jerne and Nordin, supra.

Production of mixed lymphocyte culture (MLC) supernates.

2.5 milliliter each of CBA/CaJ and BDF$_1$ spleen cells were cultured at $6\times 10^6$/milliliter in 60 millimeter petri dishes. Cultures were transferred to tubes, centrifuged, and the supernatant medium harvested 4 days after initiation of culture.

Section E

Mice.

C57BL/6J and C3H/HeN male mice, either 8–16 weeks or 2 years of age, were purchased from the mouse breeding facility at Scripps Clinic and Research Foundation, La Jolla, Calif. All mice were maintained on Wayne Lab Blox F6 pellets (Allied Mills, Inc., Chicago, Ill.) and chlorinated water acidified with HCl to a pH of 3.0.

Antigens and activators.

Pooled SRBC were obtained from the Colorado Serum Company, Denver, Colo. Bacterial lipopolysaccharide (LPS) 055:B5, extracted by the Boivin technique, was purchased from Difco Laboratories, Detroit, Mich. 8-MGuo was purchased from the Sigma Chemical Company, St. Louis, Mo.

Lymphocyte cultures.

The serum-containing culture medium employed in these experiments, as well as the methods for preparation of spleen cell suspensions and populations enriched for splenic B cells have been described by Goodman and Weigle, *J. Exp. Med.*, 145:473 (1977). For induction of polyclonal immunoglobulin secretion, spleen cells were cultured in 24 well plastic plates (No. 3524, CoStar, Cambridge, Mass.) at a cell density of $5\times 10^6$ viable cells/milliliter in a volume of 1.0 milliliter. Culture plates were incubated at 37° C. in a humidified atmosphere of 5% $CO_2$ in air. For evaluation of the primary humoral immune response to SRBC, $10^7$ murine spleen cells or $4-5\times 10^6$ murine splenic B cells were cultured in 1.0 milliliter of 5% FCS-containing medium for 4 days in the presence or absence of antigen, as shown. Cells were incubated in culture trays as above at 37° C. in a humidified atmosphere of 10% $CO_2$ in air using tissue culture boxes that were rocked at a frequency of seven cycles per minute.

Measurement of cellular antibody production.

The direct plaque forming cell (PFC) response to SRBC was evaluated after 4 days of culture using a modification of the hemolytic plaque assay of Jerne and Nordin, supra.

The foregoing is intended as illustrative of the present invention but not limiting. Numerous variations and modifications may be effected without departing from the true spirit and scope of the novel concepts of the invention.

What is claimed is:

1. A method of modulating an animal cellular response comprising contacting animal cells with a composition suitable for modulating an immune response and including as an active ingredient an effective amount of 8-substituted guanine derivative bonded 9-1' to an aldose having 5 or 6 carbon atoms in the aldose chain, said guanine derivative being free of electrically charged functionality, and said 8-substituent having a positive Hammett substituent sigma constant for meta benzoic acid substituents and containing fewer than 15 atoms, together with a diluent amount of a physiologically tolerable carrier.

2. The method in accordance with claim 1 wherein said cell is a leukocyte.

3. The method in accordance with claim 2 wherein said leukocyte is a T lymphocyte.

4. The method in accordance with claim 2 wherein said leukocyte is a macrophage.

5. The method in accordance with claim 2 wherein said leukocyte is a B lymphocyte.

6. The method according to claim 2 wherein said leukocyte is a neutrophil.

7. The method in accordance with claim 5 including the additional step of subjecting said B lymphocyte to an antigen prior to contact with said composition.

8. The method according to claim 7 wherein said B lymphocyte is contacted with said composition in conjunction with an additional amount of antigen.

9. The method according to claim 8 wherein said composition is contacted with said B lymphocytes in an environment exhibiting T lymphocyte helper activity.

10. The method according to claim 8 wherein said B lymohocytes are contacted with said composition in an environment exhibiting substantially no T lymphocyte helper activity.

11. The method in accordance with claim 8 wherein said B lymphocytes exhibit a diminished immune response prior to said contacting.

12. The method in accordance with claim 2 wherein said leukocytes are contacted with said composition in vivo.

13. The method in accordance with claim 1 wherein said aldose has the structure

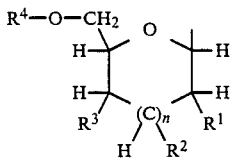

wherein n is one or zero;

$R^1$ is hydrogen, hydroxy, methoxy, ethoxy or acetoxy, $R^2$ is hydroxy, methoxy, ethoxy, acetoxy, amino, mono- or di-substituted $C_1$-$C_2$ amino or acetamido;

$R^3$ is hydroxy, methoxy, ethoxy or acetoxy, and $R^4$ is hydrogen, methyl, ethyl or the acyl portion of a carboxylic acid having one to about 24 carbon atoms.

14. The method in accordance with claim 13 wherein n is zero;

$R^1$ is hydroxy, $R^3$ is hydroxy, and $R^4$ is hydrogen.

15. The method in accordance with claim 1 wherein said active ingredient is suspended in said carrier.

16. The method in accordance with claim 13 wherein n is zero;

$R^1$ is hydrogen or hydroxy;

$R^3$ is hydroxy, and $R^4$ is hydrogen.

17. The method in accordance with claim 1 wherein said aldose is ribose.

* * * * *